United States Patent
Seeberger et al.

(10) Patent No.: US 9,409,142 B2
(45) Date of Patent: Aug. 9, 2016

(54) METHOD AND DEVICE FOR THE SYNTHESIS OF ARTEMISININ

(71) Applicant: MAX-PLANCK-GESELLSCHAFT ZUR FÖRDERUNG DER WISSENSCHAFTEN E.V., Munich (DE)

(72) Inventors: Peter H. Seeberger, Kleinmachnow (DE); Daniel Kopetzki, Hannover (DE); Francois Lévesque, Berlin (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 14/810,882

(22) Filed: Jul. 28, 2015

(65) Prior Publication Data

US 2015/0328617 A1    Nov. 19, 2015

Related U.S. Application Data

(62) Division of application No. 14/241,584, filed as application No. PCT/EP2012/066800 on Aug. 29, 2012, now Pat. No. 9,150,535.

(30) Foreign Application Priority Data

Aug. 29, 2011 (EP) .................................... 11007018
Jan. 16, 2012 (EP) .................................... 12151330
Jun. 25, 2012 (EP) .................................... 12173472

(51) Int. Cl.

| | | |
|---|---|---|
| *C07D 321/00* | (2006.01) | |
| *B01J 19/12* | (2006.01) | |
| *C07D 493/22* | (2006.01) | |
| *B01J 19/08* | (2006.01) | |
| *C07D 321/10* | (2006.01) | |

(52) U.S. Cl.
CPC ...... *B01J 19/12* (2013.01); *B01J 19/08* (2013.01); *C07D 321/10* (2013.01); *C07D 493/22* (2013.01); *B01J 2219/0871* (2013.01); *B01J 2219/0892* (2013.01)

(58) Field of Classification Search
CPC ........................................................ B01J 19/12
USPC ........................................................ 549/348
See application file for complete search history.

(56) References Cited

U.S. PATENT DOCUMENTS

| 4,992,561 A | 2/1991 | Roth et al. |
| 2007/0215455 A1 | 9/2007 | Folkmann et al. |
| 2011/0230669 A1 | 9/2011 | Kraft et al. |

FOREIGN PATENT DOCUMENTS

| EP | 2289897 | 3/2011 |
| WO | WO 2006/128126 | 11/2006 |
| WO | WO 2007/082533 | 7/2007 |
| WO | WO 2009/088404 | 7/2009 |
| WO | WO 2011/030223 | 3/2011 |

OTHER PUBLICATIONS

Bou-Hamadan et al. Beilstein Journal of Organic Chemistry, 2011, 7, 1124-1129.*
Acton et al., "On the Conversion of Dihydroartemisinic Acid into Artemisinin" J. Org. Chem. (1992) 57:3610-3614.
Bou-Hamdan et al., "Continuous flow photolysis of aryl azides: Preparation of 3H-azeinones" Beilstein Journal of Organic Chemistry (2011) 7:1124-1129 (including supporting information).
Braun et al., "Up-scaling photochemical reactions" Advances in Photochemistry (1993) 18:235-313.
Brown, G. D., "The Biosynthesis of Artemisinin (Qinghaosu) and the Phytochemistry of *Artemisia annua* L. (Qinghao)" Molecules, (2010)15:7603-7698.
Chen et al., "α-Hydroxylation of Enolates and Silyl Enol Ethers" Organic Reactions (2004) 64:1-356.
Constantino et al., "A Novel Asymmetric Total Synthesis of (+)-Artemisinin" Syn. Comm. (1996) 26:321-329.
Hoffmann, "Photochemical Reactions as Key Steps in Organic Synthesis" N. Chem. Rev. (2008) 108:1052-1103.
Hook et al., "A Practical Flow Reactor for Continuous Organic Photochemistry" J. Organometallic Chem. (2005) 70:7558-7564.
Lange et al., "Catalytic rearrangement of an aliphatic hydroperoxide" Catal. Comm. (2002) 3:25-28.
Olah, et al., "Superacid-Catalyzed Oxygenation of Alkanes" Angew. Chem. Int. Ed. Engl. (1978) 17:909-931.
Ro et al., "Production of the antimalarial drug precursor artemisinic acid in engineered yeast" Nature (2006) 440:940-943.
Roth et al., "A Simple Conversion of Artemisinic Acid into Artemisinin" J. Nat. Prod. (1989) 52:1183-1185.
Roth et al., "A Facile Semisynthesis of the Antimalarial Drug Qinghaosu" J. Chem. Edu. (1991) 68:612-613.
Schweitzer et al., "Physical Mecahnisms of Generation and Deactivation of Singlet Oxygen" Chem. Rev. (2003) 103:1685-1758.

(Continued)

*Primary Examiner* — Nizal Chandrakumar
(74) *Attorney, Agent, or Firm* — Knobbe, Martens, Olson & Bear, LLP

(57) ABSTRACT

The present invention is directed to a method for producing artemisinin having the formula

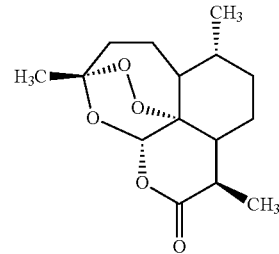

from dihydroartemisinic acid in a continuous flow reactor using singlet oxygen as well as to the continuous flow reactor for producing artemisinin.

10 Claims, 13 Drawing Sheets

(56) References Cited

OTHER PUBLICATIONS

Wallaart et al., "Isolation and Identification of Dihydroartemisinic Acid from Artemisia annua and Its Possible Role in the Biosynthesis of Artemisinin" J. Nat. Prod. (1999) 62:430-433.
White, N. J., "Qinghaosu (Artemisinin): The Price of Success" Science (2008) 320:330-334.
World Malaria Report 2010, WHO Geneva.
Yadav, et al., "Stereoselective total synthesis of (+)-artemisinin" Tetrahedron Lett. (2003) 44:387-389.
Zhang, Y. et al., "The Molecular Cloning of Artemisinic Aldehyde Δ11(13) Reductase and Its Role in Glandular Trichome-dependent Biosynthesis of Artemisinin in *Artemisia annua*" J. Biol. Chem. (2008) 31:21501-21508.
International Search Report and Written Opinion mailed on Jan. 21, 2013 for PCT Application No. PCT/EP2012/066800, filed on Aug. 29, 2012.
International Preliminary Report on Patentability completed on Nov. 6, 2013, for PCT Application No. PCT/EP2012/066800, filed on Aug. 29, 2012.

\* cited by examiner

METHOD AND DEVICE FOR THE SYNTHESIS OF ARTEMISININ

The present invention is directed to a method for converting dihydroartemisinic acid with singlet oxygen in a continuous flow reactor as a key step for producing artemisinin which has been used for a long time as anti-malaria drug, as well as to the continuous flow reactor for producing artemisinin.

Malaria, caused by the protozoan parasite *Plasmodium falciparum*, remains a major global health problem that kills almost one million people each year. Artemisinin is currently the most effective treatment against multi-drug resistant *Plasmodium* species and artemisinin combination treatments (ACTs) are now first-line drugs (World Malaria Report 2010, WHO Geneva, 2010). Artemisinin belongs to the group of sesquiterpenes and has an uncommon trioxane ring structure and a peroxide bridge. Access to this sesquiterpene endoperoxide molecule relies on extraction and isolation from the leaves and blossoms of the plant *Artemisia annua* (sweet wormwood) that has been cultivated in many countries for that purpose (White, N. J. *Science,* 2008, 320, 330-334). The natural synthesis of artemisinin starts with isopentenyl pyrophosphate (IPP) and its isomer dimethylallyl pyrophosphate to dihydroartemisinic acid and involves as intermediate product amorpha-4,11-diene (Brown, G. D. *Molecules,* 2010, 15, 7603-7698). Total synthesis of artemisinin is too laborious to be considered viable for supplying the highly cost sensitive market. Artemisinic acid, a much less complex molecular precursor can be extracted from the same plant and can be produced in engineered *Saccharomyces cerevisiae* (Ro, D.-K., et al., *Nature,* 2006, 440, 940-943). Therefore, artemisinic acid is a good starting point for the synthesis of the drug substance. Still, the conversion of artemisinic acid to artemisinin has proven a formidable challenge for chemists since a high-yielding and scalable low cost process for the construction of this highly complex molecule is needed.

WO 2009/088404 A1 discloses a synthesis for artemisinin starting from dihydroartemisinic acid (DHAA)

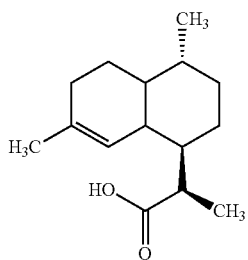 [SMILES: CC1=CC2C(CC1)[C@H](C)CC[C@H]2[C@@H](C)C(=O)O]

which is in a first step converted to a dihydroartemisinic acid ester of the following formula

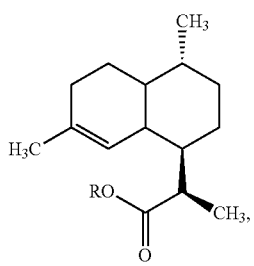

wherein R is an alkyl, alkenyl, alkynyl, aryl, cycloalkyl, alkaryl or aralkyl group. The dihydroartemisinic acid ester is than reacted with a peroxidizing agent in order to obtain the dihydroartemisinic acid ester peroxide of the following formula

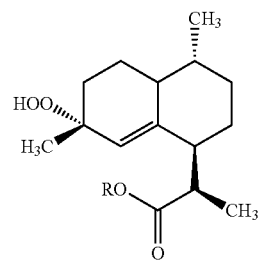

which is than converted to artemisinin by the reaction with oxygen. This four step synthesis is quite long and requires optimization especially for large scale synthesis in order to shorten this synthesis route, to reduce labor costs, purification efforts and to increase yield.

Thus there is a need to provide a more efficient synthesis of artemisinin.

Artemisinic acid and dihydroartemisinic acid, both bicyclic molecules, lack much of the complexity that imparts the biological activity to artemisinin, a sesquiterpene endoperoxide with a dense array of functional groups. Access to large quantities of artemisinic acid via engineered yeast (Ro, D. K. et al. *Nature,* 2006, 440, 940-943), rendered artemisinic acid (1) an attractive starting material for chemical semi-synthesis of artemisinin. The conversion of artemisinic acid to artemisinin involves several challenging steps that were examined in the context several synthetic endeavors (a) Roth, R. J.; Roth, N. A. U.S. Pat. No. 4,992,561 1991 b) Reiling, K. K.; Renninger, N. S.; McPhee, D. J.; Fisher, K. J.; Ockey, D. A. International Patent WO 2006/128126 A1 2006. c) Roth, R. J.; Acton, N. *J. Chem. Edu.* 1991, 68, 612-613. d) Roth, R. J.; Acton, N. A *J. Nat. Prod.* 1989, 52, 1183-1185. e) Constantino, M. G.; Beltrame Jr. M.; da Silva, G. V. *J. Syn. Comm.* 1996, 26, 321-329.). Current solutions to this problem are technically too complex for scale-up while meeting stringent cost targets. Photochemical transformations have the advantage that light is a relatively inexpensive and mild reagent, but were not used often for drug synthesis since they are hard to scale up. The distance light can penetrate through solutions is limited due to absorption and moving to larger reaction vessels greatly diminishes conversion and yield.

Molecular oxygen is in this regard an attractive reagent due to its availability, low cost and negligible environmental impact. Singlet oxygen ($^1O_2$) is formed via dye-sensitized photoexcitation of triplet oxygen ($^3O_2$) and facilitates heteroatom oxidations, ene reactions, as well as [4+2] and [2+2] cycloadditions (a) Schweitzer, C.; Schmidt, R. *Chem. Rev.,* 2003, 103, 1685-1758. b) Hoffmann, N. *Chem. Rev.* 2008, 108, 1052-1103.). Consequently, $^1O_2$ has been used for the synthesis of natural products and fragrances. Widespread use of $^1O_2$ in conventional batch systems has been prevented by the need for specialized equipment to produce the reagent and technical challenges associated with scaling-up photochemical reactions and the low rate of mass transfer of oxygen gas. First approaches to the use of singlet oxygen ($^1O_2$) in the conversion of dihydroartemisinic acid have been made in recent years. In *J. Org. Chem.* 1992, 57, 3610 the conversion of dihydroartemisinic acid to artemisinin by use of singulet oxygen and methylene blue in photooxidation and subsequently use of trifluoroacetic acid in a batch process has been described. The same reaction and reaction conditions have been disclosed in U.S. Pat. No. 4,992,561. These processes suffer from low yields and very long conversion times to finally get artemisinin.

Also, artemisinic acid can be reduced to dihydroartemisinic acid using batch methods such as diimide on large scale (WO 2011/030223 A2). The three-step reaction sequence to convert dihydroartemisinic acid to artemisinin involving photochemically induced oxidation with singlet oxygen, acid-mediated Hock cleavage (a) Lange, J.-P.; Breed, A. J. M. *Catal. Comm.* 2002, 3, 25-28. b) Olah, G. A.; Parker, D. G.; Yoneda, N. *Angew. Chem. Int. Ed. Engl.* 1978, 17, 909-931) and oxidation with triplet oxygen (Chen, B.-C., Zhou, P.; Davis, F. A.; Ciganek, E. *Organic Reactions* 2004, 64, 1-356) pose synthetic challenges which have not been solved, and hence those reactions remain to be performed with batch methods and all disadvantages associated therewith.

In contrast, continuous flow reactors allow easy scale-up as no change in reactor size is required, provide a large surface-to-volume ratio that ensures efficient irradiation and enable precise control over the reaction time to minimize unwanted side reactions due to secondary photochemical reactions. In addition, continuous flow reactors improve safety as reactive intermediates are quenched or further transformed immediately after production. Photochemical flow reactors have been explored for the generation and use of $^1O_2$. Although complete conversion was achieved in a short residence time, the process suffered from very low productivity, rendering the system inapplicable to use on industrial scale. Alternatively, this problem of low $O_{2(g)}$ mass transfer has been tackled by using supercritical carbon dioxide as a solvent, though this requires a highly specialized reaction set-up.

Efficient oxidations are dependent on the solution concentration of $^1O_2$, which in turn is proportional to the solution concentration of $^3O_2$. Therefore, the productivity of the oxidation depends on the rate of mass transfer $(d[^3O_{2(sol)}]/dt)$ of $^3O_{2(g)}$ into the solution. Based on Fick's Law (Equation {1}) the rate of mass transfer is determined by the liquid film transfer coefficient ($K_L$), the specific surface area of the solution (a) and the oxygen deficit within the solution $([^3O_{2(sol)}]_{sat}-[^3O_{2(sol)}])$.

$$d[^3O_{2(sol)}]/dt = K_L a([^3O_{2(sol)}]sat - [^3O_{2(sol)}]) \quad \{1\}$$

When biphasic gas-liquid reactions are conducted at high flow rates, the specific surface areas in continuous flow reactors (up to 25300 m²/m³) can greatly exceed those attained in conventional batch reactors (up to 2000 m²/m³) due to flow pattern effects. To date, synthetic organic chemists have not taken full advantage of variations in the flow patterns of biphasic reactions.

Intending to utilize continuous flow chemistry as a means to scale-up photochemical transformations the inventors examined the transformation of artemisinic acid (1) or dihydroartemisinic acid (2) to artemisinin (6) mindful of the necessity to create a simple, scalable and inexpensive process.

Objective of the present invention is to provide a more efficient synthesis of artemisinin.

The objective of the present invention is solved by the teaching of the independent claims. Further advantageous features, aspects and details of the invention are evident from the dependent claims, the description, the figures, and the examples of the present application.

It was found that artemisinin can be prepared in a one continuous flow process from dihydroartemisinic acid (2) by the use of singlet oxygen. A simple continuous flow system renders reactions involving singlet oxygen ($^1O_2$) practical for large scale synthetic synthesis of artemisinin. Efficient mass transfer and sufficient irradiation enable the straightforward production and use of $^1O_2$ as a reagent in one continuous flow process for synthesis of artemisinin (6) starting from dihydroartemisinic acid (2). Dihydroartemisinic acid is commercially available from Honsea Sunshine Biotech Co., Ltd. or can be produced by a modified yeast (Zhang, Y. et al. *J. Biol. Chem.* 2008, 31, 21501-21508).

DESCRIPTION

Thus, the present invention is directed to a method for producing artemisinin (6) from dihydroartemisinic acid (2) comprising or consisting of the following steps:

A) providing dihydroartemisinic acid (2) represented by the following formula

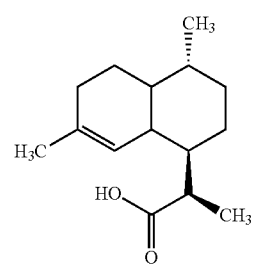

(2)

B) performing in a continuous flow reactor the following reactions
i) photooxidation of dihydroartemisinic acid (2) with singlet oxygen,
ii) followed by an acid mediated cleavage and
iii) subsequent oxidation with triplet oxygen in order to obtain artemisinin (6) of the following formula:

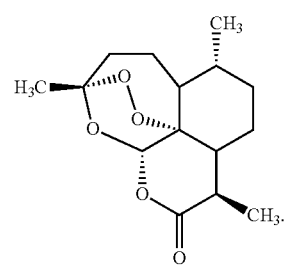

(6)

For this method it is preferred when all three steps i), ii) and iii) are performed in a continuous manner.

In case a chemical synthesis of dihydroartemisinic acid (2) is desired, dihydroartemisinic acid (2) can be prepared by reducing artemisinic acid (1). Thus, dihydroartemisinic acid (2) can be obtained by reducing artemisinic acid (1) of the following formula

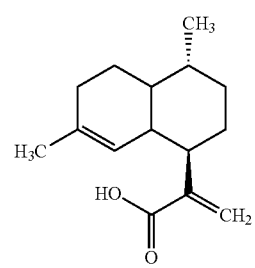

(1)

to dihydroartemisinic acid (2).

Thus the present invention is also directed to a method for producing artemisinin (6) from artemisinic acid (1) comprising the following steps:

A) providing artemisinic acid (1) represented by the following formula

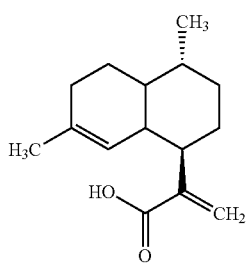

(1)

B) reducing artemisinic acid (1) to dihydroartemisinic acid (2) of the following formula

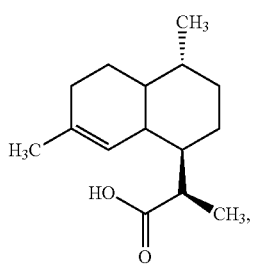

(2)

C) performing in a continuous flow reactor the following reactions
  i) photooxidation of dihydroartemisinic acid (2) with singlet oxygen,
  ii) followed by an acid mediated cleavage and
  iii) subsequent oxidation with triplet oxygen
in order to obtain artemisinin (6) of the following formula:

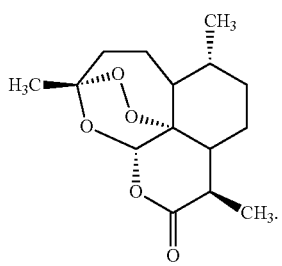

(6)

For the afore-mentioned method it is preferred when all three steps i), ii) and iii) are performed in a continuous manner.

The continuous flow reactor according to the present invention is a reactor, wherein at least the photooxidation of dihydroartemisinic acid (2) of the different reactions for the conversion of dihydroartemisinic acid (2) to artemisinin (6) can be performed in a continuous manner. The term "continuous" as used herein means, for instance, that there is provided a flow of a solution or mixture containing dihydroartemisinic acid (2) to the reactor which is continuously converted while flowing through the reactor system in the direction from an inlet to an outlet such that a reaction product can be continuously derived at the outlet of the reactor without dividing the reaction mixture into parts. The term "continuous" or "continuously" can be defined as a movement of the solution or mixture containing dihydroartemisinic acid (2) through the photochemical reactor while irradiated or while exposed to the light of the light source. This movement should only be in one direction, namely from the inlet to the outlet of the photochemical reactor or in other words from the mixing device or from the reservoir containing the starting materials (e.g. containing the solution of dihydroartemisinic acid (2) and optionally also the photosensitizer) to the feed of the acidic solution or to the reactor 15. The movement could also temporarily stop (velocity of the movement is zero) during a part of the time of the photooxidation. Thus during the time of the photooxidation, there must be a movement for a certain time in the direction described above.

Thus, the term "continuous" as used herein refers to an endless flow of a solution or mixture containing dihydroartemisinic acid (2) through the photochemical reactor. Of course the flow through the photochemical reactor is theoretically endless and in practice will end after a certain time when for example the light source has to be replaced, the oxygen tank is empty or any part of the photochemical reactor has to be repaired or replaced or the reservoir of the dihydroartemisinic acid (2) starting material is empty. However in order to define the term "continuous" a theoretically endless flow of the solution or mixture containing dihydroartemisinic acid (2), oxygen and the photosensitizer can be assumed which flows through the photochemical reactor wherein this solution or mixture is exposed to the light generated by the light source. However, this flow does not require a steady or continuous flow rate (measured in volume per time). The flow rate can be constant, can be increased and decreased stepwise over the time, can follow a sinus curve, can be increased and decreased continuously (like a zig-zag curve), can be zero for a certain time or can be coupled to the conversion rate of the dihydroartemisinic acid (2), thus increasing the flow rate if the conversion rate is above a predefined limit or reducing the flow rate if the conversion rate is below a predefined limit or can also be arbitrarily adjusted. Thus, the term "continuous" as used herein means that the photooxidation is not performed batchwise. Thus, the term "continuous" as used herein means that not definite volumes of the solution or mixture containing dihydroartemisinic acid (2) are exposed to the light of the light source over a certain time like a batch process does. The term "continuous" as used herein means that over a certain or predefined time the volume of the solution or mixture containing dihydroartemisinic acid (2) is not constant. This is because a solution or mixture containing dihydroartemisinic acid (2) enters as starting material the photochemical reactor, thus increasing the volume which is exposed to the light of the light source while most preferably the same volume of irradiated solution or mixture containing the photooxidation product of dihydroartemisinic acid (2) leaves the photochemical reactor within said time. The volume of the solution or mixture containing dihydroartemisinic acid (2) would only be constant if the flow rate is zero during the complete time of the photoreaction like in a batch process. Also, the volume of the solution or mixture containing dihydroartemisinic acid (2) is not supposed to be driven such that a product containing mixture after exposure of irradiation exits the reactor at the inlet. That is, the solution or mixture containing dihydroartemisinic acid (2) shall not be led reverse in direction from the outlet to the inlet. The term "continuous" as used herein clearly distinguishes from a process where the solution or mixture containing dihydroartemisinic acid (2) is led into the reactor from the inlet in direction of the outlet, is then stopped and irradiated, and afterwards rather sucked out of the reactor back in direction of the inlet in order to collect a product containing mixture at the end of the inlet, just as it may be performed in batch-wise process. It may happen for the solution or mixture containing dihydroartemisinic acid (2) being driven reversely for test reasons, but only in order that the total direction of the continuous flow is driven towards the outlet, that is if driven shortly in reverse direction it must follow a longer period of flow in direction of the outlet. Further, the term continuous may also comprise that solution or mixture containing dihydroartemisinic acid (2) is driven shortly once or several times or even fluctuating reversely if followed by a period where a bigger volume is driven in direction of the outlet. That is, the solution or mixture containing dihydroartemisinic acid (2) may be shortly driven reversely as long as no product exits the reactor at the inlet end and the total direction of all volume in the reactor is from inlet to outlet.

Thus, the continuous flow as described herein may occur at a steady or a fluctuating flow rate. In case of a fluctuating flow the reaction mixture may also stop intermediately or periodically, hence the flow rate may fall down to zero. However, if once stopped the continuous flow has to continue in the direction from the inlet to the outlet of the reactor. "Continuous" as used herein also means that a desired product can be provided steadily without the necessity of starting a novel experiment or batch in order to increase the amount of the desired product after the reaction took place. The reaction set-up and the reactor design allow a steadily increasing amount of product when starting material is provided without upscaling the reactor dimensions. "Continuous" further means that if a starting material is constantly provided and converted, the conversion compound is consistently produced.

In the continuous flow reactor according to the present invention at least the photooxidation of dihydroartemisinic acid (2) with singlet oxygen is performed in a continuous manner, while an acid mediated cleavage and subsequent oxidation with triplet oxygen may also be performed in a semi-batch manner or in a batch reactor. Thus at least the photooxidation in the photochemical reactor is performed continuously which means in a continuous manner as defined above, while the acid mediated cleavage [step ii)] and the oxidation with triplet oxygen [step iii)] do not necessarily have to be conducted in a continuous manner. However it is preferred that also step ii), namely the acid mediated cleavage and more preferred the acid mediated cleavage and step iii), namely the oxidation with triplet oxygen are conducted also in a continuous manner. The continuous manner of step ii) and step iii) can be different from the continuous manner of step i). This means that different flow rates are normally used for the steps i), ii) and iii). Step ii) can normally be processed with the highest flow rate while step i) normally has the lowest flow rate of all three steps.

Therefore, the continuous flow reactor of the present invention comprises at least a photochemical reactor, wherein the conversion of dihydroartemisinic acid (2) with singlet oxygen takes place continuously, i.e. in a continuous manner.

As the photochemical reactor is comprised by the continuous flow reactor of the present invention every modification as being described below for the photochemical reactor also applies to the continuous flow reactor.

The photochemical reactor for the production of artemisinin from dihydroartemisinic acid comprises or consists of
a light source 11,
mixing device for mixing oxygen with a solution of dihydroartemisinic acid,
reactor compartment being at least partially irradiated by the light source and having an inlet for the mixture of dihydroartemisinic acid and oxygen on its one end and an outlet for the reacted products on the opposite end.

An alternative embodiment of the photochemical reactor for the production of artemisinin from dihydroartemisinic acid comprises or consists of
a light source 11,
mixing device for mixing oxygen with a solution of dihydroartemisinic acid,
reactor compartment exposed to the light source for irradiating the mixture of the solution of dihydroartemisinic acid and oxygen when the mixture passes the reactor compartment.

A further alternative embodiment of the photochemical reactor for the production of artemisinin from dihydroartemisinic acid comprises or consists of
a light source 11,
mixing device for mixing oxygen with a solution of dihydroartemisinic acid,
reactor compartment for carrying out the photooxidation and which is at least partially irradiated by the light source and which has at least one inlet for the solution of dihydroartemisinic acid and oxygen and at least one outlet for the solution after the photooxidation.

A further alternative embodiment of the photochemical reactor for the production of artemisinin from dihydroartemisinic acid comprises or consists of
a light source 11,
mixing device for mixing oxygen with a solution of dihydroartemisinic acid,
reactor compartment for irradiation of the solution of dihydroartemisinic acid and the oxygen by the light source when the solution flows through the reactor compartment.

Still a further alternative embodiment of the photochemical reactor for the production of artemisinin from dihydroartemisinic acid comprises or consists of
a light source 11,
mixing device for mixing oxygen with a solution of dihydroartemisinic acid,
reactor compartment being at least partially irradiated by the light source and having an inlet for the mixture of the solution of dihydroartemisinic acid and oxygen on its one end and an outlet for the reacted products on the opposite end.

The continuous flow reactor of the present invention comprises one of the afore-mentioned photochemical reactors. Even if not explicitly mentioned, the solution of dihydroartemisinic acid and the mixture of the solution of dihydroartemisinic acid and oxygen preferably comprise or contain a photosensitizer.

The photochemical reactor or the continuous flow reactor preferably further comprises an oxygen source capable of providing oxygen above atmospheric pressure. The oxygen source is preferably an oxygen tank 4 with a manometer 3. The oxygen source can also be used to generate pressure so that the photooxidation according to step i) or all three steps i)-iii) can be performed under pressure. The pressure and especially the oxygen pressure increase the yield of the photooxidation product of step i) and thus leads finally to an increased yield of artemisinin. Thus it is preferred to carry out the photooxidation of step i) under pressure and especially under oxygen pressure. It is more preferred to carry out all three steps i)-iii) under pressure and especially under oxygen pressure. Therefore it is further preferred that oxygen for the provision of singlet oxygen is provided to the continuous flow reactor and/or the photochemical reactor above atmospheric pressure.

Preferably the reactor compartment is a tubing 7.

Also preferred as mixing device is a T-mixer valve.

The photochemical reactor further comprises preferably
- a box which is impervious to light with light reflecting inner walls and one opening through which the tubing 7 enters the box and another opening through which the tubing 7 leaves the box and
- multiple loops of the tubing 7 arranged in the inside of the box, wherein the tubing 7 has an inlet for a mixture of dihydroartemisinic acid and oxygen on its one end before entering the box and an outlet for the reacted products on the opposite end after leaving the box.

Preferably the photochemical reactor or the continuous flow reactor further comprises a cooling liquid and a chiller.

Especially preferred is if the photochemical reactor or the continuous flow reactor further comprises a back pressure regulator 14.

A continuous flow reactor of the present invention for the production of artemisinin from dihydroartemisinic acid comprises or consists of:
- a light source 11,
- a mixing device for mixing oxygen with a solution of dihydroartemisinic acid,
- a reactor compartment exposed to the light source for performing the photooxidation,
- a feed for an acidic solution.

The feed for an acidic solution can be incorporated into the continuous flow reactor of the present invention before or after the photochemical reactor as defined herein. That is, in one embodiment of the present invention the feed for an acidic solution is incorporated after the photochemical reactor, and if present before a reactor 15. In such an embodiment the feed for an acidic solution comprises separate reactor component. In another embodiment of the present invention the feed for an acidic solution is incorporated before the photochemical reactor. In such embodiment the feed for an acidic solution may be a separate reactor component to the feed of the other starting materials such as dihydroartemisinic acid, solvent and oxygen. In another embodiment the feed for an acidic solution may be incorporated into the feed for dihydroartemisinic acid, photosensitizer and solvent. That is, the continuous flow reactor of the present invention comprises one reactor component which provides dihydroartemisinic acid, solvent and the acid for the acid mediated cleavage simultaneously. In such an embodiment dihydroartemisinic acid, photosensitizer, solvent and acid are provided by one solution.

Thus, the acid for the acid mediated cleavage of the product of the photooxidation of dihydroartemisinic acid can be added before the photooxidation directly into the solution of dihydroartemisinic acid and the photosensitizer before or after the oxygen is added. In this case the acid for the acid mediated cleavage is already present during the photooxidation and the acid mediated cleavage starts to take place in the photochemical reactor or respectively the reactor compartment. In another embodiment the acid for the acid mediated cleavage is added after the photooxidation, i.e. after or respectively downstream the photochemical reactor or the reactor compartment and preferably before the reactor 15 (if present) or the acid for the acid mediated cleavage is added into the reactor 15 (if present) in order to perform the acid mediated cleavage within reactor 15 (if present). Thus there can be a feed for the acidic solution into reactor 15 (if present) or into the reaction solution after the photochemical reactor or after the reactor compartment and before reactor 15 (if present) or into the solution of dihydroartemisinic acid before the oxygen is added or into the solution of dihydroartemisinic acid after the oxygen is added and before this solution enters the photochemical reactor or the reactor compartment or into the reaction solution within the photochemical reactor or the reactor compartment.

Thus, one embodiment of continuous flow reactor of the present invention for the production of artemisinin from dihydroartemisinic acid comprises or consists of:
- a feed for dihydroartemisinic acid, photosensitizer and solvent,
- an oxygen source,
- a light source 11,
- a mixing device for mixing oxygen with a solution of dihydroartemisinic acid,
- a reactor compartment exposed to the light source for performing the photooxidation,
- a feed for an acidic solution.

This continuous flow reactor preferably also comprises a reactor 15 for performing the triplet oxygen oxidation and optionally for collecting the product. Most preferably the above continuous flow reactor further comprises a back-pressure regulator 14 in order to perform at least the photooxidation reaction [step i)] under pressure. The feed for dihydroartemisinic acid, photosensitizer and solvent may consist of three different supplies, wherein in each supply one of the components is provided, i.e. one supply for dihydroartemisinic acid, one supply for the photosensitizer and one supply for the solvent. It is also possible that the feed for dihydroartemisinic acid, photosensitizer and solvent consist of only one supply for a solution of dihydroartemisinic acid, photosensitizer and solvent. Also, it is possible that feed for dihydroartemisinic acid, photosensitizer and solvent combines two supplies for two components and has one separate supply, i.e. for example a supply for dihydroartemisinic acid and solvent in the form of a dihydroartemisinic acid solution on the one hand and one supply for the photosensitizer. It is also possible that a solution of dihydroartemisinic acid in the solvent represents one supply and a solution of photosensitizer in the same or in another solvent represents a second supply. The feed for an acidic solution is preferably located downstream to the reactor compartment so that the acid is preferably added after the photooxidation. The reactor compartment is the part of the photochemical reactor or the part of the continuous flow reactor through which the solution or mixture containing dihydroartemisinic acid (2) flows while being irradiated by the light of the light source.

The continuous flow reactor for the production of artemisinin from dihydroartemisinic acid downstream to the feed of starting materials comprises or consists of
- a light source 11,
- mixing device for mixing oxygen with a solution of dihydroartemisinic acid,
- reactor compartment being at least partially irradiated by the light source and having an inlet for the mixture of dihydroartemisinic acid and oxygen on its one end and an outlet for the reacted products on the opposite end, and
- a feed for an acidic solution.

This continuous flow reactor preferably also comprises a reactor 15 for performing the triplet oxygen oxidation and optionally for collecting the product. Most preferably the above continuous flow reactor further comprises a back-pressure regulator 14 in order to perform at least the photooxidation reaction [step i)] under pressure.

An alternative embodiment of the continuous flow reactor for the production of artemisinin from dihydroartemisinic acid downstream to the feed of starting materials comprises or consists of
- a light source 11,
- mixing device for mixing oxygen with a solution of dihydroartemisinic acid,
- reactor compartment exposed to the light source for irradiating the mixture of dihydroartemisinic acid and oxygen when the mixture passes the reactor compartment, and
- a feed for an acidic solution.

This continuous flow reactor preferably also comprises a reactor 15 for performing the triplet oxygen oxidation and optionally for collecting the product. Most preferably the above continuous flow reactor further comprises a back-pressure regulator 14 in order to perform at least the photooxidation reaction [step i)] under pressure.

A further alternative embodiment of the continuous flow reactor for the production of artemisinin from dihydroartemisinic acid downstream to the feed of starting materials comprises or consists of
- a light source 11,
- mixing device for mixing oxygen with a solution of dihydroartemisinic acid,
- reactor compartment for carrying out the photooxidation and which is at least partially irradiated by the light source and which has at least one inlet for the solution of dihydroartemisinic acid and oxygen and at least one outlet for the solution after the photooxidation, and
- a feed for an acidic solution.

This continuous flow reactor preferably also comprises a reactor 15 for performing the triplet oxygen oxidation and optionally for collecting the product. Most preferably the above continuous flow reactor further comprises a back-pressure regulator 14 in order to perform at least the photooxidation reaction [step i)] under pressure.

A further alternative embodiment of the continuous flow reactor for the production of artemisinin from dihydroartemisinic acid downstream to the feed of starting materials comprises or consists of
- a light source 11,
- mixing device for mixing oxygen with a solution of dihydroartemisinic acid,
- reactor compartment for irradiation of the solution of dihydroartemisinic acid and the oxygen by the light source when the solution flows through the reactor compartment, and
- a feed for an acidic solution.

This continuous flow reactor preferably also comprises a reactor 15 for performing the triplet oxygen oxidation and optionally for collecting the product. Most preferably the above continuous flow reactor further comprises a back-pressure regulator 14 in order to perform at least the photooxidation reaction [step i)] under pressure.

Still a further alternative embodiment of the continuous flow reactor for the production of artemisinin from dihydroartemisinic acid downstream to the feed of starting materials comprises or consists of
- a light source 11,
- mixing device for mixing oxygen with a solution of dihydroartemisinic acid,
- reactor compartment being at least partially irradiated by the light source and having an inlet for the mixture of dihydroartemisinic acid and oxygen on its one end and an outlet for the reacted products on the opposite end, and
- a feed for an acidic solution.

This continuous flow reactor preferably also comprises a reactor 15 for performing the triplet oxygen oxidation and optionally for collecting the product. Most preferably the above continuous flow reactor further comprises a back-pressure regulator 14 in order to perform at least the photooxidation reaction [step i)] under pressure.

All the above embodiments of the continuous flow reactor of the present invention may further comprise an additional reactor 16, or two additional reactors 16 and 17 and may also comprise a collection flask 18 for collecting the artemisinin containing solution.

In a preferred embodiment the continuous flow reactor of the present invention for the production of artemisinin from dihydroartemisinic acid comprises or consists of:
- a light source 11,
- a mixing device for mixing oxygen with a solution of dihydroartemisinic acid,
- a reactor compartment exposed to the light source for performing the photooxidation,
- a feed for an acidic solution,
- at least one reactor 15 for producing artemisinin or completing the synthesis of artemisinin, and
- optionally a collection flask 18 for collecting the artemisinin containing solution from at least one reactor 15.

Suitable light sources are described below in detail. The mixing device is preferably a T-mixer valve. The solution of dihydroartemisinic acid preferably contains at least one photosensitizer which are in detail described below. The mixing device is preferably located upstream the reactor compartment, i.e. before the inlet of the reactor compartment. The feed for an acidic solution is downstream the reactor compartment, i.e. after the outlet of the reactor compartment. The reactor 15 is also located downstream the reactor compartment, i.e. after the outlet of the reactor compartment. The reactor 15 is connected to the reactor compartment and can be arranged downstream the feed for an acidic solution or the feed for an acidic solution goes into said reactor 15. The collection flask 18 is connected to the reactor 15 or if present to the reactor 16 which is then connected to the reactor 15 or if a third reactor 17 is present, the collection flask 18 is then connected to the reactor 17 which is connected to reactor 16 which is connected to reactor 15. Most preferably the above continuous flow reactor further comprises a back-pressure regulator 14 in order to perform at least the photooxidation reaction [step i)] under pressure. This back-pressure regulator 14 can be positioned at the end or at the outlet of the reactor compartment, or at the outlet of the photochemical reactor, or before the feed for an acidic solution, or after the reactor 15, or if present after the reactor 16, or if present after the reactor 17, or if present after the collection flask 18. In addition one or more further pressure regulators 14a/14b/14c might be positioned at the afore-mentioned positions before the back-pressure regulator 14.

As used herein the term "before" means upstream the reaction flow and the term "after" means downstream the reaction flow. The reaction flow is, of course, from the feed of the starting materials to the artemisinin as final product.

As defined herein the "back-pressure regulator 14" is the last pressure regulator downstream in the continuous flow reactor.

Thus, the afore-mentioned continuous flow reactor might further comprise
- a second reactor 16 downstream to the first reactor 15 or
- a second reactor 16 downstream to the first reactor 15 and a third reactor 17 downstream to the second reactor 16.

Most preferably, the continuous flow reactor further comprises a back-pressure regulator 14 downstream to the reactor 15 or downstream to the reactor 16 or downstream to the reactor 17 and most preferably downstream to the last reactor of the reactors 15, 16 (if present) and 17 (if present). Thus it is preferred that after the last reactor the back-pressure regulator 14 is located so that all reaction steps i)-iii) can be performed under pressure. Thus in this case the whole continuous flow reactor is operated under pressure and preferably under oxygen pressure. In addition or instead of the back-pressure regulator 14 other pressure regulators 14a (in case of one additional pressure regulator 14a; in case of a second 14a and 14b, in case of a third 14a, 14b and 14c, and so forth) can be present within the continuous flow reactor which are preferably placed after (i.e. downstream) the reactor compartment or after (i.e. downstream) the photochemical reactor and/or after (i.e. downstream) the feed for an acidic solution and/or after (i.e. downstream) the reactor 15 and/or after (i.e. downstream) the reactor 16 (if present) and/or after (i.e. downstream) the reactor 17 (if present) and/or after (i.e. downstream) the collection flask 18 (if present).

By introduction of other pressure regulators 14a/14b/14c preferably between different reactors of the continuous flow reactor, wherein in each different reactions for the conversion of dihydroartemisinic acid to artemisinin take place, it is possible to run each different reaction at a specific, adjustable pressure, preferable oxygen pressure. It is clear to the skilled person that the initial pressure in the continuous flow may be the highest in the whole reactor which decreases over the length of the reactor or with the reaction steps i), ii) and iii). Such a decrease of pressure may occur steadily or in steps by adjusting the other pressure regulators 14a/14b/14c accordingly, if present. 14a/14b/14c means 14a or 14a and 14b or 14a and 14b and 14c, i.e. one additional pressure regulator is present or two or three additional pressure regulators are present. The additional pressure regulators 14a/14b/14c are in addition to the back-pressure regulator 14 which is downstream the last pressure regulator. In case an oxygen tank 4 is used as oxygen source, this oxygen tank 4 has of course a manometer 3 for pressure regulation. However this manometer 3 is not counted as a pressure regulator 14a/14b/14c. However, the continuous flow reactor of the present invention may also be designed that by corresponding setting of the pressure regulators it may occur a higher pressure in a middle compartment or at the end of the reactor in comparison to the initial pressure at the inlet of the photochemical reactor. In order to have a freely adjustable pressure, preferably an oxygen pressure, more than one high pressure gas sources, e.g. for oxygen, for oxygen mixtures such as air, or other gases such as nitrogen or non-oxygen containing gas mixture, may be incorporated into the continuous flow reactor of the present invention. In a preferred embodiment of the present invention the continuous flow reactor is designed such that different pressures, preferably oxygen pressures (such as pure oxygen partial pressure and air partial pressure), being precisely adjustable can be applied for the photooxidation of dihydroartemisinic acid with singlet oxygen, for the acid mediated Hock cleavage and for the oxidation with triplet oxygen, even in case all three reactions are performed in a continuous manner.

Also in the preferred case the entire production of artemisinin from dihydroartemisinic acid is performed in a continuous manner under increased pressure from the initial gas inlet to e.g. a back pressure regulator 14 at the end of a first reactor 15 or a second reactor 16 or a third reactor 17 or even the collection flask 18, the pressure may drop steadily over the length of the reactor, especially in case the reactor in mainly a tubing 7.

Thus, in especially preferred embodiments of the continuous flow reactor of the present invention the continuous flow reactor comprises a back pressure regulator 14. These embodiments may further comprise additional pressure regulators 14a/14b/14c. One, two, three, four, five or more additional pressure regulators can be present. In case further pressure regulators are present, they are positioned at places different from the position of the back pressure regulator 14. Thus it is possible but not preferred that two pressure regulators are at the same position. In case two pressure regulators are present, namely 14 and 14a, the pressure regulator 14a is preferably positioned after the photochemical reactor or the reactor compartment and before the feed for the acidic solution and the back pressure regulator 14 after the reactor wherein the triplet oxygen oxidation is performed and if present before the collection flask 18. Alternatively, in case two pressure regulators are present, namely 14 and 14a, as well as a first reactor 15 it is specifically preferred that the pressure regulator 14a is positioned before the first reactor 15 which is positioned before the back pressure regulator 14 which is positioned, if present, before the collection flask 18. In case three pressure regulators are present, namely 14, 14a and 14b, the pressure regulator 14a is preferably positioned after the photochemical reactor or the reactor compartment and before the feed for the acidic solution, the pressure regulator 14b after the reactor 15 and before the reactor wherein the triplet oxygen oxidation is performed and the back pressure regulator 14 after the reactor wherein the triplet oxygen oxidation is performed and if present before the collection flask 18. Alternatively, in case three pressure regulators are present, namely 14, 14a and 14b, as well as a first reactor 15 and a second reactor 16 it is specifically preferred that the pressure regulator 14a is positioned before the first reactor 15 which is positioned before the pressure regulator 14b which is positioned before the second reactor 16 which is positioned before the back pressure regulator 14 which is positioned, if present, before the collection flask 18.

In case four pressure regulators are present, namely 14, 14a, 14b and 14c, the pressure regulator 14a is preferably positioned after the photochemical reactor or the reactor compartment and before the feed for the acidic solution, the pressure regulator 14b after the reactor 15 and before the reactor 16, the pressure regulator 14c after the reactor 16 and before the reactor 17, and the back pressure regulator 14 after the reactor 17 and if present before the collection flask 18. Thus it is especially preferred that one pressure regulator is positioned after the photochemical reactor or the reactor compartment and before the feed for the acidic solution and that another pressure regulator is positioned before the reactor wherein the triplet oxygen oxidation is performed and a third pressure regulator after the reactor wherein the triplet oxygen oxidation is performed so that at least the photooxidation with singlet oxygen and also the oxidation with triplet oxygen can be performed under pressure. In such embodiment the pressure for the oxidation with singlet oxygen is generated by the oxygen source, preferably an oxygen tank 4 with a manometer 3 and the pressure for the oxidation with triplet oxygen is generated by another oxygen source which could also be an oxygen tank with a manometer or just air introduced into the reactor under pressure. Alternatively, in case four pressure regulators are present, namely 14, 14a, 14b and 14c, as well as a first reactor 15 and a second reactor 16 and a third reactor 17 it is specifically preferred that the pressure regulator 14a is positioned before the first reactor 15 which is positioned before the pressure regulator 14b which is positioned before the second reactor 16 which is positioned before the pressure regulator 14c which is positioned before the third reactor 17 which is positioned before the back pressure regulator 14 which is positioned, if present, before the collection flask 18. In a further especially preferred embodiment the pressure over the whole continuous flow reactor or the pressure for the reaction steps i), ii) and iii) is generated by the oxygen source. This does not necessarily lead to an identical pressure for all three reaction steps, because the pressure drops over the components of the continuous flow reactor. However in this especially preferred embodiment the highest pressure is used for the photooxidation reaction while the pressure is dropped when performing the acidic cleavage and is probably dropped again when performing the triplet oxygen oxidation. However these pressure drops might be small and might be in a range of 10 hPa to 10000 hPa, preferably in the range from 100 hPa to 6000 hPa, more preferably in the range from 500 hPa to 5000 hPa and still and more preferably in the range from 1000 hPa to 4000 hPa.

The pressure drop over the length of the tubing 7 depends on various parameters and can be calculated in the laminar flow regime by the following formula $$\Delta p = \frac{8\mu L q}{\pi r^4},$$

whereby $\mu$ is the dynamic viscosity of the solvent, L is the length of the tubing, q the volumetric flow rate and r the inner radius of the tube.

Taking into account the roughness of the tube the actual pressure drop is higher. However, depending on the length of the reactor and the density of connections between reactor parts it is well possible to uphold an increased pressure over the entire length over the reactor, even in case for an embodiment wherein the whole conversion of dihydroartemisinic acid to artemisinin is performed continuously and under increased pressure from the oxygen or gas feed up to the final back pressure regulator 14.

Accordingly, in one embodiment for the continuous flow reactor with a reactor setup as given in example 12 comprising a back pressure regulator 14 set to 8 bar being attached to the exit of the reactor, a pressure within the reactor is established of about 10-12 bar after the pumping unit and before entering the photochemical reactor. In such embodiment the pressure drop of the whole reactor system is about 2-4 bar.

However, by introduction of pressure regulator 14a between the pumping unit and the back pressure regulator it is possible to change the profile of the pressure drop within the reactor and adjust the respective pressure to the different reactions taking place.

In a preferred embodiment of the present invention the photooxidation of step i) is carried out under pressure. In a very preferred embodiment of the present invention the reaction steps i), ii) and iii) are conducted or carried out under pressure. Thus the photooxidation with singlet oxygen, the acid mediated cleavage and the oxidation with triplet oxygen are preferably performed under a pressure of above 8000 hPa, more preferably above 10000 hPa and still more preferably above 12000 hPa. The photooxidation reaction with singlet oxygen [step i)] is preferably carried out under pressure of 5000 hPa-50000 hPa, preferably 7000 hPa-40000 hPa, more preferably 8000 hPa-30000 hPa, still more preferably 9000 hPa-25000 hPa, still more preferably 10000 hPa-20000 hPa, still more preferably 11000 hPa-19000 hPa, still more preferably 12000 hPa-18000 hPa, still more preferably 13000 hPa-17000 hPa, and most preferably 14000 hPa-16000 hPa. The acid mediated cleavage is preferably performed under a pressure of 1000 hPa-15000 hPa, more preferably 2000 hPa-14000 hPa, more preferably 3000 hPa-13000 hPa, more preferably 4000 hPa-12000 hPa, more preferably 5000 hPa-11000 hPa, more preferably 6000 hPa-10000 hPa, and still more preferably 7000 hPa-9000 hPa. The oxidation with triplet oxygen is preferably conducted at a pressure of 1000 hPa-15000 hPa, more preferably of 2000 hPa-14000 hPa, more preferably of 3000 hPa-13000 hPa, more preferably of 4000 hPa-12000 hPa, more preferably of 5000 hPa-11000 hPa, more preferably of 6000 hPa-10000 hPa, and most preferably of 7000 hPa-9000 hPa.

The initial pressure with which the oxygen is fed into the system for generating the singlet oxygen is preferably between 8000 hPa and 15000 hPa and more preferably between 9000 hPa and 14000 hPa, and most preferably between 10000 hPa and 13000 hPa. The pressure drop over the three steps i), ii) and iii) is preferably between 1000 hPa and 10000 hPa, more preferably between 1500 hPa and 6000 hPa and still more preferably between 2000 hPa and 4000 hPa.

Thus, the continuous flow reactor of the present invention preferably comprises or consists of:
 a light source 11,
 a mixing device for mixing oxygen with a solution of dihydroartemisinic acid,
 a reactor compartment exposed to the light source for performing the photooxidation,
 pressure regulator 14a
 at least one reactor 15, and
 a back-pressure regulator 14.

The continuous flow reactor of this embodiment may further comprise a collection flask 18 for collecting the artemisinin containing solution or a device for continuous separation of artemisinin (6).

In a preferred embodiment of the present invention the device for continuous separation of artemisinin (6) can be simulated moving bed chromatography columns or reactor parts for continuous crystallization.

Also, the continuous flow reactor of the present invention preferably comprises or consists of:
 a light source 11,
 a mixing device for mixing oxygen with a solution of dihydroartemisinic acid,
 a reactor compartment exposed to the light source for performing the photooxidation,
 pressure regulator 14a,
 one reactor 15,
 pressure regulator 14b,
 a second reactor 16,
 pressure regulator 14c,
 a third reactor 17, and
 a back-pressure regulator 14.

The continuous flow reactor of this embodiment may further comprise a collection flask 18 for collecting the artemisinin containing solution or a device for continuous separation of artemisinin (6).

In a preferred embodiment of the present invention the device for continuous separation of artemisinin (6) can be simulated moving bed chromatography columns or reactor parts for continuous crystallization.

Also, the continuous flow reactor of the present invention preferably comprises or consists of:
 a light source 11,
 a mixing device for mixing oxygen with a solution of dihydroartemisinic acid,
 a reactor compartment exposed to the light source for performing the photooxidation, pressure regulator 14a,
a feed for an acidic solution,
one reactor 15,
pressure regulator 14b,
a second reactor 16,
pressure regulator 14c,
a third reactor 17, and
a back-pressure regulator 14.

The continuous flow reactor of this embodiment may further comprise a collection flask 18 for collecting the artemisinin containing solution or a device for continuous separation of artemisinin (6).

In a preferred embodiment of the present invention the device for continuous separation of artemisinin (6) can be simulated moving bed chromatography columns or reactor parts for continuous crystallization.

Also, the continuous flow reactor of the present invention preferably comprises or consists of:
 a light source 11,
 a mixing device for mixing oxygen with a solution of dihydroartemisinic acid,
 a reactor compartment exposed to the light source for performing the photooxidation,
 pressure regulator 14a,
 a feed for an acidic solution,
 one reactor 15,
 pressure regulator 14b,
 a second reactor 16,
 a back-pressure regulator 14.

The continuous flow reactor of this embodiment may further comprise a collection flask 18 for collecting the artemisinin containing solution or a device for continuous separation of artemisinin (6).

In a preferred embodiment of the present invention the device for continuous separation of artemisinin (6) can be simulated moving bed chromatography columns or reactor parts for continuous crystallization.

Also, the continuous flow reactor of the present invention preferably comprises or consists of:
 a light source 11,
 a mixing device for mixing oxygen with a solution of dihydroartemisinic acid,
 a reactor compartment exposed to the light source for performing the photooxidation,
 pressure regulator 14a,
 a feed for an acidic solution,
 one reactor 15,
 a back-pressure regulator 14.

The continuous flow reactor of this embodiment may further comprise a collection flask 18 for collecting the artemisinin containing solution or a device for continuous separation of artemisinin (6).

In a preferred embodiment of the present invention the device for continuous separation of artemisinin (6) can be simulated moving bed chromatography columns or reactor parts for continuous crystallization.

Further, the continuous flow reactor of the present invention preferably comprises or consists of:
 a light source 11,
 a mixing device for mixing oxygen with a solution of dihydroartemisinic acid,
 a reactor compartment exposed to the light source for performing the photooxidation,
 a feed for an acidic solution,
 at least one reactor 15, and
 a back-pressure regulator 14.

The continuous flow reactor of this embodiment comprises one reactor 15 and may further comprise a collection flask 18 for collecting the artemisinin containing solution or a device for continuous separation of artemisinin (6) and optionally one further reactor 16 or optionally two further reactors 16 and 17. Moreover this embodiment may further comprise additional pressure regulators 14a/14b/14c.

Also, the continuous flow reactor of the present invention preferably comprises or consists of:
 a light source 11,
 a mixing device for mixing oxygen with a solution of dihydroartemisinic acid,
 a reactor compartment exposed to the light source for performing the photooxidation,
 a feed for an acidic solution,
 at least one reactor 15,
 a back-pressure regulator 14, and
 a device for continuous separation of artemisinin (6).

In a preferred embodiment of the present invention the device for continuous separation of artemisinin (6) can be simulated moving bed chromatography columns or reactor parts for continuous crystallization. This embodiment comprises one reactor 15 and may further comprise a collection flask 18 for collecting the artemisinin containing solution or a device for continuous separation of artemisinin (6) and optionally one further reactor 16 or optionally two further reactors 16 and 17. Moreover this embodiment may further comprise additional pressure regulators 14a/14b/14c.

In another preferred embodiment of the present invention the continuous flow reactor comprises or consists of:
 a light source 11,
 a mixing device for mixing oxygen with a solution of dihydroartemisinic acid,
 reactor compartment exposed to the light source for irradiating the mixture of dihydroartemisinic acid and oxygen when the mixture passes the reactor compartment,
 at least one reactor 15, and
 a back-pressure regulator 14.

The continuous flow reactor of this embodiment may further comprise a collection flask 18 for collecting the artemisinin containing solution or a device for continuous separation of artemisinin (6). This embodiment comprises one reactor 15 and may further comprise a collection flask 18 for collecting the artemisinin containing solution or a device for continuous separation of artemisinin (6) and optionally one further reactor 16 or optionally two further reactors 16 and 17. Moreover this embodiment may further comprise additional pressure regulators 14a/14b/14c. In this preferred embodiment of the present invention the device for continuous separation of artemisinin (6) can be simulated moving bed chromatography columns or reactor parts for continuous crystallization.

Yet in another preferred embodiment of the present invention the continuous flow reactor comprises or consists of:
 a light source 11,
 a mixing device for mixing oxygen with a solution of dihydroartemisinic acid,
 reactor compartment for carrying out the photooxidation and which is at least partially irradiated by the light source and which has at least one inlet for the solution of dihydroartemisinic acid and oxygen and at least one outlet for the solution after the photooxidation,
 at least one reactor 15, and
 a back-pressure regulator 14.

The continuous flow reactor of this embodiment may further comprise a collection flask 18 for collecting the artemisinin containing solution or a device for continuous separation of artemisinin (6). This embodiment comprises one reactor 15 and may further comprise a collection flask 18 for collecting the artemisinin containing solution or a device for continuous separation of artemisinin (6) and optionally one further reactor 16 or optionally two further reactors 16 and 17. Moreover this embodiment may further comprise additional pressure regulators 14a/14b/14c. In this preferred embodiment of the present invention the device for continuous separation of artemisinin (6) can be simulated moving bed chromatography columns or reactor parts for continuous crystallization.

Even yet in another preferred embodiment of the present invention the continuous flow reactor comprises or consists of:
- a light source 11,
- a mixing device for mixing oxygen with a solution of dihydroartemisinic acid,
- reactor compartment for irradiation of the solution of dihydroartemisinic acid and the oxygen by the light source when the solution flows through the reactor compartment,
- at least one reactor 15, and
- a back-pressure regulator 14.

The continuous flow reactor of this embodiment may further comprise a collection flask 18 for collecting the artemisinin containing solution or a device for continuous separation of artemisinin (6). This embodiment comprises one reactor 15 and may further comprise a collection flask 18 for collecting the artemisinin containing solution or a device for continuous separation of artemisinin (6) and optionally one further reactor 16 or optionally two further reactors 16 and 17. Moreover this embodiment may further comprise additional pressure regulators 14a/14b/14c. In this preferred embodiment of the present invention the device for continuous separation of artemisinin (6) can be simulated moving bed chromatography columns or reactor parts for continuous crystallization.

Still yet in another preferred embodiment of the present invention the continuous flow reactor comprises or consists of:
- a light source 11,
- a mixing device for mixing oxygen with a solution of dihydroartemisinic acid,
- reactor compartment being at least partially irradiated by the light source and having an inlet for the mixture of dihydroartemisinic acid and oxygen on its one end and an outlet for the reacted products on the opposite end,
- at least one reactor 15, and
- a back-pressure regulator 14.

The continuous flow reactor of this embodiment may further comprise a collection flask 18 for collecting the artemisinin containing solution or a device for continuous separation of artemisinin (6). This embodiment comprises one reactor 15 and may further comprise a collection flask 18 for collecting the artemisinin containing solution or a device for continuous separation of artemisinin (6) and optionally one further reactor 16 or optionally two further reactors 16 and 17. Moreover this embodiment may further comprise additional pressure regulators 14a/14b/14c. In this preferred embodiment of the present invention the device for continuous separation of artemisinin (6) can be simulated moving bed chromatography columns or reactor parts for continuous crystallization.

Moreover the continuous flow reactor preferably further comprises an oxygen source capable of providing oxygen above atmospheric pressure. Such oxygen source is preferably an oxygen tank 4 with a manometer 3.

An important component of the continuous flow reactor in the reactor compartment is in a preferred embodiment a tubing 7. Such a tubing 7 is preferably wrapped in multiple loops, or wrapped around a transparent support which does not hinder the light to go through so that all parts of the loops or all parts of the tubing 7 is exposed to the light of the light source or is wrapped around the light source.

In another preferred embodiment the tubing 7 consists of a plurality of transparent plates such as glass plates arranged over each other between which the solution or mixture of dihydroartemisinic acid flows while being exposed to the light of the light source.

In a still further preferred example the tubing 7 is in the form of a cylinder or a double-walled cylinder arranged around the light source and the solution or mixture of dihydroartemisinic acid flows through that cylinder or within the walls of the doubled-walled cylinder while being exposed to the light of the light source. One or more cooling cylinder might be present around the light source and/or around or within the cylinder or double-walled cylinder.

The reactor compartment is this part of the continuous flow reactor or more specific of the photochemical reactor, wherein the photooxidation is performed. Therefore, the reactor compartment refers to the part or the parts of the continuous flow reactor which is/are exposed to the light of the light source and through which the mixture or solution of dihydroartemisinic acid together with the oxygen flows and wherein the singlet oxygen is generated. Thus, the reactor compartment can be a tubing 7 or preferably comprises a tubing 7 which is exposed to the light of the light source and through which the mixture or solution of dihydroartemisinic acid together with the oxygen flows and wherein the singlet oxygen is generated. The reactor compartment is designed in a way that the tubing 7 is exposed to the light of the light source in the best possible manner. Preferably the reactor compartment has non-transparent outer walls or a non-transparent housing wherein the light source is located. The inner walls of the reactor compartment are preferably light reflecting so that as much as possible of the generated light of the light source can be used for the photooxidation.

In general, a reactor component as used herein refers to a section of the continuous flow reactor, from the feed of a certain starting material to the outlet of product, wherein certain actions or operations for the conversion of dihydroartemisinic acid (2) to artemisinin (6) take place and comprise all reactor parts which are involved in these actions or operations. The reactor compartment is therefore a specific form of a reactor component. If the continuous flow reactor is seen as a long sequence of different reactor parts which the starting materials alone or in a mixture pass along, section can almost be taken literally in that certain parts are figuratively cut out of the sequence and defined by their function to the reaction.

For example, reactor components of the continuous flow reactor of the present invention are reactor parts for the following actions:
- provision of the starting materials,
- mixing of the starting materials,
- irradiation of a solution of dihydroartemisinic acid, sensitizer, solvent and oxygen,
- mixing with acid,
- reaction of the acid for the Hock cleavage,
- oxidation with triplet oxygen for the formation of artemisinin.

According to the present invention a reactor component may comprise the physical reactor parts for more than one function for enabling the different reactions for the conversion of dihydroartemisinic acid (2) to artemisinin (6). One reactor component may only comprise these parts of the continuous flow reactor of the present invention where the Hock cleavage takes place. However, another reactor component may comprise all parts where the conversions take place that the material flow undergoes after the irradiation of the light source.

The reactor component of the continuous flow reactor for performing the photooxidation reaction is the reactor compartment with all reactor parts that are irradiated by the light source and having an inlet for the mixture of dihydroartemisinic acid and oxygen on its one end and an outlet for the reacted products on the opposite end. It is also possible that the photochemical reactor as defined herein with all different possible specifications may be a reactor compartment of the continuous flow reactor of the present invention.

Thus the term "reactor compartment" refers to the reactor parts that are irradiated by the light source. Within the reactor compartment the photooxidation reaction with singlet oxygen is performed under irradiation by the light source. Thus the mixture of solvent, dihydroartemisinic acid, photosensitizer and oxygen flows through the reactor compartment wherein the photooxidation reaction with singlet oxygen [step i)] is performed. The reactor compartment through which the mixture flows which is exposed to the light of the light source has the form of a tube, coil, cylinder, double-wall cylinder, multi-walled cylinder, tubing, duct, pipe, spiral, helix, spiral coil, zig-zag coil, board, fluidized bed, multi-layered fluidized bed, pool, vessel, tank, basin or the like. The reactor compartment has a form so that the mixture to be irradiated which flows through the reactor compartment is almost all the time exposed to the light of the light source when flowing through the reactor compartment.

According to the continuous flow reactor of the present invention the reactor compartment may adopt any suitable shape, preferably those specified above wherein the mixture of solvent, dihydroartemisinic acid, photosensitizer and oxygen can be well irradiated, preferably with a high surface area. For example, in case of a multi-walled cylinder different cylinders can be arranged around the at least one light source in the middle of the assembly which are preferably made of glass, more preferably of pressure proof glass, such that the light can easily be irradiated without significant loss of intensity on the solution running through the cylinder which can further be processed under increased pressure, preferably oxygen pressure. Particularly, in a doubled-walled or multiple-walled cylinder the solution or mixture of dihydroartemisinic acid flows more than once past the light source and experiences an increased retention time. Also, between the walls or at one side of and/or around or within one cylinder a cooling cylinder may be incorporated. Also, a second light source can be incorporated at the circumference of the cylinder. Such assembly may also be adapted for spiral, helix, spiral coil or zig-zag coil, wherein these coil reactors are arranged around or in vicinity to the light source. Also, those coils are preferably made of glass or any other suitable transparent material. Also, the reactor compartment may consist of or comprise a plane board, fluidized bed or a multi-layered fluidized bed e.g. in the form of multiple layers of glass or any suitable transparent polymer assembled vertically over each other, whereon or where in between the layers the mixture of solvent, dihydroartemisinic acid, photosensitizer and oxygen can flow, and can be irradiated. In case of a multi-layered fluidized bed two consecutive layers are connected to each other intermittently at alternating ends such that the layers form a serpentine assembly in a cross-section view. In such an assembly the mixture of solvent, dihydroartemisinic acid, photosensitizer and oxygen can be well irradiated from below and/or above while flowing through the gaps of the fold-like glass layer assembly. In such an assembly one or more cooling systems can be incorporated at the bottom, the top and/or at the sides of the compartment.

The reactor compartment may also be a pipe, duct, pool, tank, basin or vessel through which the mixture of solvent, dihydroartemisinic acid, photosensitizer and oxygen flows from the inlet to the outlet, and wherein the light source is immersed into the solution such that the mixture of solvent, dihydroartemisinic acid, photosensitizer and oxygen flows along the light source; the light source preferably comprising a cooling cylinder.

Thus the function of the reactor compartment is to expose the mixture flowing through that reactor compartment as much and as long as possible to the light source for irradiating the mixture of dihydroartemisinic acid, photosensitizer and oxygen.

According to the present invention there may also be reactor compartments specifically designed for certain embodiments of the continuous flow reactor. For example, for the immersion well assembly, there may be a reactor compartment
- for irradiating the mixture of dihydroartemisinic acid and oxygen having an immersion well and a filter, or
- for carrying out the photooxidation having an inlet to the immersion well for a mixture of dihydroartemisinic acid and oxygen and an outlet from the immersion well,
- comprising tubing 7 being wrapped around the immersion well and being exposed to the light source for performing the photooxidation.

For the box assembly there may be a reactor compartment
- in the form of a tubing 7 being wrapped around a transparent plate, wherein the reactor compartment is exposed to the light source for performing the photooxidation,
- in the form of a tubing 7 being wrapped around a transparent plate being at least partially irradiated by the light source and having an inlet for the mixture of dihydroartemisinic acid and oxygen on its one end and an outlet for the reacted products on the opposite end.

For the cooled box assembly there may be a reactor compartment
- in the form of a tubing 7 being wrapped around a transparent plate having an inlet for the mixture of dihydroartemisinic acid and oxygen on its one end and an outlet for the reacted products on the opposite end, wherein the transparent plate with the wrapped tubing is immersed into a cooling liquid,
- in the form of a tubing 7 being wrapped around a transparent plate being at least partially irradiated by the light source.

For the cylinder assembly there may be a reactor compartment
- in the form of a transparent cylinder being positioned around a light source having an inlet for the mixture of dihydroartemisinic acid and oxygen on its one end and an outlet for the reacted products,
- in the form of a multiple-walled cylinder while being exposed to the light of the light source, wherein the mixture of dihydroartemisinic acid and oxygen flows between the walls and wherein the walls are made of transparent material and wherein the mixture of dihydroartemisinic acid and oxygen is exposed to the light of the light source in each gap between the walls of the multiple-walled cylinder.

Thus, for example one aspect of the present invention is directed to a continuous flow reactor comprising or consisting of:
- a light source 11,
- a mixing device for mixing oxygen with a solution of dihydroartemisinic acid,
- a reactor compartment in the form of a tubing 7 or in form of transparent plates arranged over each other or in form of a cylinder or double-walled cylinder, wherein the reactor compartment is exposed to the light source for performing the photooxidation,
- a feed for an acidic solution,
- at least one reactor 15,
- a back-pressure regulator 14, and
- a collection flask 18 for collecting the artemisinin containing solution.

Also preferred is the reactor component which comprises a reactor compartment in the form of a tubing 7 in a box which is impervious to light with light reflecting inner walls and one opening through which the tubing 7 enters the box and another opening through which the tubing 7 leaves the box and multiple loops of the tubing 7 are arranged in the inside of the box, wherein the tubing 7 has an inlet for a mixture of dihydroartemisinic acid and oxygen on its one end before entering the box and an outlet for the reacted products on the opposite end after leaving the box.

Moreover it is preferred that continuous flow reactor further comprises a cooling liquid and/or a chiller. The cooling liquid and/or the chiller shall cool the solution or mixture of dihydroartemisinic acid during the photooxidation.

Another preferred embodiment of the present invention is directed to a method for producing artemisinin (6) from dihydroartemisinic acid (2) comprising or consisting of the following steps:

A) providing dihydroartemisinic acid (2) represented by the following formula

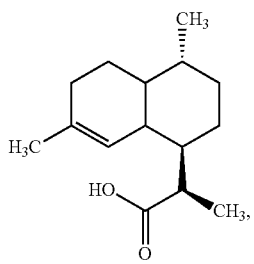

(2)

B) performing the following reactions
i) photooxidation of dihydroartemisinic acid (2) with singlet oxygen in a continuous manner in a photochemical reactor,
ii) followed by an acid mediated cleavage and
iii) subsequent oxidation with triplet oxygen in order to obtain artemisinin (6) of the following formula:

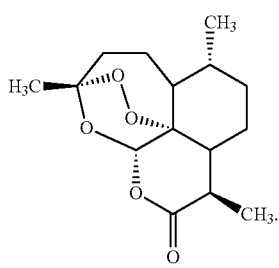

(6)

In case a chemical synthesis of dihydroartemisinic acid (2) is desired, dihydroartemisinic acid (2) can be prepared by reducing artemisinic acid (1). Thus, dihydroartemisinic acid (2) can be obtained by reducing artemisinic acid (1) of the following formula

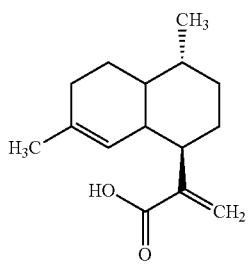

(1)

to dihydroartemisinic acid (2).

Thus the present invention is also directed to a method for producing artemisinin (6) from artemisinic acid (1) comprising the following steps:

A) providing artemisinic acid (1) represented by the following formula

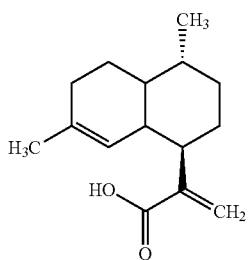

(1)

B) reducing artemisinic acid (1) to dihydroartemisinic acid (2) of the following formula

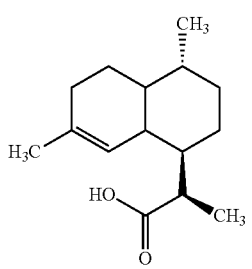

(2)

C) performing the following reactions
i) photooxidation of dihydroartemisinic acid (2) with singlet oxygen in a continuous manner in a photochemical reactor,
ii) followed by an acid mediated cleavage and
iii) subsequent oxidation with triplet oxygen in order to obtain artemisinin (6) of the following formula:

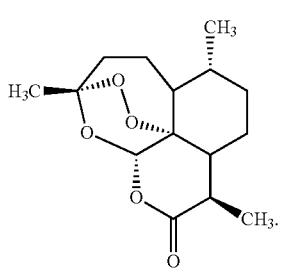

(6)

In this embodiment the photooxidation is performed continuously in the photochemical reactor which is a component of the continuous flow reactor. The acid mediated cleavage [step ii)] as well as the oxidation with triplet oxygen [step iii)] can be performed in a batch process or in a semi-continuous manner or preferably also in a continuous manner.

Further it is preferred that oxygen for the provision of singlet oxygen is provided to the continuous flow reactor above atmospheric pressure. Thus it is preferred if the photooxidation is performed under pressure and especially under oxygen pressure. It is more preferred if the oxidation with singlet oxygen and also the oxidation with triplet oxygen are performed under pressure and especially under oxygen pressure. It is most preferred if all three steps i)-iii) are performed under pressure and especially under oxygen pressure while the pressure can be different for each step or can be diminished during one step.

In all methods according to the present invention is it preferred that the continuous flow reactor comprises a tube or tubing made of a fluorinated or perfluorinated alkylene polymer wherein the photooxidation of dihydroartemisinic acid takes place. It may also be preferred that the tubing is wrapped around a photochemical reactor containing the light source.

The photooxidation of dihydroartemisinic acid (2) generally results in the intermediate products (3), (4) and (5) as also described in example 1. The main intermediate product is the hydroperoxide (3) which can be obtained by the process of the present invention in at least 75% yield, preferably in at least 80% yield and more preferably in at least 84% yield. In order to perform subsequent reactions such as the further preparation of artemisinin (6), preferably also in a continuous manner, it is not required to purify the obtained hydroperoxide (3) or to remove the intermediate products (4) and (5) as shown in example 1.

The hydroperoxide (3) of the following formula

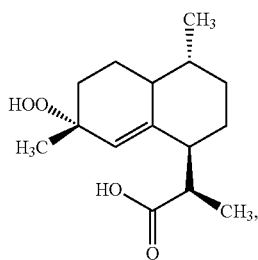

the hydroperoxide (4) of the following formula

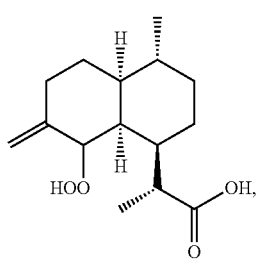

and the hydroperoxide (5) of the following formula

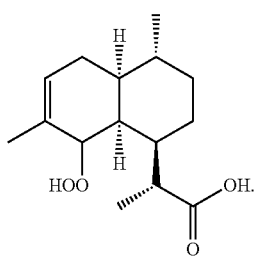

are formed as photooxidation products from the reaction of dihydroartemisinic acid (2) with singlet oxygen according to the present invention.

As also described above, dihydroartemisinic acid (2) can be prepared from artemisinic acid (1). The starting material artemisinic acid (1) which is also known as arteannuic acid and which has the chemical name 2-[(1R,4R,4aS,8aR)-4,7-dimethyl-1,2,3,4,4a,5,6,8a-octahydronaphthalen-1-yl]prop-2-enoic acid can be obtained synthetically, by recombinant methods or can be isolated from the plant *Artemisia annua*. Since there is artemisinic acid and dihydroartemisinic acid contained in the plant *Artemisia annua*, an efficient method to convert artemisinic acid (1) and dihydroartemisinic acid (2) into the hydroperoxide (3) and subsequently to artemisinin (6) is desired. Thus the starting material artemisinic acid (1) or dihydroartemisinic acid (2) can be used as a plant extract in all reactor embodiments disclosed herein. Also, extraction protocols to remove artemisinic acid and dihydroartemisinic acid from *artemisia annua* have been published (Wallaart, T. E. et al., *J. Nat. Prod.* 1999, 62, 430-433), making use of the extraction of acidic compounds by aqueous base and the reextraction into an organic phase after acidification.

An adapted procedure can be applied to such mother liquor remaining after removal of artemisinin from *artemisia annua* extracts. Thus, also the extract of *artemisia annua* after the removal of artemisinin can be readily used as starting material in all reactor embodiments disclosed herein. Therein the method of the present invention provides a possibility of sophistically using waste material of industrial scale.

Also, in order to overcome drawbacks of photochemical reactions being performed in batch-like manner in the prior art, the inventors designed a continuous flow set-up which in contrast to said batch processes allows the production of large quantities of desired material by simply extending the run time rather than changing to larger reaction vessels. The continuous flow process of the present invention provides a highly complex natural product from a much less complex molecule that can be isolated in larger quantities or can be readily produced in yeast. The efficiency, simplicity and productivity of the approach will provide access to much needed medication against malaria.

The methods of the present invention allow the synthesis of artemisinin, wherein 12.5 mmol dihydroartemisinic acid are processed in a total residence time below 5 minutes through the continuous flow reactor in order to yield preferably at least 39% artemisinin of a purity above 95%.

Excellent control over reaction parameters such as reaction time, temperature and mixing are hallmarks of flow chemistry and thus also provided by the method, the photochemical reactor and the continuous flow reactor according to the present invention.

Photochemical transformations according to the present invention greatly benefit from the flow regime as the penetration depth of the light remains almost the same also during scale-up due to the dimensions of tubing that serves as reaction vessel.

Thus, the significant disadvantages of the prior art were addressed by the present invention and were solved in a way that at least the photooxidation of dihydroartemisinic acid (2), but also subsequent steps starting from dihydroartemisinic acid (2) could be combined in a continuous flow system which can be easily controlled, easily scaled up, optimized to produce good yields and does not require the isolation and purification of any intermediates. Such advantages can not be provided by a batch-reaction of dihydroartemisinic acid (2) with singlet oxygen, and also optional subsequent continuous conversions to yield artemisinin (6) as described herein.

In one embodiment of the invention the photochemical reactor comprises an assembly wherein the solution of dihydroartemisinic acid (2) and oxygen running through the tubing which is wrapped around the filter, the light source and the immersion well of the photochemical reactor while this solution is irradiated by the light source. The outflow from the tubing can be processed in three different ways, namely in a batch process, or in a separate continuous flow process, or in a continued continuous flow process. In the following this setup of a photochemical continuous flow reactor is called the "immersion well assembly".

In another preferred embodiment of this invention the photochemical reactor comprises an assembly wherein the solution of dihydroartemisinic acid (2) and oxygen is running through a tubing, wherein the photooxidation of dihydroartemisinic acid (2) takes place, and which is wrapped around a transparent body, which is placed inside a box, whereby the box also contains a light source. This box is like a "black box" and does not allow light to enter into or to leave the box. Thus the box is made of lightproof or opaque material and thus is impervious to light. The inner surfaces of the box are covered with light sources or with reflecting materials such as mirrors or aluminum foil. In another preferred embodiment the box is made of a reflective material such as aluminum or stainless steel. There are only two small holes in the box through which the tube for performing the photochemical reaction of dihydroartemisinic acid (2) with singlet oxygen enters and leaves the box. In the following, the described box setup of a photochemical continuous flow reactor is called the "box assembly". In another preferred embodiment the box assembly further comprises a cooling system wherein the photooxidation reaction occurs in a light proof box and the reactor can be cooled. In the following such a box setup of a photochemical continuous flow reactor is called the "cooled box assembly". Yet in another preferred embodiment of the present invention the reaction mixture may also flow over a broad transparent plate thereby transforming the volume of the liquid into a thin film which is irradiated by a light source through the transparent plate. In particular when irradiation occurs over a sufficient length of the formed film the residence time can significantly be decreased. The transparent plate can be fixed to a second plate leaving a gap between first and second plate for the liquid to flow. The second plate be made of a reflective material and further may be cooled. In the following such a setup of a photochemical continuous flow reactor is called the "falling film assembly".

Still in another embodiment the reaction mixture max also flow through the tubing 7 in the form of a cylinder or a double-walled cylinder arranged around the light source and the solution or mixture of dihydroartemisinic acid flows through that cylinder or within the walls of the doubled-walled cylinder while being exposed to the light of the light source. One or more cooling cylinder might be present around the light source and/or around or within the cylinder or double-walled cylinder. In the following such a setup of a photochemical continuous flow reactor is called the "cylinder assembly".

GENERAL TEACHINGS

The following general teachings are preferred embodiments which apply to all methods, photochemical reactors and continuous flow reactors disclosed herein if the teachings are not made in regard to a specific embodiment.

Suitable light sources for all herein described assembled reactors comprise Hg lamps, neon lamps, light bulbs and light-emitting diodes (LED).

Further, the photochemical reactor of the immersion well assembly, the box assembly and the cooled box assembly comprises a setup which consists of a tube made of a fluorinated or perfluorinated alkylene polymer, wherein the photooxidation of dihydroartemisinic acid (2) takes place. Such a polymer may be FEP (fluorinated ethylene propylene copolymer). However, also other polymers may be used for tubing such as ETFE (ethylene tetrafluoroethylene), ECTFE (ethylene chlorotrifluoroethylene), PFA (perflouroalkoxyalkane), PEI (polyetherimide), PPSF (polyphenylsulfone), PC (polycarbonate), PMMA (polymethyl methacrylate), PE (polyethylene) or PP (polypropylene). Any other materials that are transparent and resistant to the solvent and reagents such as silica tubing may also be used.

In case of the box assembly and the cooled box assembly the tubing is wrapped around a transparent body, which is placed inside a box, whereby the inside of the box also contains at least one light source.

In a preferred embodiment of the invention the light source of the box assembly and the cooled box assembly is a light-emitting diode, or even more preferred an assembly of light-emitting diodes. The light-emitting diodes have a preferred light emitting wavelength of 420 nm and/or 660 nm. Such an assembly of light-emitting diodes is preferably arranged in a plane module. As light source of the box assembly and the cooled box assembly there can be used only one of those modules. However, it is also possible to increase the number of modules or to increase the number of diodes and thereby the dimensions of the modules. The number of modules is not particularly limited as this number highly dependents on the dimensions of the reactor. In a preferred embodiment of the present invention the number of modules ranges from 1 to 100, more preferably from 1 to 50, and is most preferably 1.

In a more preferred embodiment of the invention the setup of light-emitting diodes is a plane module having an emission-surface within $0.5 \times 0.5$ cm$^2$ to $20 \times 20$ cm$^2$, or even more preferred of at least $2.5 \times 2.5$ cm$^2$.

In another preferred embodiment of the invention the setup of the arranged LED's are within a plane module having an emission-surface within $25 \times 120$ cm$^2$ to $50 \times 50$ cm$^2$, or even more preferred of at least $44 \times 88$ cm$^2$. The emission angle of the diodes ranges from 90° to 150°, and is preferably 120°.

Residence times for irradiation depend on the amount of feed being irradiated and the concentration of reactants as well as of the photosensitizer. Preferred residence times for the performance of the photooxidation in all reactor assemblies according to the present invention range from 5 seconds to 5 hours, preferably from 30 seconds to 30 minutes, more preferably 1 minute to 10 minutes and most preferably from 2 minutes to 5 minutes. One specifically preferred irradiation occurs for 2 minutes at an electrical output of 72 W.

The use of LEDs is particularly preferred for the present invention as the LEDs, preferably arranged in a module do not emit UV-radiation which would lead to undesired side reactions. In addition specific UV-light filters are not necessary.

Within the box assembly and the cooled box assembly containing the light source and the tubing wrapped around a transparent body, more than one module of light emitting diodes may be arranged around the wrapped tubing, containing the dihydroartemisinic acid (2) and the oxygen for the photooxidation reaction. In a preferred embodiment the box can also be any suitable containment being water proof and capable of keeping a certain amount of liquid such as a container, a bucket, a tray, a vessel or a bowl, preferably equipped with reflectors or with a reflecting surface on the inner wall. In a more preferred embodiment of the invention the inner walls of the box or containment containing the tubing and the light source, may consist of or have a light reflecting surface and/or the box containing the tubing and the light source may comprise reflectors, having a light reflecting surface, wherein the reflectors are arranged around the tubing and the light source.

In a preferred embodiment of the invention the light reflecting surface and/or the reflectors lead to a specular reflection of the light of the light source within the box.

The light reflecting surface and/or the reflectors comprise or contain an assembly or a material which belong to the group of: astro-foil, polished anodized aluminum, Mylar, metallized biaxially-oriented polyethylene terephthalate, aluminum foil, can lids, tinplate, acrylic mirror, glass mirror, metal mirror, ceramic mirror, glass-ceramic mirror, mirrors made out of Borofloat, Pyrex, Cervit, Sital, Zerodur, wherein the mirror is defined as a suitable substrate which is coated with a light reflective material. The substrate is preferably glass, ceramic or glass-ceramic, due to its transparency, ease of fabrication, rigidity, hardness, and ability to take a smooth finish. The reflective coating is typically applied to the back surface of the substrate, so that the reflecting side of the coating is protected from corrosion and accidental damage by the glass on one side and the coating itself and optional paint for further protection on the other. The reflective coating is made out of silver, aluminium or other reflecting metals. On the other hand the substrate may be made out of polished metal itself. For the cooled box assembly the main body containment is preferably made of aluminum or stainless steel. However, also other materials are suitable such as chromium, molybdenum, silver, gold, lead or alloys thereof.

In other words the light reflecting surface and/or the reflector may be made out of a light reflecting material which has a light reflectivity of at least >70%, or more preferably >90%, wherein the reflected light spectra comprises the wavelengths needed to perform the photooxidation reaction of dihydroartemisinic acid (2). In a preferred embodiment of the invention the reflected spectra in the box assembly contains the wavelengths of 420 nm and/or 660 nm.

According to the invention in all embodiments of reactors the use of photosensitizers is essential. All photosensitizer capable of promoting the generation of singlet oxygen could be used such as fullerenes, several transition metal complexes and semiconductors like titanium oxide and zinc oxide. Therefore, at least one photosensitizer is preferably added to the solution of dihydroartemisinic acid, which can be excited easily by light and transfers its energy to the dissolved oxygen. Many different known photosensitizers are suitable for this application; preferably the photosensitizers have at least one of the following features:

- a high extinction coefficient, so that a low concentration of photosensitizer can be used, making the process more cost-effective;
- a high quantum yield for singlet oxygen production, which means that a large amount of singlet oxygen can be produced per number of photons, making the process more energy efficient
- inertness, so that no undesired side-reactions e.g. with solvent or added reagents occurs;
- high photostability of the sensitizer, resulting in no decrease in yield over time;
- high target-selectivity in that the exited sensitizer transfers its energy selectively onto triplet oxygen and not onto other added reagents preventing the formation of side products;
- absorption at long wavelength in the visible range as these photons possess less energy, making the process more energy efficient;
- insensitivity towards acid facilitating an initial addition of the acid necessary to induce Hock cleavage.

Particularly suitable photosensitizer for use in a process according to the present invention are, for example: tetraphenylporphyrin, 5,10,15,20-tetrakis(pentafluorophenyl)porphyrin, tris(2,2'-bipyridyl)ruthenium(II), pheophytin a, pheophorbide a, 2,3,7,8-dibenzopyrene-1,6-quinone and metal-phthalocyanines.

However, also other photosensitizers are suitable for the photooxidation reaction of the present invention. Such photosensitizers can be zinc tetraphenylporphyrin or 9,10-dicyanoanthracene. In some embodiments the preferred photosensitizer is 9,10-dicyanoanthracene. In a preferred embodiment of the present invention the concentration of the photosensitizer ranges from 0.025 mM to 10 mM, more preferably from 0.05 to 9.0 mM, and most preferably from 0.75 to 2.5 mM.

For tetraphenylporphyrin, 9,10-dicyanoanthracene and zinc tetraphenylporphyrin is was found that good to excellent conversions of DHAA (2) to the hydroperoxide (3) in toluene can be achieved at already very low concentrations (FIG. 10B). Specifically, for tetraphenylporphyrin it is was found that with relatively low concentrations of TPP (0.05 mol %) a high conversion of dihydroartemisinic acid can be achieved. Further increase in the concentration slightly improves the yield. In a specifically preferred embodiment of the present invention the concentration of tetraphenylporphyrin is 0.75 mM and of 9,10-dicyanoanthracene is 2.5 mM each in toluene.

Photosensitizers can either be solubilized in the solvent (homogeneous system), immobilized on a solid support or any solid capable of promoting the generation of singlet oxygen may be used.

In general a photosensitizer as described herein is mixed with the reaction materials comprising dihydroartemisinic acid (2) and oxygen, and in a preferred embodiment the mixture is led through the transparent tube through the continuous flow reactor.

The electrical output of the light emitting diode or light emitting diode assembly is preferably between 60 and 100 W, and the light output of the light emitting diode or light emitting diode assembly is preferably between 5-50 W. In another preferred embodiment the optical output of the high energy LED module is up to 400 W and preferably ranges from 200 to 350 W, and is most preferably 280 W.

In another embodiment of the invention a Pyrex filter may be arranged between the light source and the tubing to absorb wavelengths below 300 nm, to prevent degradation of the tubing, and to avoid any undesired side reactions involving short wavelength light, wherein the Pyrex filter has a preferred thickness from 0.5 to 10 mm.

The continuous flow reactor of the box assembly comprises a tube made of a fluorinated or perfluorinated alkylene polymer having a preferred outer diameter within 0.0625 and 0.25 inch, and a preferred inner diameter within 0.03 and 0.12 inch. The corresponding tube volume lies preferably within the range of 3 to 30 ml.

Alike the "immersion well assembly" shown in FIGS. 1 and 4, the "box assembly" as described above as well as the "cooled box assembly" as shown in FIGS. 8, 9A and 9B use a solution of dihydroartemisinic acid (2), with a preferred concentration of about 0.2-1.0 mol/l in a proper solvent, which is led through the reactor by a simple HPLC pump, which has a preferred flow rate within 1 ml/min to 20 ml/min. Oxygen gas is added to this solution preferably by a T-type mixer before being led through the reactor.

According to the present invention the continuous conversion of dihydroartemisinic acid (2) requires the presence of oxygen gas in the reaction mixture for the photooxidation reaction. Further, also the Hock cleavage for the production of artemisinin (6) requires oxygen in the reaction mixture. This oxygen gas is preferably dissolved in high concentration, more preferably in the form of a saturated solution in the reaction medium. The method of the present invention comprises the provision of high oxygen levels within the reaction mixture by providing a set-up which allows a steady oxygen flow into the reaction mixture in order to generate high oxygen concentrations, preferably upon increased pressure within the reactor such as the tubing system. A steady flow can be provided according to the present invention by an oxygen tank being connected to a mixing device where the reaction medium containing photosensitizer and dihydroartemisinic acid (2) is brought in contact with oxygen. In a preferred embodiment the oxygen tank is further equipped with a manometer, a flow control and a check valve. According to the present invention oxygen can also be provided by a gas mixture containing oxygen as long as the other gas mixture components do not significantly interfere with the reaction or reagents. Suitable oxygen containing gas mixtures are air or synthetic air. Also, a simple mixture of oxygen with an inert gas such as nitrogen or noble gases may be suitable for the present invention. Oxygen or an oxygen containing mixture is preferably provided under increased pressure to the reaction mixture. Elevated pressure increases solubility of oxygen gas in the solvent and thus facilitates short residence times. The pressure for a suitable oxygen flow may range from atmospheric pressure to 50 bar, preferably from 5 bar to 20, more preferably from 7.5 bar to 15 bar and most preferably from 10 bar to 12 bar.

A steady oxygen flow is particularly preferred for the present invention as a continuous process requires the continuous provision of a reactant. Suitable flow rates according to the present invention range from 1 to 15 ml/min, preferably, 3 to 10 ml/min and most preferably from 5 to 7.5 ml/min.

Also, to further allow high oxygen levels within the reaction mixture back pressure regulators may be assembled in a reactor according to the present invention. Such a back pressure regulator allows keeping the pressure within the system, i.e. the tubing or any other reactor part, at an elevated pressure level, preferably ranging from 1.5 bar to 15 bar, more preferably from 2.2 bar to 10 bar and most preferably from 5 bar to 8 bar.

It is also part of the present invention that upon consumption of oxygen out of the reaction mixture a pressure gradient may occur over the length of the reactor. In another embodiment of the present invention several gas inlets may be incorporated in the reactor design allowing the installation of an adjustable pressure gradient within the reaction mixture.

As also stated above, the pressure drop over the length of the tubing 7 depends on various parameters and can be calculated in the laminar flow regime by the following formula $$\Delta p = \frac{8\mu L q}{\pi r^4},$$

whereby $\mu$ is the dynamic viscosity of the solvent, L is the length of the tubing, q the volumetric flow rate and r the inner radius of the tube.

Taking into account the roughness of the tube the actual pressure drop is higher. With a typical reactor setup (as given in example 12) and a back pressure regulator of 8 bar being attached to the exit of the reactor, a system pressure of about 10-12 bar after the pumping unit and before entering the photochemical reactor at the is found. The pressure drop of the whole reactor system is about 2-4 bar. The pressure of the regulator of the oxygen tank can be set preferably to 15 bar, further allowing adjustment of the flow rate with a gas flow controller. Due to the high oxygen pressure of 10-12 bar in the photochemical reactor of the continuous flow reactor, a higher oxygen solubility compared to atmospheric pressure is achieved. The pressure of >8 bar after the photochemical reactor is beneficial for the triplet oxidation occurring as well.

Also, oxygen availability in the system may be further increased by performing the reaction in perfluorinated solvents, such as hexafluorobenzene, or solvents with fluorinated moieties such as benzotrifluoride or bis(trifluoromethyl)benzene, which are characterized by a higher oxygen solubility. These additives may also be employed together with nonfluorinated solvents.

Because of the scale to $r^4$ the pressure drop can be reduced by a factor of 16 by doubling the tube diameter. Given a dynamic viscosity of 0.590 cP for toluene, the following pressure drops can be calculated:

| inner diameter tubing | volume per meter | pressure drop at q = 10 mL/min for volume of 100 mL |
|---|---|---|
| 0.030" (1/16" outer diameter tube) 0.75 mm | 0.44 mL | 29 bar (227 m tubing) |
| 0.062" (1/8" outer diameter tube) 1.55 mm | 1.89 mL | 0.4 bar (52.9 m tubing) |
| 0.156" (1/4" outer diameter tube) 4.0 mm | 12.6 mL | 0.001 bar (7.94 m tubing) |

A steady oxygen flow and associated with a high oxygen level in the reaction mixture is facilitated on the one hand by incorporation of mixing devices and by a reactor design capable of withstanding high pressure. Therein, the reactor design can be adjusted to uphold pressure in the entire system over at least one reaction component, preferably more than one reaction component until the reaction mixture exits for further reaction steps.

In a even more preferred embodiment of the invention the concentration of dihydroartemisinic acid (2) within the box assembly is 0.5 mol/l, wherein the flow rate in an explicit run of the reactor may lead to the corresponding conversion-, selectivity- and yield-values for the production of artemisinin (6), as shown in Table 1:

TABLE 1

| flow-rate of solution of starting material mL/min | flow-rate$^{-1}$ mmol/min | min mmol$^{-1}$ | conversion | mmol/min | yield hydro-peroxide (3) | selectivity |
|---|---|---|---|---|---|---|
| 0 | 0 | 0 | 0.0% | 0.00 | 0.0% | |
| 5 | 2.5 | 0.4 | 51.4% | 1.29 | 36.7% | 71.3% |
| 2.5 | 1.25 | 0.8 | 82.9% | 1.04 | 59.2% | 71.4% |
| 1.75 | 0.875 | 1.143 | 90.3% | 0.79 | 66.7% | 73.9% |
| 1.25 | 0.625 | 1.6 | 99.3% | 0.62 | 72.7% | 73.2% |

In contrast to the prior art the present invention provides a continuous photooxidation of dihydroartemisinic acid (2) enabling a steady processing which further facilitates a large conversion without the necessity of upscaling and which is not possible by a batch reactor design. Also, the present invention provides a process wherein dihydroartemisinic acid (2) is continuously converted by use of a mixture which is provided by the mixing gaseous oxygen preferably under pressure into the dihydroartemisinic acid solution for the photooxidation reaction requiring a specific reactor design for pressurized solutions with a potentially highly flammable gas.

Further, in another embodiment of the present invention the reaction sequence does not include a separation and/or isolation step during the conversion of dihydroartemisinic acid (2) to artemisinin (6). Also, depending on the reactor design it is possible to run the production of artemisinin according to the present invention in a semi-continuous manner. For example, in a semi-continuous reactor design the reaction solution and oxygen are delivered into the irradiation reactor compartment and are removed after a certain period of irradiation, e.g. by pumping the solution out from the reactor or by delivering new reagents. Such a semi-continuous reaction process can be performed periodically.

Preferably, the steps of conversion of dihydroartemisinic acid (2) with singlet oxygen and subsequently the reaction of the reaction product(s) of the aforementioned reaction step with oxygen in the presence of trifluoroacetic acid are conducted in a continuous manner.

In case of the immersion well assembly, the box assembly and the cooled box assembly as well as in the falling film assembly and the cylinder assembly the hydroperoxide (3) contained in the outflow of the reactor compartment of the photochemical reactor has to undergo an acid mediated cleavage of the hydroperoxide bond followed by subsequent oxidation preferably with oxygen (more specific with triplet oxygen) in order to obtain artemisinin (6).

Thus as outlined above, the hydroperoxide (3) is produced in the photochemical reactor of the present invention in a continuous flow process, while the next reactions can be performed by continuing said continuous flow process, starting a new continuous flow process or switching to a batch process.

In case of switching to a batch process, it is still not necessary to purify the hydroperoxide (3) or to remove the intermediate products (4) and (5). The obtained hydroperoxide (3) is simply collected in a batch reactor like a flask, is flushed with oxygen or an oxygen containing gas such as air, and treated with an acid such as TFA in order to obtain artemisinin (6). This method combining continuous flow through the photochemical reactor with subsequent batch process is described in example 2.

The second possibility of starting a new continuous flow process includes collecting the reaction solution coming out of the photochemical reactor of the continuous flow reactor which contains the hydroperoxide (3) and the intermediate products (4) and (5). No purification step or removal of the intermediate products (4) and (5) is required in order to perform the next reactions. The collected reaction solution may be concentrated or diluted and is fed into a second component of the continuous flow reactor together with oxygen or an oxygen containing gas such as air and an acid such as TFA in order to produce artemisinin (6), while this solution is running through that second continuous flow reactor. This method combining continuous flow through the photochemical reactor with subsequent continuous flow through the second continuous flow reactor is described in example 3. This method might be preferred in a case where more material could be processed through the second component of the continuous flow reactor than through the photochemical reactor so that probably the reaction solutions of two or more photochemical reactors are collected and then processed through one single second component of the continuous flow reactor.

The most preferred method is to continue the continuous flow process which is most preferred if photochemical reactor and subsequent continuous flow reactor have a similar capacity. In that method the reaction solution coming out of the photochemical reactor is directly forwarded to and/or fed into the subsequent continuous flow reactor components without first collecting said reaction solution. The acid is in one embodiment preferably added to the reaction solution coming out of the photochemical reactor and oxygen or an oxygen containing gas such as air is also fed into this reaction solution so that the hydroperoxide (3) in the reaction solution fed into the subsequent continuous flow reactor components is cleaved by the acid and oxidized by the triplet oxygen to the final product artemisinin (6). This most preferred method using one single continuous flow process from the production of artemisinin (6) from dihydroartemisinic acid (2) is described in example 4.

The photooxidation of dihydroartemisinic acid (2) was explored in a home-built continuous flow reactor as shown in FIGS. 1 and 4, comprising a photochemical reactor consisting of fluorinated ethylene propylene (FEP) tubing wrapped around a Schenk photochemical reactor containing a 450 W medium pressure mercury lamp that was cooled to 25° C. Such a reaction set-up refers to an immersion well assembly. Generally, preferred are photochemical reactors having a volume between 10 ml and 30 ml. A solution of dihydroartemisinic acid (2) in an organic solvent was added via a HPLC pump and oxygen was delivered via a mass flow controller connected to a gas cylinder. The solution of (2) and the oxygen gas were mixed using a ethylene tetrafluoroethylene (ETFE) T-mixer. Tetraphenylporphyrin (TPP) was used as photosensitizer due to its high quantum yield and high stability against photo-bleaching. Alternatively, rose Bengal (R.B.) and methylene blue (M.B.) can also be used as photosensitizer. Any other photosensitizer capable of promoting the generation of singlet oxygen could be used, for example: 5,10,15,20-tetrakis(pentafluorophenyl)porphyrin, tris(2,2'-bipyridyl)ruthenium (II), pheophytin a, pheophorbide a, 2,3,7,8-dibenzopyrene-1,6-quinone and metal-phthalocyanines.

In the case of the immersion well assembly, the box assembly and the cooled box assembly FEP or fluorinated ethylene propylene refers to a copolymer of hexafluoropropylene and tetrafluoroethylene. Other suitable fluorinated polymers are PTFE (polytetrafluoroethylene) and fluorinated ethylene propylene copolymers from DuPont sold under the brandname Teflon® FEP.

In the case of the immersion well assembly and the box assembly, the inventive method is preferably carried out at a temperature of 25° C. In general, a preferred temperature range is between −50 and 60° C., more preferred between 20 and 40° C. Generally, the inventive system can be well thermosetted resulting thereby in reliable and reproducible operation. Also, the inventive method can be cooled down to any desirable temperature only limited to physical barriers such as freezing of the solvent or precipitation of one reactant from the reaction mixture. However, the inventive method can also be heated up to a temperature at which a solvent would start to boil and incur damages to the reactor.

In some embodiments such as the cooled box assembly, the cylinder assembly or the falling film assembly embodiment it is preferred that the temperature for the photooxidation reaction ranges from room temperature down to −30° C., more preferably from 10° C. to −25° C., even more preferably from 0° C. to −20° C., yet even more preferably from −10° C. to −20° C., and most preferably from −15° C. to −18° C. In a preferred embodiment the temperature for the photooxidation reaction is −20° C.

It was found that the selectivity of the reaction can be improved in terms of a low amount of byproducts when the photooxidation reaction is performed at low temperatures, such as below 0° C. as defined above. In a preferred embodiment the photooxidation reaction is performed at −18° C. It was found that the conversion of the starting material DHAA is nearly complete in a temperature range from −20° C. to 80° C. It was further found that lower temperature beneficially influences a shifting of the ratio of the different peroxides towards the preferred hydroperoxide (3) in comparison to the byproducts (4) and (5). Specifically, the reaction temperature has a pronounced effect and at low temperature of e.g. −18° C. the amount of side products can be decreased to 5%. At this temperature, a maximum selectivity of 82% for the desired peroxide is obtained. It is therefore worthy to cool the reactor for the photooxidation step in order to obtain a higher yield of artemisinin (6) and less side products granting the benefit of simplifying later purification.

Also, it was found that an efficient cooling system such as introduced by the cooled box assembly further provides the possibility of increasing the energy level of the induced radiation during the photooxidation reaction since an energy transfer of radiation heat to the cooling liquid can occur. Therefore, running the continuous flow reaction of photooxidation at decreased temperatures high energy radiation can be applied in order to efficiently convert DHAA (2) to the preferred hydroperoxide (3). Further, by increasing the energy input on the photooxidation reaction the production capacity can approximately be increased by the factor the energy input is increased. Thus, increasing the energy input by a factor 5, the product capacity may preferably be increased by a factor 5.

Since oxygen gas can result in severe fires a non-flammable, typically halogenated solvent is required. On large scale, halogenated solvents other than dichloromethane are considered too toxic so that dichloromethane is the preferred solvent for large scale production of artemisinin (6). But also other solvents have been found of being particular suitable for the production of artemisinin (6). Among those other suitable solvents, besides dichloromethane, there are fluorinated and perfluorinated $C_4$-$C_6$ hydrocarbon solvents, fluorinated and perfluorinated aromatic solvents such as 1,3-bis(trifluoromethyl)benzene, hexafluorobenzene and benzotrifluoride, aromatic solvents such as benzene, toluene, mesitylene and xylenes as well as cyclohydrocarbon solvents such as cyclobutane, cyclopentane, cyclohexane and cycloheptane. Fluorinated solvents were found to exhibit high oxygen solubility and long lifetime of singlet oxygen, which is beneficial for the first photooxidation step. For the acid catalyzed reaction fluorinated aromatic compounds perform well concerning artemisinin yield and prevention of byproducts. Further preferred for the synthesis of artemisinin according to the present invention are 1,3-bis(trifluoromethyl)benzene, hexafluorobenzene and benzotrifluoride, toluene and cyclohexane, and most preferred is toluene. Under preferred conditions, 1.50 mmol of intermediate (3) were produced per minute when a 10 ml to 60 ml reactor and preferably a 20 mL reactor was fed with 2.5 mL/min of the solution of dihydroartemisinic acid (2) in dichloromethane and oxygen was fed at a flow rate of 5 mL/min. At 91% conversion and a yield of 75% for this step this process was better or at least as good as any process ever described for this transformation.

Protonation of the peroxide (3) is required to induce cleavage and rearrangement of the cyclic structure. The intermediate product evolved from the protonation of the endoperoxide oxygen atom of compound (3) undergoes undesired reactions which in the state of the art have been suppressed by the conversion of the carboxylic acid into an ester or a mixed anhydride. Such a transformation requires additional steps and the use of the carboxylic acid reduces considerably the formation of the 6-membered lactone product. The inventive method disclosed herein does not require the protection of the carboxylic acid group as an ester or mixed anhydride.

For efficiently performing the method of the present invention different Brønsted and Lewis acids were tested in various solvents in order to find the most efficient path for converting the peroxide obtained after the singlet oxygen reaction into the intermediate which is reacted with triplet oxygen to obtain artemisinin (6). As result from this screening, acids can either be used in a homogeneous fashion or in an immobilized form as an acidic ion exchange resin. The following Brønsted and Lewis acids were tested: camphorsulfonic acid, copper(II) trifluoromethanesulfonate, DOWEX®, p-toluenesulfonic acid, trifluoroacetic acid amberlite IR 120 ion exchange resin, acetic acid, sulfuric acid and conc. hydrochloric acid. Other suitable Brønsted or Lewis acids having similar pKa could be used. There are no special requirements for the acid. Trifluoroacetic acid (TFA) performed so far best as acid to induce the Hock cleavage, but other acids with similar pKa could also be feasible. Moreover, addition of small amounts of water to the TFA solution did not deteriorate conversion and/or selectivity. Therefore, it is preferred for the method of the present invention that trifluoroacetic acid is used for the acid mediated cleavage.

Additionally, not only heterogeneous acids for the Hock cleavage can be immobilized on the surface of the compartments material, but also heterogeneous photosensitizers resulting in a high contact area significantly promoting the various reactions within the reactor of the present invention.

It is essential to point out that a Brønsted acid or a Lewis acid needs to be added to perform the Hock cleavage. This addition could be done directly at the beginning or just after the completion of the reaction with singlet oxygen. The addition of the acid after the photooxidation reaction is preferred in case an acid-sensitive photosensitizer is employed, so that preferably the acid is added to the reaction solution leaving the photochemical reactor. For example, treatment of the crude tertiary allylic hydroperoxide (3) obtained from the photochemical reactor with 0.5 eq. of TFA at 0° C. while bubbling oxygen (pure oxygen or air) gave, after purification by chromatography, artemisinin (6) in 50% yield.

In an effort to minimize manipulations of the reaction mixture and move to a fully continuous process, the Hock cleavage step with the action of acid and the addition of oxygen were performed in one continuous flow set-up. Best results were obtained in a, for instance, 42 mL reactor at a flow rate of, for instance, 2.5 mL/min of the crude tertiary allylic hydroperoxide (3) in dichloromethane, a flow rate of 5.0 mL/min of oxygen and a flow rate of 0.5 mL/min of TFA in dichloromethane. The first portion of the reactor (32 mL) was preferably maintained at room temperature and the last portion (10 mL) was preferably heated at 60° C. to push the reaction to completion. The ensuing triplet oxygen oxidation produced desired artemisinin (6) and five member lactone byproduct in a ratio of 5.3:1.0 in favor of (6). Following purification by chromatography yielded 46% of (6) in this sequential continuous flow multistep reaction from dihydroartesiminic acid (2).

Further, it was found that the temperature of the reaction mixture after the photooxidation reaction for the acid-catalyzed reaction cascade has significant impact on the conversion of the hydroperoxide (3) into the desired product artemisinin (6). It was found that decreased temperatures ranging from 0° C. to −15° C. only provide high yield of the desired reaction product artemisinin (6) if the reaction duration is unfavorably extended. However, it was surprisingly found that high yields of artemisinin (6) can be derived preferably in a temperature range of 10° C. to 50° C., more preferably in a range of 15° C. to 30° C., and most preferably at 25° C. (FIG. 10 A). It was further found that increasing the temperature over the preferred temperature range results in a more pronounced formation of byproducts while the artemisinin yield decreases.

Moreover it was found that solvents with a lower dipole moment resulted in better selectivity so that the acid and especially TFA was dissolved in toluene, benzene, cyclohexane, xylene or dioxane.

The final synthetic transformation of the intermediate compound obtained after acid cleavage to artemisinin (6) requires an oxidation with triplet oxygen that is followed by a cascade of reactions that produce two rings, including the peroxide framework of artemisinin (6). According to one embodiment of the present invention, the Hock cleavage step with the action of acid and the addition of oxygen were performed in one continuous flow set-up as shown in FIG. 2.

In comparison to batch processes a continuous process and reactor design as described herein allow the use of smaller dimensions of the various reactor parts and compartments. However, it is still possible to undergo an up-scaling with the reactor design of the present invention by for example extending the length of the tubing/reaction components. Adequate geometries can be applied to the tubing or other components with small thickness or dimensions. Such adjusting of dimension can also be applied to a falling film assembly, e.g. to the different plates and the gap between these plates allowing a liquid film with different thickness to flow in the centre.

The possibility of applying small dimensions and/or diameters for the components of the continuous flow reactor of the present invention where the reactions occur is advantageous over batch reactor design. In that, it is possible to adjust a design with a high specific surface area. This is for example beneficial for a fast mass transport of oxygen from the gas phase into the solution. An efficient irradiation can be achieved as the intensity of light decreases with increasing distance from the light source. Therefore, big vessels generally used in batch reactor design are difficult to irradiate. Structures with thin diameter on the other hand can easily be irradiated with high intensity and the reaction accelerated significantly.

Also as part of the reactor design, various reactor parts and components may be used that work on the basis of mechanic principles. For example, mixing pieces, pressure gauges, flow meters, mixing devices and back pressure valves may be designed to work in a classic fashion without the necessity of electrical power. However, various reactor parts and components such as mixing pieces, pressure gauges, flow meters, mixing devices and back pressure valves as well as the lights sources, cooling systems and pumps may also be designed to run electrically and can be controlled in a remote fashion from a computational unit if desired.

These various reactor parts and components all add up to the continuous flow reactor of the present invention. Preferably this continuous flow reactor at least comprises a photochemical reactor for the production of artemisinin from dihydroartemisinic acid comprising
   a light source,
   mixing device for mixing oxygen with a solution of dihydroartemisinic acid,
   reactor compartment being at least partially irradiated by the light source and having an inlet for the mixture of dihydroartemisinic acid and oxygen on its one end and an outlet for the reacted products on the opposite end.

The continuous flow reactor according to the present invention may further comprise an oxygen source capable of providing oxygen above atmospheric pressure. In a preferred embodiment of the present invention this oxygen source is an oxygen tank with a manometer, a flow control and/or a check valve. In the photochemical reactor according to the present invention the reactor compartment may be tubing. Also in the photochemical reactor according to the present invention the mixing device is a T-mixer valve.

In a preferred embodiment of the present invention the photochemical reactor may comprise
   a box which is impervious to light with light reflecting inner walls and one opening through which the tubing enters the box and another opening through which the tubing leaves the box and
   multiple loops of the tubing arranged in the inside of the box, wherein the tubing has an inlet for a mixture of dihydroartemisinic acid and oxygen on its one end before entering the box and an outlet for the reacted products on the opposite end after leaving the box, and the continuous flow reactor of the present invention may optionally also comprise
   a cooling liquid and a chiller, as well as
   a back pressure regulator, in addition to the afore-mentioned photochemical reactor.

However, it may also be that the photochemical reactor according to the present invention only comprises
   a light source,
   mixing device for mixing oxygen with a solution of dihydroartemisinic acid,
   reactor compartment being at least partially irradiated by the light source and having an inlet for the mixture of dihydroartemisinic acid and oxygen on its one end and an outlet for the reacted products on the opposite end.

In such a case it may also be that the continuous flow reactor of the present invention may further comprise an oxygen source capable of providing oxygen above atmospheric pressure. In a preferred embodiment of the present invention this oxygen source is an oxygen tank with a manometer, a flow control and/or a check valve. The continuous flow reactor of the present invention may further comprise:
   a box which is impervious to light with light reflecting inner walls and one opening through which the tubing enters the box and another opening through which the tubing leaves the box and
   multiple loops of the tubing arranged in the inside of the box, wherein the tubing has an inlet for a mixture of dihydroartemisinic acid and oxygen on its one end before entering the box and an outlet for the reacted products on the opposite end after leaving the box, and may optionally also comprise
   a cooling liquid and a chiller,
   a feed for an acidic solution,
   at least one reactor for producing or completing the synthesis of artemisinin, connected downstream to the photochemical reactor,
   a collection flask for collecting the artemisinin-containing solution from at least one reactor,
   a second reactor downstream to the first reactor or
   a second reactor downstream to the first reactor and a third reactor downstream to the second reactor,
   a back-pressure regulator downstream to the first reactor or the second reactor or the third reactor,
   a pump for the feed of the photochemical reactor containing at least dihydroartemisinic acid, solvent and photosensitizer, optionally further comprising acid,
   a check-valve between a first pump and the first mixer,
   a mass flow controller disposed between the oxygen tank and the first mixer for controlling the oxygen flow rate, a check valve between the mass flow controller and the first mixer,
a second mixer connected to the outlet of the tubing of the photochemical reactor and to the acid feed and
a second pump for pumping the acidic solution to the second mixer.

IMMERSION WELL ASSEMBLY

In the case of the immersion well assembly, the invention refers to a photochemical reactor for the production of artemisinin (6) from dihydroartemisinic acid (2) comprising or consisting of
a light source 11,
an immersion well 9 surrounding the light source 11,
a filter 8 surrounding the light source 11 and
multiple loops of a tubing 7 wrapped tightly around the filter 8, the tubing 7 having an inlet for a mixture of dihydroartemisinic acid and oxygen on its one end and an outlet for the reacted products on the opposite end.

The immersion well 9 surrounding the light source 11 preferably in a cylinder-like shape and the filter 8 surrounding also the light source 11 preferably in a cylinder-like shape while the filter 8 could be inside the immersion well 9 or the immersion well 9 could be inside the filter 8. If the filter 8 is inside the immersion well 9 surrounding the light source 11, the tubing is directly wrapped around the immersion well 9 and indirectly also wrapped around the filter 8 and the light source 11. If the immersion well 9 is inside the filter 8 surrounding the light source 11, the tubing is directly wrapped around the filter 8 and indirectly also wrapped around the immersion well 9 and the light source 11. However it is preferred that the light source 11 is directly surrounded by the immersion well 9 and the immersion well 9 is again surrounded by the filter 8 and the filter 8 is again surrounded by the tubing 7.

Tightly wrapped, as used herein, means that the tubing is wrapped around the filter in such a way that it keeps tight to the underlying filter and is not liable to slide down or to be shifted involuntarily or by applying flow pressure and/or temperature to the device. On the other hand it isn't wrapped that tightly that the tubing material gets overstretched and could be easily damaged by physicochemical stress or use. The main difference between the photochemical reactor used within the present invention and any common photochemical reactor such as the Scheck photochemical reactor is that the reactor vessel which usually surrounds the immersion well is replaced by the tubing which is wrapped around the filter and the immersion well.

In the case of the immersion well assembly and the box assembly a Pyrex filter is preferred as filter. Preferably, it has an inner diameter of 4.85 cm and a wall thickness of 0.28 cm. The diameter of the filter is related to the diameter of the immersion well. The filter could also be placed inside the immersion well, just around the lamp. In that case the diameter of the filter is smaller but the thickness is the same.

For the tubing of the photoreactor FEP (fluorinated ethylene polymer) is preferred as material. A preferred FEP tubing is from IDEX Health & Science, FEP 1520, natural color, outside diameter (OD) 1/16 in and inside diameter (ID) 0.030 in). Another preferred tubing may have an outside diameter (OD) 1/8 in. In general, the internal diameter (ID) can be from 0.003 in to 0.120 in. FEP tubing having the internal diameter of 0.003 in, 0.004 in, 0.008 in, 0.010 in, 0.020 in, 0.030 in, 0.062 in, 0.125 in, 0.156 in, 0.250 in, 0.5 mm, 1 mm, 2 mm and 3 mm are easily commercially available. In general, the outer diameter (OD) can be from 1/32 in to 4 mm. FEP tubing having the outer diameter of 1/32 in, 1/16 in, 1/8 in, 3/16 in, 1/4 in, 5/16 in, 1 mm, 2 mm, 3 mm and 4 mm are easily commercially available. Alternatively, fluorinated or perfluorinated alkylene polymer or fluorinated ethylene propylene can be used FEP was preferably selected for the tubing due to its high transmittance and stability in the UV-vis light range, its flexibility and its high chemical resistance. Any polymer having these properties could be used instead of FEP.

In the case of the immersion well assembly the immersion well is preferably made of quartz. Since a pyrex filter is used, also an immersion well made of pyrex (borosilicate) could be used.

In the case of the immersion well assembly the photochemical reactor may further comprise a thermostat 10 for cooling the immersion well 9. Thus, this photochemical reactor comprises or consists of:
a light source 11,
an immersion well 9 surrounding the light source 11,
a thermostat 10 for cooling the immersion well 9,
a filter 8 surrounding the light source 11 and
multiple loops of a tubing 7 wrapped tightly around the filter 8, the tubing 7 having an inlet for a mixture of dihydroartemisinic acid and oxygen on its one end and an outlet for the reacted products on the opposite end.

In the case of the immersion well assembly the light source is preferably a Hg lamp and more preferably a medium pressure Hg lamp (such as Ace Glass, UV 450 immersion lamp, 5 in arc, radial lead, 7825-34). However the use of mercury lamps is not mandatory, also LEDs, fluorescent lamps or halogen lamps could be used.

In the case of the immersion well assembly the use of a 450 W Hg lamp is preferred. In general the power range can be from 100 W to 1200 W. Lamps having the powers of 100 W, 200 W, 450 W, 500 W and 1200 W are easily commercially available.

In the case of the immersion well assembly the light source needs an adapted power source 12. For such an Ace Glass lamp an Ace Glass, 7830 power supply is preferred. However, any power source supplying this power could be used.

In the case of the immersion well assembly, the inventive photochemical reactor may optionally further comprise a thermostat for cooling the immersion well.

The thermostat is for example a Huber, Unistat 360. Any cooling system able to cool down the lamp at the desired temperature could be used. For example another photochemical reactor uses a Julabo FL601. Also, one cooling system could be used for more than one photochemical reactor.

In the case of the immersion well assembly, the present invention furthermore refers to a continuous flow reactor as depicted in FIGS. 1 and 2 for the production of artemisinin (6) from dihydroartemisinic acid (2) comprising or consisting of
the photochemical reactor described before,
a first mixer 6a, connected to the inlet of the tubing 7 of the photochemical reactor,
a feed F1 for a solution of dihydroartemisinic acid,
a first pump 1a for pumping the solution of dihydroartemisinic acid to the first mixer 6a,
a check-valve 5a between the first pump 1a and the first mixer 6a,
an oxygen tank 4 with a manometer 3,
a mass flow controller 2 disposed between the oxygen tank 4 and the first mixer 6a for controlling the oxygen flow rate,
a check valve 5b between the mass flow controller 2 and the first mixer 6a,
a feed F2 for an acidic solution, a second mixer 6b connected to the outlet of the tubing 7 of the photochemical reactor and to the feed F2 of the acidic solution, a second pump 1b for pumping the acidic solution to the second mixer 6b, at least one reactor 15 for producing or completing the synthesis of artemisinin, connected downstream to the second mixer 6b, and a collection flask 18 for collecting the artemisinin-containing solution from the at least one reactor 15.

In the case of the immersion well assembly and the box assemblies it is evident to a skilled person that the continuous flow reactor of the present invention also may comprise, for instance, tubing for connecting said parts or fastener and clamps for fixating the single components of the continuous flow reactor. However these parts are not essential to the invention and thus are not explicitly mentioned in the patent claims.

In an alternative embodiment the acidic solution flows from its feed F2 not to the second mixer 6b but to the first mixer 6a and the second pump 1b is not arranged between the feed F2 for the acidic solution and the second mixer 6b but between the feed F2 for the acidic solution and the first mixer 6a.

In the case of the immersion well assembly and the box assemblies it is preferred that the pumps are HPLC pumps. More preferred are models such as a Vapourtec R2C+ unit. Any HPLC pumps or pumps for continuous flow systems can be used such as Syrris pumps. For certain embodiments an acid resistant pump is required in order to pump the solution of the acid such as the TFA solution.

The mass flow controller is preferably from Influx, SVIB5-Al05. It allows the control of the flow rate from 5-90 $cm^3$/min. Any mass flow controller allowing to control this range of flow rates can be used.

The oxygen tank can be for example an Air Liquide, $O_2$ (99.995% pure). However the purity of the oxygen is not important. Also air instead of 99.9% pure oxygen worked well.

The check-valves are preferably from IDEX Health and Science, inline check-valve CV-3010. The use of check-valve is preferred but not essential. Any check-valve can be used. The check-valve was used in order to prevent the solvent to go into the mass flow controller.

For both mixers ETFE T-mixers are preferred. Particularly preferred is a IDEX Health and Science, P-632. The ETFE T-mixers are preferred, because the material has high corrosion resistance and strength over a wide temperature range. Other polymers having similar properties could be used. The T-mixers could also be changed for mixers that have other shape, for example a Y-mixer.

The tubing of the inventive device apart of the photoreactor is preferably of FEP. This tubing was selected for its high transmittance and stability in the UV-vis light range, its flexibility and its high chemical resistance. Any polymer having these properties could be used instead of FEP.

For the cleavage and triplet oxygen oxidation at least one PTFE reactor is preferred. Preferably two reactors (15, 16) are used which preferably have different temperatures for processing the intermediate products. For the first reactor 15 it is preferred that it has a volume of 10 mL to 60 mL and more preferably of 16 to 32 mL, Omnifit, outside diameter (OD) 1/16 in and inside diameter (ID) 0.8 mm). This first reactor 15 is preferably kept at room temperature.

Moreover, the inventive continuous flow reactor may further comprise a second reactor 16 downstream to the first reactor 15. This second reactor 16 is preferably kept at a temperature between 50° C. and 70° C. and more preferably at about 60° C. For the optional second reactor 16 it is preferred that it is a 10 mL reactor from Vapourtec, R4 unit. Any device able to heat a reactor to a temperature between 50° C. and 70° C. and preferably to 60° C. could be used instead of the Vapourtec R4 unit, for example, other commercially available continuous flow systems, oil bath or water bath with an heating plate or a heating mantle.

In another embodiment of the present invention three reactors (15, 16, 17) are used which preferably have different temperatures for processing the intermediate products. For the first reactor 15 it is preferred that it has a volume of 5 mL to 20 mL and more preferably of 5 mL to 8 mL, Omnifit, outside diameter (OD) 1/16 in and inside diameter (ID) 0.8 mm). This first reactor 15 is preferably cooled to 0° C. The inventive continuous flow reactor may further comprise a second reactor 16 downstream to the first reactor. For the optional second reactor 16 it is preferred that it is a 10 mL to 60 mL reactor and more preferably a 25 mL to 30 mL reactor. This second reactor 16 is preferably used at room temperature. Moreover, the inventive continuous flow reactor may further comprise a third reactor 17 downstream to the second reactor 16. This third reactor 17 is preferably kept at a temperature between 50° C. and 70° C. and more preferably at about 60° C. For the optional third reactor 17 it is preferred that it is a 5 mL to 60 mL reactor and more preferably a 10 mL reactor such as from Vapourtec, R4 unit. Any device able to heat a reactor at about 60° C. could be used instead of the Vapourtec R4 unit, for example: other commercially available continuous flow systems, oil bath or water bath with a heating plate or a heating mantle.

Also, it is preferred that before the reaction mixture is led to the collection flask 18 a back-pressure regulator 14 is incorporated into the immersion well assembly. Such a back pressure regulator can also be incorporated into other reactor assemblies such as the box assembly or the cooled box assembly. The optional back-pressure regulator needs to be acid resistant and is preferably from Vapourtec. It operates most preferably at 2.2 bar, but is adjustable for the inventive method in a preferred range from 0 to 8 bar. Any acid resistant back-pressure regulator operating in that range of pressure could be used instead of the one provided by Vapourtec.

Thus, the present invention is also related to artemisinin (6) produced or synthesized according to the method disclosed herein. More preferably the present invention is directed to artemisinin (6) produced or synthesized according to the method disclosed herein using the continuous flow reactor as disclosed herein.

Optionally, the inventive continuous flow reactor may further comprise an automated two inlet switch valve 13a for regulating the composition of the feed F1 for the solution of dihydroartemisinic acid (2), allowing for rapid switching from pure solvent to the solution containing the dissolved dihydroartemisinic acid (2). A similar switch valve 13b can be disposed in the feed F2 of the acidic solution (for instance a TFA solution) in order to regulate the composition by portioning the stem solution of the acidic solution and the respective solvent. Any valves could be used, as long as they are resistant against corrosion and acids.

In FIG. 1 a schematic drawing of an inventive photochemical reactor according to the immersion well assembly is depicted. The photochemical reactor is the central piece of the continuous flow reactor according to the invention. In the center of the photochemical reactor is a light source, preferably an Hg lamp. The light source has an oblong shape. Its longitudinal axis is vertical. However, the photochemical reactor could also be used in the horizontal orientation, i.e.

where its longitudinal axis is horizontal. The lamp is disposed centrally in an immersion well that surrounds the lamp in a cylinder-like shape. At a certain distance (for instance, the outer diameter of the immersion well is 4.83 cm and the inner diameter of the pyrex filter is 4.85 cm, so the distance between the two should be 0.01 cm) a further cylinder-like shape surrounds the immersion well, having the same central point. This structure is a filter, preferably a Pyrex filter. Around this filter multiple loops of tubing are wrapped in a spiral like form. Thus the outer diameter of the filter determines the inner diameter if these loops. The number of loops can be variable. The distance between the loops is preferably equidistant but this is not compulsory. There are preferably two layers of loops, the first layer (the closest to the lamp) is made of, for instance, approximately 135 loops and the second layer of, for instance, approximately of 115 loops, so that the complete tubing consists of approximately 250 loops. However, the tubing preferably consists of 100 to 1000 loops in one, two or three layers, preferably of 150 to 500 loops in one, two or three layers, more preferably of 200 to 400 loops in one, two or three layers, still more preferably of 220 to 300 loops in one, two or three layers, and most preferably of 230 to 270 loops in one, two or three layers. Moreover two or three layers of loops and more preferably two layers of loops are preferred. It is also preferred that there is no distance between the loops. At the upper end of the tubing there is a connection to a mixer in which dihydroartemisinic acid and oxygen are mixed. At the lower end of the tubing there is an outlet for the reaction products for further processing. For this process the addition of an acidic solution such as TFA solution is needed. This addition can take place in the mixer together with the dihydroartemisinic acid and the oxygen, or alternatively when the products have left the photoreactor.

FIGS. 2 and 4 show the continuous flow reactor setup according to the immersion well assembly for the synthesis of artemisinin (6) starting from dihydroartemisinic acid (2). The continuous flow reactor for the synthesis of artemisinin (6) consists of two pumps 1a and 1b, a mass flow controller 2 connected to a manometer 3 fixed on an oxygen tank 4 and a check-valve 5a between the pump 1a and another check valve 5b between the mass flow controller 2 and the mixer 6a. The center piece of the continuous flow reactor is a photochemical reactor with the mixer 6a and multiple loops of a tubing 7 wrapped tightly around a filter 8, which surrounds an immersion well 9, optionally cooled by a thermostat 10, a light source 11, a power supply 12 for the photochemical lamp 11, a second mixer 6b, a reactor 15, preferably a second reactor 16, preferably a third reactor 17 and a collection flask 18. The flow reactor setup comprises preferably in addition an automated two inlet valve 13 allowing for rapid switching from pure solvent to the solution containing the dissolved reagents at the intake pump and optionally a back-pressure regulator 14 which was installed in order to increase the internal pressure of the system. All the parts are connected with tubing.

In a preferred embodiment as depicted in FIG. 11 the immersion well assembly as depicted in FIG. 2 can further comprise an additional pressure regulator 14a between the photochemical reactor and the second mixer 6b.

FEP tubing was preferably selected for its high transmittance and stability in the UV-vis light range, its flexibility and its high chemical resistance. The 2 mm thick Pyrex filter was advantageous to absorb wavelengths below 300 nm, to prevent degradation of the tubing, and to avoid any undesired side reactions involving short wavelength light. The temperature in the tube during the reaction is estimated to range preferably from 25 to 30° C., based on temperature of the cooling liquid, which circulate in the immersion well, between the lamp and the filter. For safety reasons, the lamp was placed inside an aluminum box for blocking UV irradiation. Two fans can optionally be installed for additional cooling.

A solution of dihydroartemisinic acid (2) and the photosensitizer in dichloromethane was mixed (2.5 mL/min) with a flow of oxygen gas (7.5 mL/min) and passed through the above described photoreactor. The residence time in the reactor is approximately 2.0 minutes. Using a Vapourtec R2C+ pump, a solution of TFA in toluene was added at a flow rate of 0.5 mL/min with the outlet stream of the photochemical reactor containing mainly intermediate (3) to induce the acid catalyzed Hock cleavage. A PTFE reactor (having two components: a 16 mL volume kept at room temperature and a 10 mL volume heated at about 60° C.) resulted in approximately 2.5 min residence time to achieve also the reaction of triplet oxygen and further condensation. After a total residence time of 4.5 min the product stream containing mainly desired artemisinin (6) was obtained. Purification by chromatography was performed. The overall yield of (6) in the multistep reaction from dihydroartesiminic acid (2) is 39% with a productivity of 200 g of the anti-malaria compound per day. A rough calculation based on 300 million doses of artemisinin needed per year reveals that approximately 2050 photoreactors are needed to meet the demand, even if no further improvements are made to the process described here.

BOX ASSEMBLY

The present invention also refers to a device in which the inventive process of producing artemisinin takes place. In the case of the box assembly (FIG. 5 and FIG. 6), the invention refers to a continuous flow reactor comprising a photochemical reactor for the production of artemisinin (6) from dihydroartemisinic acid (2) comprising or consisting of

- a light emitting diode module (LED module) 23 which is lighting the transparent body 21 in a frontal direction of lighting 25,
- a LED module 23 in which the arranged LED's 24 are face to face to the transparent body 21
- a box 20 which is preferably lightproof,
- a transparent body 21 which is wrapped by a FEP tubing 22
- multiple loops of a tubing 22 wrapped tightly around the transparent body 21, the tubing 22 having an inlet 29 for a mixture of dihydroartemisinic acid and oxygen on its one end and an outlet 26 for the reacted products on the opposite end.

The transparent body 21 in front of the LED module 23 has preferably a square and plane shape. The surface of the inner box wall 27 has preferably a light reflecting property as it may consist of an aluminium foil.

In the case of the box assembly the photooxidation of dihydroartemisinic acid (2) was explored in a home-built continuous flow reactor as shown in FIGS. 5 and 6, comprising a photochemical reactor consisting of fluorinated ethylene propylene (FEP) tubing wrapped around a transparent body (preferably a panel of polycarbonate) which is placed inside a box, whereby the inner box also contains a light source wherein light source of the box assembly is an assembly of light-emitting diodes which have a light emitting wavelength of 420 nm or 660 nm. Preferred is tubing of the photochemical reactors having a volume between 10 ml and 30 ml. A solution of dihydroartemisinic acid (2) in an organic solvent was added via a HPLC pump and oxygen was delivered via a mass flow controller connected to a gas cylinder. The solution of (2) and the oxygen gas were mixed using a ethylene tetrafluoroethylene (ETFE) T-mixer. Tetraphenylporphyrin (TPP) was used as photosensitizer due to its high quantum yield and high stability against photo-bleaching. The inner walls of the box contain a light reflecting aluminum foil surface.

The technical values according to the box assembly may be described as shown in Table 2:

TABLE 2

| Use of with 660 nm LED and methylene blue: | | | |
|---|---|---|---|
| light output | 8.7 W | electric output | 46 W |
| photon flow: | 2.88 mmol/min | quantum yield $^1O_2$ | 0.52 |
| singlet $O_2$: | 1.50 mmol/min | | 2.16 mol/d |
| selectivity artemisinin: | 0.4 | mass/day: | 243.38 g/d |
| light output for 1 kg artemisinin: | | | 0.86 kWh |
| electric output for 1 kg: | | | 4.54 kWh |
| Use of 420 nm LED and tetraphenylporphyrin: | | | |
| light output | 12 W | electric output | 72 W |
| photon flow: | 2.53 mmol/min | quantum yield $^1O_2$ | 0.63 |
| singlet $O_2$: | 1.59 mmol/min | | 2.292 mol/d |
| selectivity artemisinin: | 0.4 | mass/day: | 258.82 g/d |
| light output for 1 kg artemisinin: | | | 1.11 kWh |
| electric output for 1 kg: | | | 6.68 kWh |

In FIG. 5 a schematic drawing of a continuous flow reactor with a focus on the photochemical reactor according to the box assembly is depicted. In the box assembly the central piece of the continuous flow reactor is the wrapped transparent body 21 which is lighted by the LED module 23 according to the invention. The photochemical reactor of the box assembly comprises a setup which consists of a tube made of a fluorinated or perfluorinated alkylene polymer 22 wherein the photooxidation of dihydroartemisinic acid takes place and which is wrapped around a transparent body 21, which is placed inside a box 20, wherein the box also contains a light source. The light source is an assembly of arranged LED's 24 which are part of the LED module 23. The light-emitting diodes have a preferred light emitting wavelength of 420 nm and/or 660 nm. The setup of the arranged LED's 24 are within a plane module having an emission-surface within 0.5×0.5 cm² to 20×20 cm², or even more preferred of at least 2.5×2.5 cm². Within the box assembly containing the light source and the tubing wrapped around a transparent body, more than one module of light emitting diodes 23 may be arranged around the wrapped tubing, containing the dihydroartemisinic acid (2) and the oxygen for the photooxidation reaction. The inner walls of the box 20 containing the tubing 22 and the light source, have a light reflecting surface 27 wherein in another embodiment of the invention the box 20 may also contain reflectors, having a light reflecting surface, wherein the reflectors are arranged around the tubing and the light source. The light reflecting surface and/or the reflectors lead to a specular reflection of the light of the arranged LED's 24 within the box 20. Moreover the light reflecting surface and/or the reflector may be made out of a light reflecting material which has a light reflectivity of at least >70%, or more preferably >90%, wherein the reflected light spectra comprises the wavelengths needed to perform the photooxidation reaction of dihydroartemisinic acid (2). In a preferred embodiment of the invention the reflected spectra in the box assembly contains the wavelengths of 420 nm and/or 660 nm.

According to a preferred embodiment as depicted in FIG. 12 the continuous flow reactor as depicted in FIG. 5 can further comprise an additional pressure regulator 14a at the outlet of the photochemical reactor.

The number of loops of the wrapped tubing 22 can be variable. The distance between the loops is preferably equidistant but this is not compulsory. There are preferably two layers of loops, the first layer (the closest to the lamp) is made of, for instance, approximately 135 loops and the second layer of, for instance, approximately of 115 loops, so that the complete tubing consists of approximately 250 loops. However, the tubing preferably consists of 100 to 1000 loops in one, two or three layers, preferably of 150 to 500 loops in one, two or three layers, more preferably of 200 to 400 loops in one, two or three layers, still more preferably of 220 to 300 loops in one, two or three layers, and most preferably of 230 to 270 loops in one, two or three layers. Moreover two or three layers of loops and more preferably two layers of loops are preferred. It is also preferred that there is no distance between the loops. At the upper end of the tubing there is a connection to a mixer 28 in which dihydroartemisinic acid and oxygen are mixed. At the lower end of the tubing there is an outlet 26 for the reaction products for further processing. For this process the addition of an acidic solution such as TFA solution is needed. This addition can take place in the mixer together with the dihydroartemisinic acid and the oxygen, or alternatively when the products have left the photoreactor.

The box 20 is preferably light proof, preventing electromagnetic radiation from leaving or entering the box. In a most preferred embodiment only the openings through which the tube enters and leaves the box are the only two openings through which light might be able to leave or enter the box. The box assembly can comprise any housing capable of accommodating at least the photochemical reactor consisting of or comprising the transparent body 21 and wrapped tubing 22 as well as the light source consisting of or comprising the LED module 23 and the arranged LEDs 24. However, also other reactor components can be accommodated into the box of the box assembly. The box preferably comprises connection points and/or connectors for the tubing inlets (29) and outlets (26), as well as connection points and/or connectors for electric cables or support cables for the operation of the LED-module or modules 23 and other internal devices that need electricity (e.g. motors or electric valves). In a further embodiment of the invention the box assembly may further comprise a series connection of several transparent bodies 21 wrapped by the tubing 22, wherein this assembly of wrapped bodies may preferably be surrounded by more than one LED modules 23, whereby the surrounding by LED-modules 23 may be performed in a cylindrical or spherical orientation around the wrapped bodies 21. The box 20 may further comprise electric motors which may be used for the alignment of the LED-modules 23 and the reflectors used for reflecting the LED-light back onto the tubing 22. In another embodiment of the invention the box may also comprise further valves within the tubing 22 for the feeding or drainage of reactants during the photooxidation reaction of dihydroartemisinic acid (2). In another embodiment of the invention the box 20 may also comprise or have an opening that can be closed off by means of a light proof cover, wherein the opening maybe used for the maintenance of the inner parts of the box, which may comprise the LED module or modules 23, the tubing 22, the transparent body or bodies 21, reflectors or reflecting surface of the inner wall 27, the motors used for alignment or valves within the tubing 22. In another embodiment of the invention the transparent body 21 may be made out of a transparent material belonging to the group comprising: architectural glass, borosilicate glass, calcite, cellophane, cellulose acetate, cer-vit, fused quartz, germanium dioxide, iceland spar, monopotassium phosphate, nitrocellulose, polastarch material, poly(methyl methacrylate), polycarbonate, polyethylene, polyethylene terephthalate, polylactic acid, polyvinyl butyral, pyrex, sitall, soda-lime glass, transparent ceramics, vycor, zerodur, and whereby the transparent material is preferably transparent in the wavelength region necessary for the photooxidation reaction of dihydroartemisinic acid (2), which is even more preferably 420 nm and/or 660 nm. In another preferred embodiment of the invention the transparent material of the transparent body 21 has a transparency of at least >70%, and even more preferably >90% in the wavelength region necessary for the photooxidation reaction of dihydroartemisinic acid (2).

The inventive photochemical reactor is a box made of lightproof or opaque material in which the photochemical reaction is carried out. The box has one small opening so that the tube for the reaction mixture can be inserted into the box and another small opening through which the tube with the reaction mixture after the photochemical reaction can leave the box. At least one light source and preferably LED light sources or LED modules are located or placed or arranged inside the box in order to provide the photochemical activation for the photochemical oxidation of dihydroartemisinic acid (2) with singlet oxygen. The tubing 7 runs in multiple loops through the inside of the box in order to ensure that the reaction mixture containing the starting materials has sufficient time to react so that an as much completed conversion of the dihydroartemisinic acid (2) as possible is obtained. The tubing 7 is preferably wrapped around a transparent body or any transparent support so that the single loops are exposed to the light equally. The transparent body or transparent support is translucent, i.e. is light-transmissive so that the tubing is exposed to light in the most effective manner.

It is within the general skills of a person skilled in the art to determine which flow rate, inside diameter of the tubing 7 and length of the tubing 7 inside the box and/or number of loops around the transparent body, kind of light source, wavelength of the emitted light and, for instance, electrical output of the light source is required to obtain an almost complete conversion of the dihydroartemisinic acid (2) when running through the tubing 7 and through the inside of the box of the photochemical reactor.

Especially preferred are photochemical reactors and continuous flow reactors which allow performing the synthesis of artemisinin in a continuous manner. As explained above, this contrary to a batch-wise reactor design, which only allows performing the reactions batch-wise, i.e. performing the synthesis of artemisinin in batches.

COOLED BOX ASSEMBLY

Another preferred embodiment of the present invention refers to a system which will be referred to herein as cooled box assembly. This flow reactor setup comprises a specific cooled box reactor 30 for the photooxidation reaction and further reactor compartments 34 and 35 for the acid mediated Hock cleavage and the subsequent oxidation. The center piece of the cooled box assembly is the reactor system which comprises additionally compared to the reflective box housing of the box assembly a cooling system capable of cooling the reactor comprising at least a transparent body 21 wrapped by the tubing 22 as described above.

In the cooled box assembly the reactor is immersed into a cooling liquid, preferably with the entire body of the reactor. The cooling liquid is capable of being liquid at low temperatures, preferably below 0° C., more preferably below −10° C., even more preferably below −20° C., yet even more preferably below −50° C. and most preferably below −100° C.

In a preferred embodiment the cooling liquid is a mixture of water and an organic solvent. However, the cooling liquid may also be a fluorinated hydrocarbon or a solution of water and an inorganic salt such as sodium or potassium chloride. In a preferred embodiment the cooling liquid is a mixture of water and ethylene glycol in a ratio 2:3 (v/v). Other preferred ratios are water to ethylene glycol range from 0.5:100 to 4:1. Other preferred organic solvents for preparing a cooling liquid with water are methanol, ethanol, isopropanol, acetone, DMSO and glycerol. The cooling liquid is filled into the main body of the cooled box assembly which can be any suitable containment being water proof and capable of keeping a certain amount of liquid such as a container, a bucket, a tray, a vessel or a bowl, preferably equipped with reflectors or with a reflecting surface on the inner wall. For the cooled box assembly the main body containment is preferably made of aluminum or stainless steel. However, also other materials are suitable such as chromium, molybdenum, silver, gold, lead or alloys thereof.

Further immersed into the cooling liquid is a chiller 33 capable of cooling the liquid from room temperature down to the freezing point of the cooling liquid. Depending on the cooling liquid temperature down to −100° C. can be achieved. Preferable temperature range for the photooxidation reaction range from room temperature to −30° C., more preferably from 10° C. to −25° C., even more preferably from 0° C. to −20° C., yet even more preferably from −10° C. to −20° C., and most preferably from −15° C. to −18° C.

The cooled box assembly as also depicted in FIG. 8 may further comprise a high energy LED module or modules 31 with a corresponding energy source 32. However, it is also possible that the cooled box assembly comprises a LED module or modules 23 as used for the box assembly. The high energy LED module 31 is embedded into one wall of the main body containment 30, preferably the ceiling wall with a defined distance to the reactor being immersed into the cooling liquid. The distance between the LED module 31 and the reactor is preferably between 1 cm and 10 cm, more preferably between 2 cm and 5 cm and most preferably 3 cm. The high energy LED module 31 comprises light-emitting diodes having a preferred light emitting wavelength of 420 nm and/or 660 nm. The setup of the arranged LED's for 31 are within a plane module having an emission-surface within 25×120 $cm^2$ to 50×50 $cm^2$, or even more preferred of at least 44×88 $cm^2$. The emission angle of the diodes ranges from 90° to 150°, and is preferably 120°. The optical output of the high energy LED module 31 is up to 400 W and preferably ranges from 200 to 350 W, and is most preferably 280 W.

After passing through the chilled reactor comprising at least a transparent body 21 wrapped by the tubing 22 the reaction mixture exits the main body containment 30 into a tubing 22a which is preferably larger in diameter than the tubing 22. The diameter of the tubing 22a is preferably 1.5 to 3 fold of the diameter of tubing 22, more preferably 1.8 to 2.5 fold of the diameter of tubing 22, and most preferably 2 fold of the diameter of the tubing 22. The reaction mixture flows through tubing 22a in reactor component 34 being kept at a decreased temperature ranging from 0° C. to 15° C., and preferably being 10° C. In a preferred embodiment the reaction volume kept at the decreased temperature of reactor component 34 is 10 ml. Subsequent to the reactor component 34 there is a reactor component 35 kept at a temperature ranging from 20° C. to 30° C., and preferably kept at room temperature. The reaction volume of the reactor component 35 is preferably 2 to 6 fold of the reaction volume of reactor component 34, more preferably 3 fold of the reaction volume of the reactor component 34.

At the end of the reactor assembly there is provided a back pressure regulator 14 capable of increasing the pressure within the reaction system beneficially influencing the oxygen solubility and thereby the oxygen concentration in the reaction mixture.

According to a preferred embodiment as depicted in FIG. 13 the continuous flow reactor of the cooled box assembly as depicted in FIG. 8 can further comprise an additional pressure regulator 14a at the outlet of the photochemical reactor and a second additional pressure regulator between reactor component 34 and reactor component 35.

Thus, the cooled box assembly of the present invention preferably comprises as shown in FIG. 8
- a feed F4 for dihydroartemisinic acid (2) and trifluoroacetic acid (TFA) and a suitably solvent which can be mixed at an automated two inlet switch valve 13a for regulating the composition of the feed
- a pump 1a and a pressure sensor 5c,
- an oxygen tank 4 being connected to a pressure regulator 3 and a flow control 2 being further connected to a check valve 5b,
- a T-mixer valve 28 where the feed solution of dihydroartemisinic acid and oxygen are mixed,
- a cooled box main containment 30 being filled with a suitable cooling liquid bearing the transparent body 21 wrapped by the tubing 22 in the liquid and the chiller 33,
- a high energy LED module 31 with a suitable energy source 32,
- a tubing 22a having a larger diameter than the reactor tubing 22,
- a reactor compartment 34
- a reactor compartment 35
- a back pressure regulator 14
- an outlet for the reaction mixture.

Specific embodiments of the cooled box assembly are depicted in FIGS. 9A and 9B.

Another embodiment of the invention comprises the continuous separation of artemisinin (6) out of the raw product mixture which is finally produced by the continuous flow reactor. Such raw product mixtures can be separated by usual techniques such as extraction or column chromatography. However it is also possible to implement the separation step into the continuous reactor design of the present invention. Herein the two subsequent methods are preferred:
separation by simulated moving bed chromatography,
separation by continuous crystallization.

Continuous chromatography methods, in particularly simulated moving bed chromatography (SMB chromatography) comprises an arrangement of several columns with two inlet and outlet connections respectively, which are moved in such a fashion to mimic a counter flow of the stationary phase compared to the eluent flow. This enables continuous binary separations in which either the least or the strongest absorbing component can be extracted as pure compound. Solvents and stationary phases can be adjusted for the purification of artemisinin from the crude mixture exiting from a reactor of the present invention after performance of the Hock cleavage upon formation of artemisinin. In a preferred embodiment, the solvent for the simulated moving bed chromatography is a mixture of dichloromethane and hexane (50:50). Also, this method is readily scalable and can be employed for purification on large scale without extensive consumption of solvents.

In the continuous crystallization process, a saturated solution of the crude in a suitable solvent is prepared at elevated temperatures. Cooling while flowing through a tube creates an oversaturated solution, from which upon seeding artemisinin crystallizes onto the surface of the tube. These crystals can be removed from the mixture continuously. Accordingly, the crude mixture containing artemisinin after performing the Hock cleavage exits one of the herein described reactor components and the crude solution is exposed to elevated temperatures, preferably under reduced pressure for removal of solvent. Once a sufficient amount of solvent is removed, and a saturated or almost saturated solution of artemisinin is prepared the solution is led to a further component of the reactor where decreased temperature is applied to the solution. Preferably, not only the temperature is decreased but also crystalline artemisinin seeds are provided. Upon these conditions an oversaturated solution develops out of which crystalline artemisinin will precipitate which can be separated, e.g. by filtration from the crude reaction mixture.

CYLINDER ASSEMBLY

Another preferred embodiment of the present invention refers to a system which will be referred to herein as cylinder assembly. This flow reactor setup comprises a specific cylinder or a double-walled cylinder or even a multiple-walled cylinder being placed around the light source 11 and wherein the solution or mixture of dihydroartemisinic acid flows through that cylinder or within the walls of the doubled-walled or multiple-walled cylinder while being exposed to the light of the light source. Particularly by using a doubled-walled or multiple-walled cylinder the solution or mixture of dihydroartemisinic acid flows more than once past the light source and experiences an increased retention time. Also, between the walls or at one side of and/or around or within the one cylinder a cooling cylinder may be attached such that the solution or mixture of dihydroartemisinic acid may be adjusted to a certain preferred temperature at the outer side of the reactor a cylinder may be attached comprising a second light source such that the solution or mixture of dihydroartemisinic acid can be irradiated from two sides of the cylinder assembly. Further, in case no second light source is incorporated into the cylinder assembly the outer surface of the outer most cylinder is covered to the inside facing the one light source with a reflective material as defined herein. The different cylinders as being arranged around the at least one light source in the middle of the assembly are preferably made of glass, more preferably of pressure proof glass, such that the light can easily be irradiated without significant loss of intensity on the solution running through the cylinder which can further be processed under increased pressure, preferably oxygen pressure.

All other reactor parts of the continuous flow reactor of the cylinder assembly may correspond to the herein described reactor parts in the immersion well assembly, or the box assembly or the cooled box assembly.

DESCRIPTION OF FIGURES

FIG. 11 System diagram of the continuous flow reactor of FIG. 2 further comprising an additional pressure regulator 14a.

FIG. 12 System diagram of the continuous flow reactor of FIG. 5 further comprising an additional pressure regulator 14a.

EXAMPLES

Figure 1:
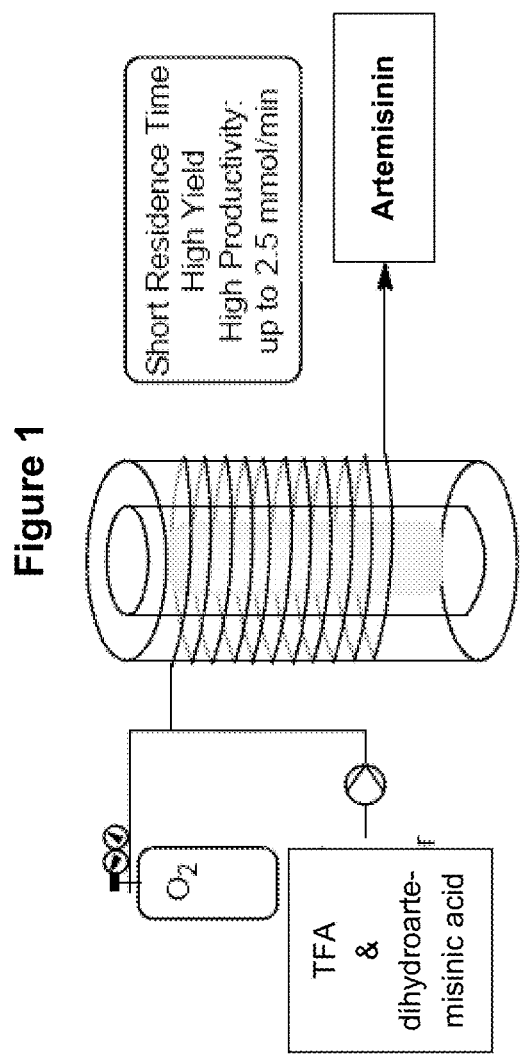
FIG. 1: Schematic drawing of the photochemical reactor for the synthesis of artemisinin according to the "immersion well assembly".
Figure 2:
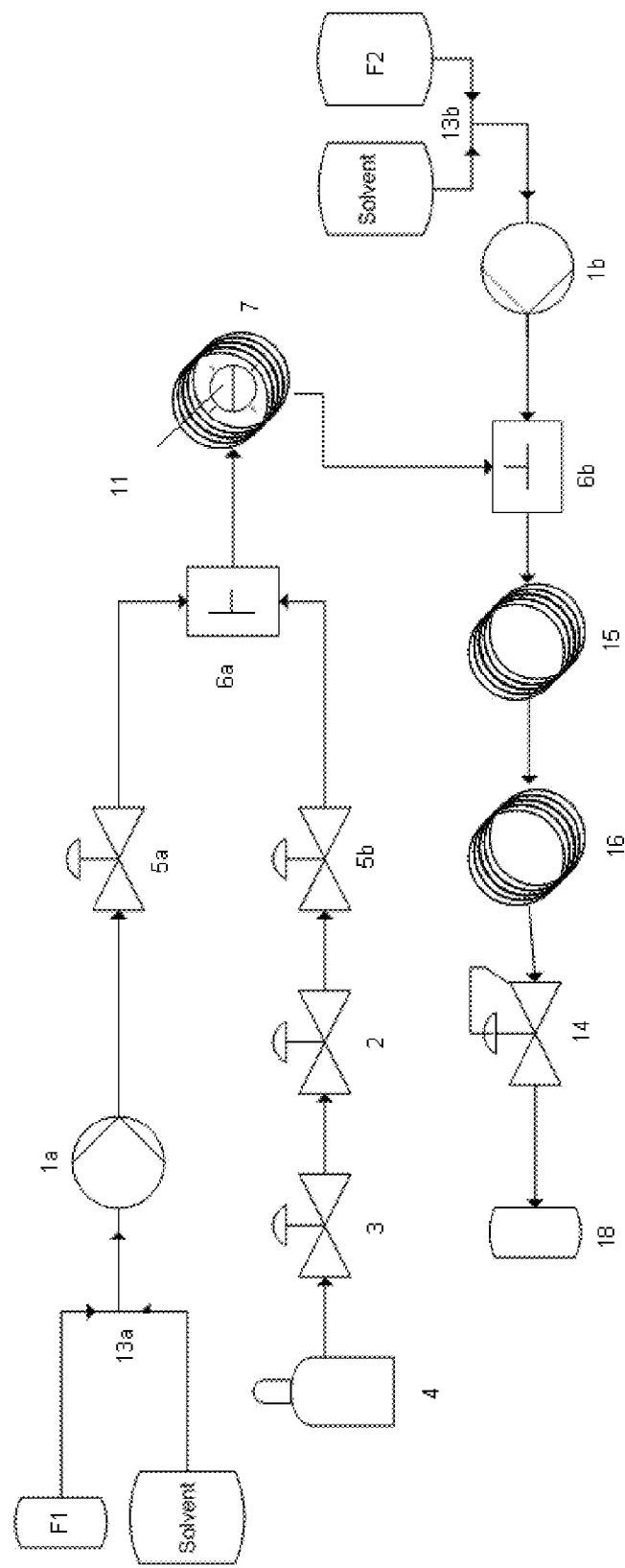
FIG. 2: System diagram of the continuous flow reactor for the synthesis of artemisinin according to the "immersion well assembly".
Figure 3:
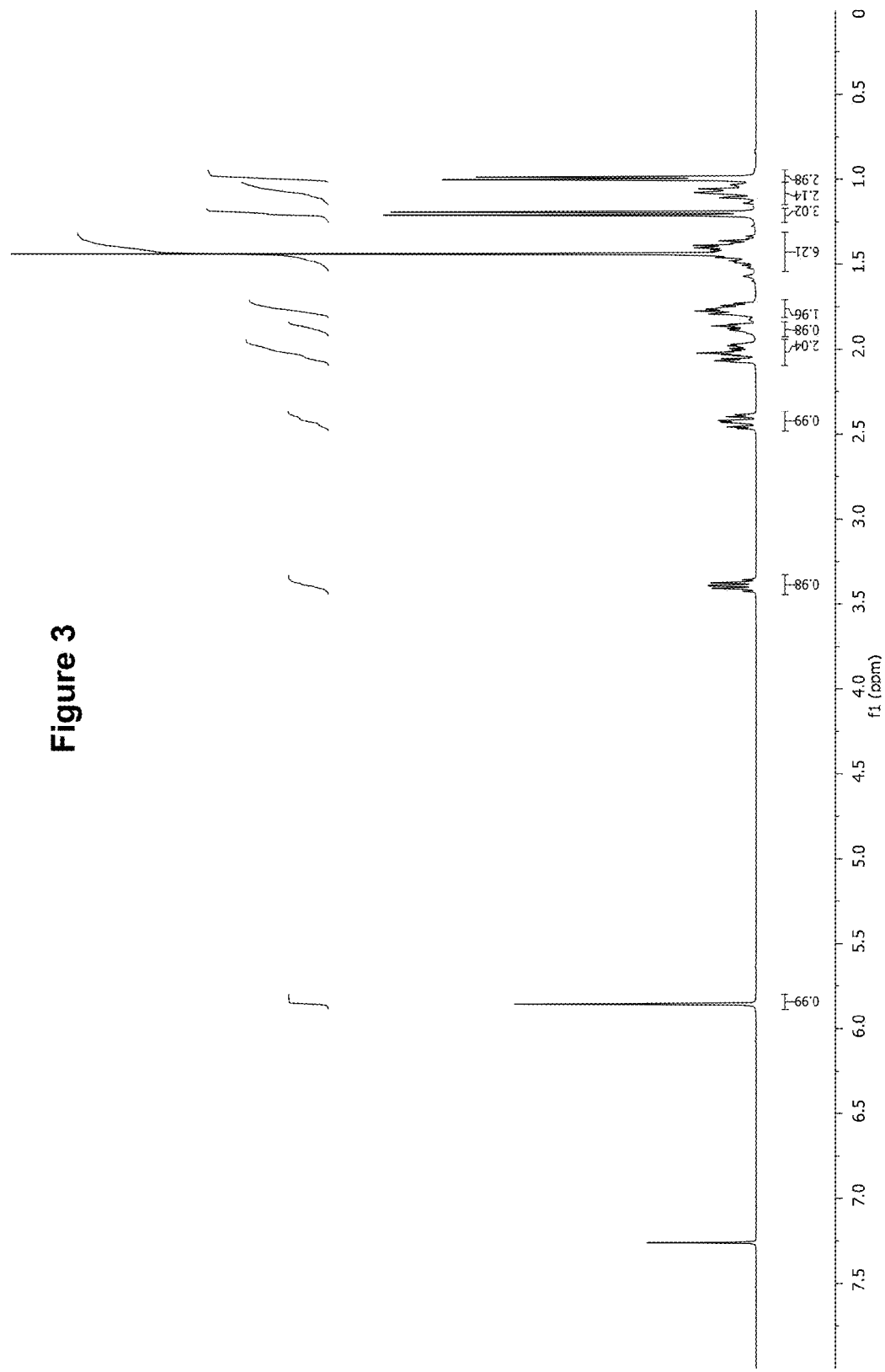
FIG. 3: $^1$H NMR of the produced artemisinin
Figure 4:
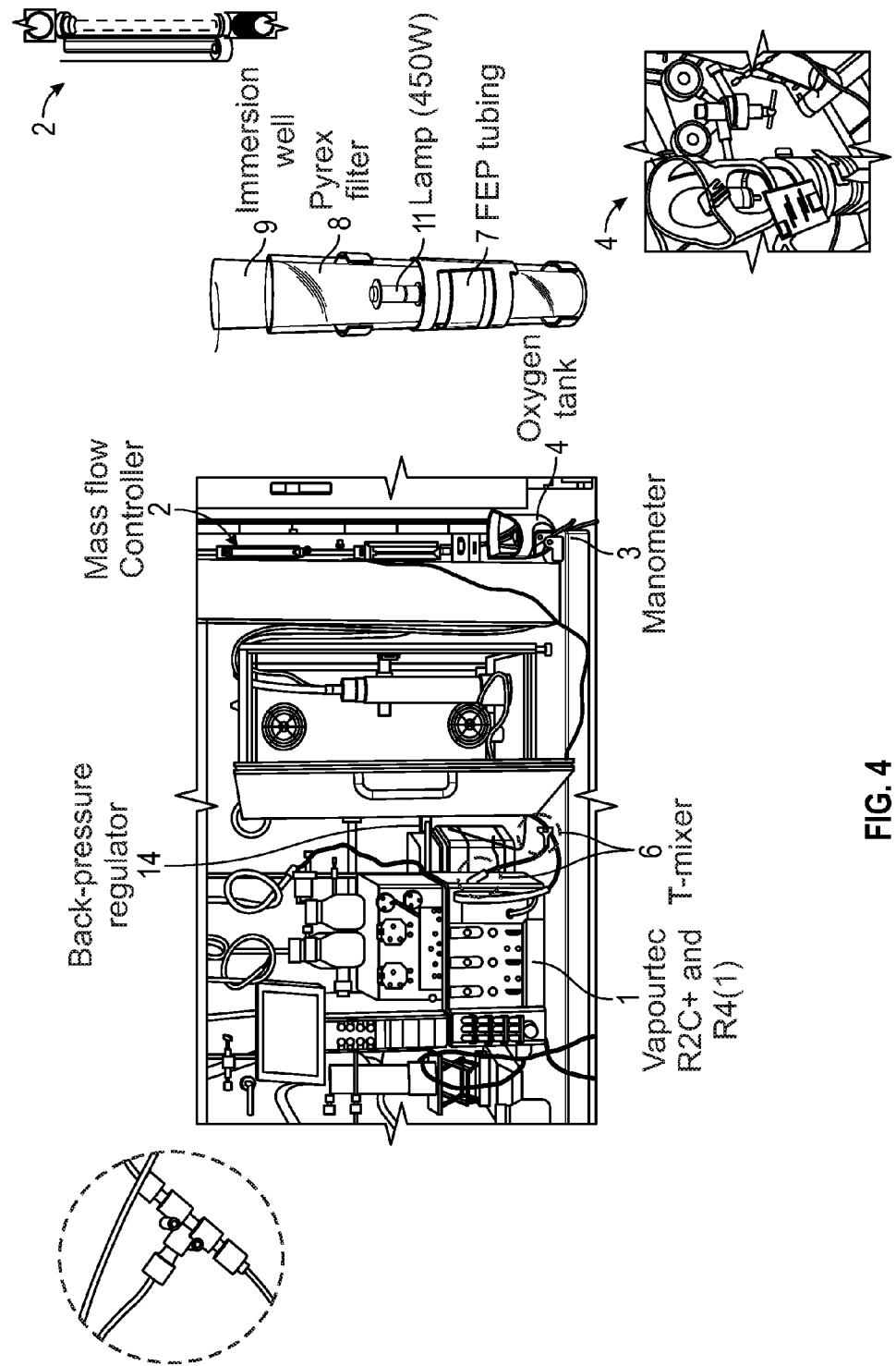
FIG. 4: Flow reactor setup for the synthesis of artemisinin according to the "immersion well assembly".

Methods $^1$H NMR spectra were recorded on a Varian 400-MR spectrometer (at 400 MHz) at ambient temperature. The proton signal of residual non-deuterated solvent (δ 7.26 ppm for CHCl$_3$) was used as an internal reference for $^1$H spectra. Data are reported as follows: chemical shift in parts per million (δ, ppm), multiplicity (s=singlet, d=doublet, t=triplet, q=quartet, qn=quintet, m=multiplet and br=broad), coupling constant reported in Hertz (Hz) and integration. $^{13}$C spectra were recorded on a Varian 400-MR spectrometer (at 101 MHz) at ambient temperature. Chemical shifts are reported in parts per million (δ, ppm). The carbon signal of deuterated solvent (δ 77.16 ppm for CDCl$_3$) was used as an internal reference for $^{13}$C spectra. One exemplary spectrum of artemisinin prepared by a method of the present invention is depicted in FIG. 3.

Infrared (IR) spectra were recorded as thin films on a Perkin-Elmer 1600 FTIR spectrophotometer. Melting points were recorded using an Electrothermal IA 9300 melting point apparatus and are uncorrected. Optical rotations (OR) were measured with a Schmidt & Haensch Unipol L 1000 at a concentration (c) expressed in g/100 mL. High-resolution mass spectra (HRMS) were recorded with an Agilent 6210 ESI-TOF mass spectrometer at the Freie Universitat Berlin, Mass Spectrometry Core Facility.

Analytical thin layer chromatography (TLC) was performed on Kieselgel 60 F254 glass plates pre-coated with a 0.25 mm thickness of silica gel. The TLC plates were visualized with UV light and by staining with an aqueous solution of potassium permanganate (KMnO$_4$) or a mixture of iodine and silica. Column chromatography was performed using Kieselgel 60 (230-400 mesh) silica gel with a typical 50-100:1 weight ratio of silica gel to crude product.

Example 1

Reaction Conditions for Oxidation of Dihydroartemisinic Acid (2)

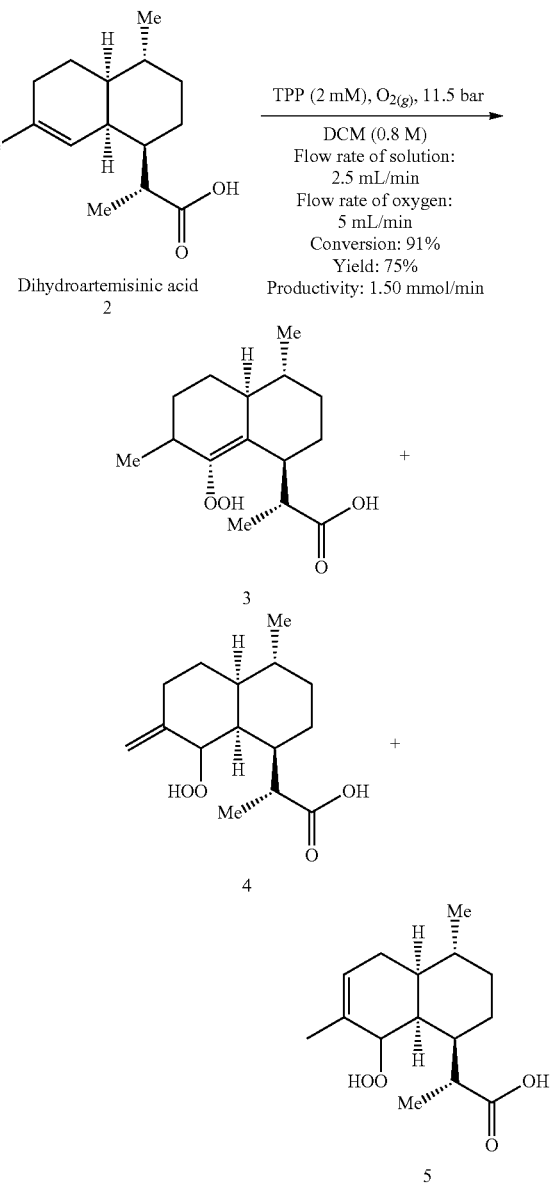

A solution of dihydroartemisinic acid (0.95 g, 4.0 mmol) and tetraphenylporphyrin (6.1 mg, 10 µmol) in dichlo romethane (total volume of the solution: 5.0 mL, volumetric flask) was prepared. The lamp was turned on 30 min prior to the beginning of the experiment. The reactor was flushed with pure dichloromethane (2.5 mL/min) and oxygen (5 mL/min, 11.5 bar) for 5 min. The reagents were then injected at a flow rate of 2.5 mL/min and the flow of oxygen was readjusted to 5 mL/min (11.5 bar). After the injection of the entire solution of dihydroartemisinic acid, the reactor was flushed with pure dichloromethane (2.5 mL/min) to recover all the material. The crude material was concentrated under reduced pressure to remove the dichloromethane affording a mixture of the intermediate products (3), (4) and (5) and TPP as a green solid (1.0856 g). Part of this mixture (200 mg) was dissolved in CDCl$_3$ and mesitylene (103 µL, 0.741 mmol, 98% pure) was added. $^1$H NMR analysis showed a conversion of 91% and a yield of the desired product of 75%.

Example 2

Reaction Conditions for Oxidation of Dihydroartemisinic Acid (2) in Flow and Cleavage of Tertiary Allylic Peroxide (3) in Batch to Obtain Artemisinin (6)

A solution of dihydroartemisinic acid (4) (1.18 g, 5.0 mmol) and tetraphenylporphyrin (12 mg, 20 µmol) in dichloromethane (total volume of the solution: 10.0 mL, volumetric flask) was prepared. The lamp was turned on 30 min prior to the beginning of the experiment. The reactor was flushed with pure dichloromethane (2.5 mL/min) and oxygen (5 mL/min, 11.5 bar) for 5 min. The reagents were then injected at a flow rate of 2.5 mL/min and the flow of oxygen was readjusted to 5 mL/min (11.5 bar). After the injection of the entire solution of (4), the reactor was flushed with pure dichloromethane (2.5 mL/min) to recover all material. The reaction mixture was collected in a round bottom flask and was cooled down to 0° C. Oxygen was bubbled into the reaction mixture at atmospheric pressure. After 2 min of bubbling, TFA (0.19 mL, 2.5 mmol, 0.5 eq.) was added drop wise. The resulting mixture was stirred at 0° C. for 2 h, while maintaining the oxygen bubbling. Then, the reaction was quenched with a saturated aqueous solution of NaHCO$_3$. The resulting biphasic mixture was stirred at room temperature until disappearance of the green colour. The phases were separated and the aqueous phase was extracted with dichloromethane (3 times). The combined organic layers were dried over anhydrous Na$_2$SO$_4$, filtered and concentrated under reduced pressure. Purification over silica gel (5%-20% EtOAc in cyclohexane) afforded artemisinin (0.707 g, 50%) as a yellow solid.

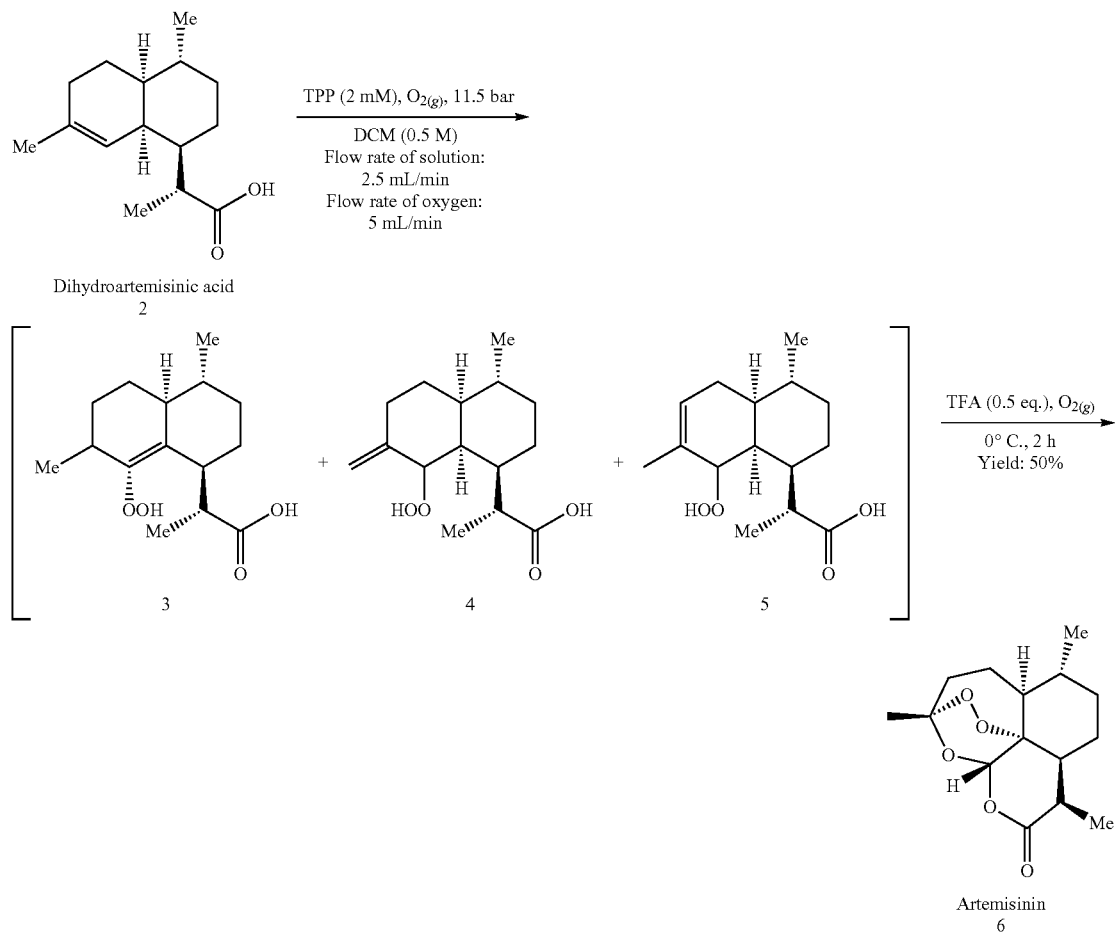

Example 3

Reaction Conditions for Oxidation of Dihydroartemisinic Acid (2) in Continuous Flow, Followed by the Cleavage of Tertiary Allylic Peroxide (3) in Continuous Flow to Obtain Artemisinin (6) (Sequential Process)

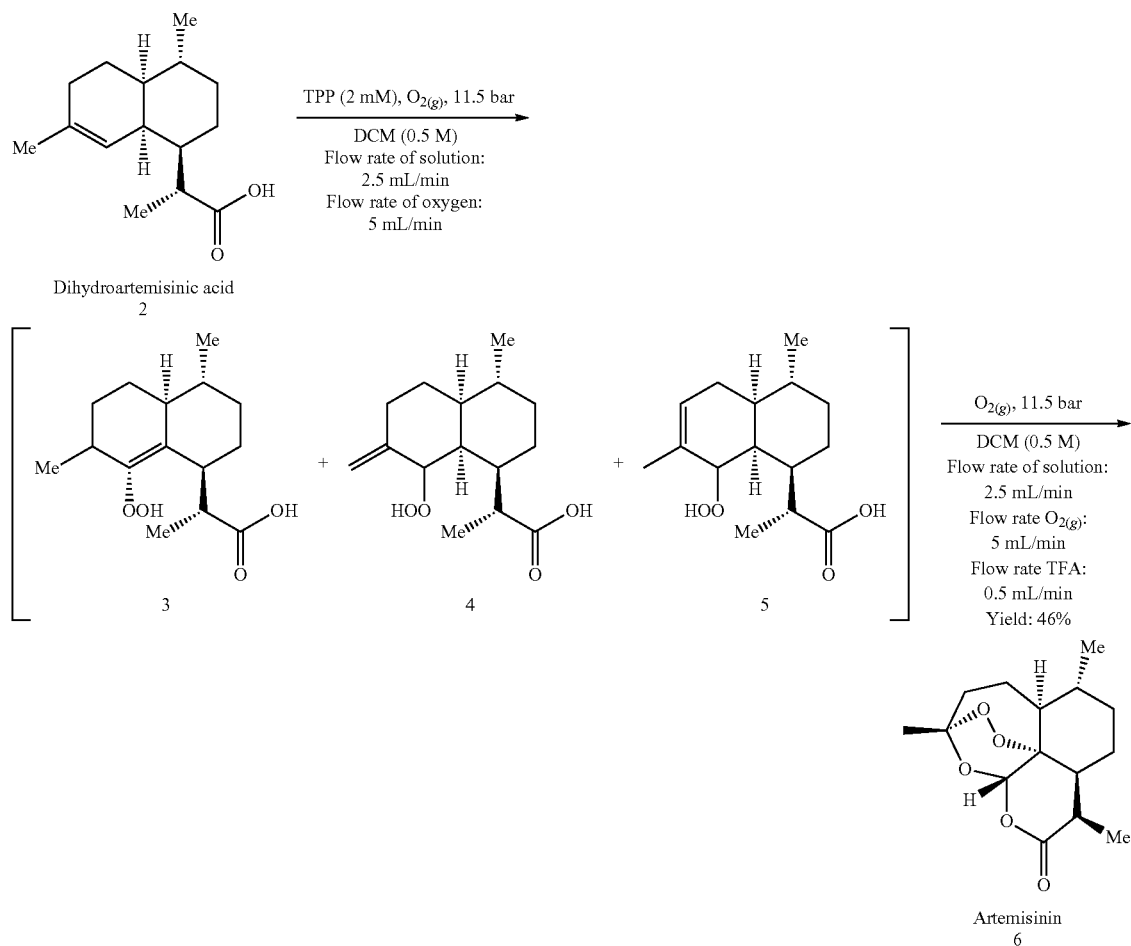

A solution of dihydroartemisinic acid (1.18 g, 5.0 mmol) and tetraphenylporphyrin (12 mg, 20 μmol) in dichloromethane (total volume of the solution: 10 mL, volumetric flask) was prepared. The lamp was turned on 30 min prior to the beginning of the experiment. The reactor was flushed with pure dichloromethane (2.5 mL/min) and oxygen (5 mL/min, 11.5 bar) for 5 min. The reagents were then injected at a flow rate of 2.5 mL/min and the flow of oxygen was readjusted to 5 mL/min (11.5 bar). After the injection of the entire solution of (1), the reactor was flushed with pure dichloromethane (2.5 mL/min) to recover all the material. The crude material was concentrated under reduced pressure to remove the dichloromethane affording a mixture of (3), (4), (5) and TPP as a green solid.

The crude mixture was dissolved in DCM (total volume of the solution: 10 mL, volumetric flask). The crude mixture was injected at a flow of 2.5 mL/min and combined with oxygen (5 mL/min, 11.5 bar) and a solution of TFA (1.9 mL of TFA in 18.1 mL of DCM) at a flow rate of 0.5 mL/min with the help of a cross mixer. The reaction mixture was passed a PTFE reactor composed of 32 mL loop at rt and 10 mL loop heated at 60° C. The crude material was collected in a flask containing a saturated aqueous solution of NaHCO₃. The resulting biphasic mixture was stirred at room temperature until green colour disappeared. The phases were separated and the aqueous phase was extracted three times with dichloromethane. The combined organic layers were dried over anhydrous Na₂SO₄, filtered and concentrated under reduced pressure. Purification over silica gel (5%-20% EtOAc, in cyclohexane) afforded artemisinin (0.66 g, 46%) as a yellow solid.

Example 4

Reaction Conditions for the Synthesis of Artemisinin (6) in Continuous Flow

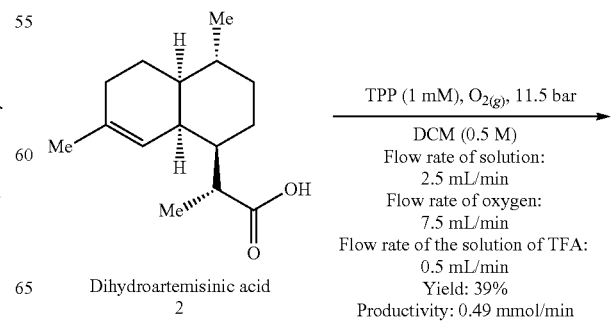

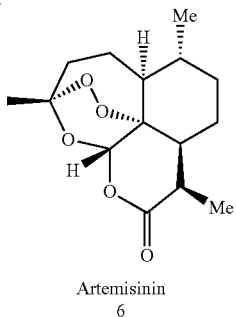

Artemisinin
6

A solution of dihydroartemisinic acid (2.95 g, 12.5 mmol) and tetraphenylporphyrin (15 mg, 0.02 mmol) in dichloromethane (total volume of the solution: 25 mL, volumetric flask) and a solution of trifluoroacetic acid (1.9 mL, 25 mmol) in dichloromethane (18.1 mL) were prepared and given into their respective feed. The Hg lamp was turned on 30 min prior to the beginning of the experiment and the second portion of the photochemical reactor was heated at 60° C. The photochemical reactor was flushed with pure dichloromethane (2.5 mL/min), dichloromethane (0.5 mL/min) and oxygen (7.5 mL/min, 11.5 bar) for 10 min. The reagents were then injected via their respective feed at a flow rate of 2.5 mL/min and the oxygen flow was readjusted to 7.5 mL/min (11.5 bar). Both streams joined in the first mixer. From there they entered the photochemical reactor. The TFA solution was injected at the exit of the photochemical reactor into a second mixer at a flow rate of 0.5 mL/min and the resulting mixture was pushed into the thermal reactor. The crude material containing the produced artemisinin was collected in a flask containing a saturated aqueous solution of $NaHCO_3$. The resulting biphasic mixture was stirred at room temperature until the green color disappeared. Phases were separated and the aqueous phase was extracted with dichloromethane (3 times). The combined organic layers were dried over anhydrous $Na_2SO_4$, filtered and concentrated under reduced pressure. Purification over silica gel (5%-20% EtOAc, in cyclohexane) afforded artemisinin (1.36 g, 39%) as a off-white solid. Further purification by recrystallization in cyclohexane afforded white needles. $^1$H NMR (400 MHz, $CDCl_3$) δ 5.86 (s, 1H), 3.40 (dq, J=7.3, 5.4 Hz, 1H), 2.47-2.39 (m, 1H), 2.08-1.98 (m, 2H), 1.91-1.86 (m, 1H), 1.81-1.74 (m, 2H), 1.51-1.34 (m, 3H), 1.45 (s, 3H), 1.21 (d, J=7.3 Hz, 3H), 1.11-1.04 (m, 2H), 1.00 (d, J=6.0 Hz, 3H). The $^1$H NMR spectrum of the obtained artemisinin (6) is shown in FIG. 3. Mp=153-154° C. $[\alpha]_D^{20}$+66.3° (c 0.97, $CHCl_3$). $^{13}$C NMR (101 MHz, $CDCl_3$) δ 172.2, 105.5, 93.9, 79.6, 50.2, 45.1, 37.7, 36.1, 33.8, 33.0, 25.4, 25.0, 23.6, 19.9, 12.7. IR (film) ν 2960, 2933, 2860, 1731, 1112, 991 cm$^{-1}$. HRMS calcd for $C_{15}H_{22}O_5$ (M+) 282.1467. found 282.1463. MS (EI) m/z 282 (1) [M$^-$], 250 (5), 192 (70), 150 (40), 55 (63), 43 (100). Spectral data were in agreement with published data (Yadav, J. S.; Satheesh, B.; Sabitha, G. *Tetrahedron Lett*. 2003, 44, 387-389.).

Example 5

Flow Reactor Setup for the Synthesis of Artemisinin According to Example 4

The flow reactor setup for the synthesis of artemisinin (6) consists of a feed F1 for a solution of dihydroartemisinic acid (2), an automated two inlet switch valve 13a for regulating the composition of the feed for the solution of dihydroartemisinic acid (2), allowing for rapid switching from pure solvent to the solution containing the dissolved dihydroartemisinic acid, a first HPLC pump 1a (Vapourtec, R2C+ unit) downstream to switch valve 13a, pumping the dihydroartemisinic acid (2) solution with a throughput of 2.5 mL/min to the first ETFE T-mixer 6a (IDEX Health and Science, P-632) for mixing the dihydroartemisinic acid (2) solution and the oxygen, a first check-valve 5a (IDEX Health and Science, inline check-valve CV-3010) between the first HPLC pump 1a and the mixer 6a, a mass flow controller 2 (Influx, SV1B5-Al05, allowing control of the oxygen flow rate from 5-90 cm$^3$/min) connected to a manometer 3 fixed on an oxygen tank 4 (Air Liquide, $O_2$ 99.995% pure), thus generating a steady oxygen flow of 7.5 mL/min, another check valve 5b (IDEX Health and Science, inline check-valve CV-3010) between the mass flow controller 2 and the first mixer 6a, multiple loops of FEP tubing 7 (20 mL, IDEX Health & Science, fluorinated ethylene polymer 1520, natural color, outside diameter (OD) 1/16 in and inside diameter (ID) 0.030 in) wrapped tightly around a Pyrex filter 8 (inner diameter 4.5 cm and wall thickness 0.2 cm) which surrounds the quartz immersion well 9 cooled by a thermostat 10 (Huber, Unistat 360), a medium pressure Hg lamp 11 (Ace Glass, UV 450 immersion lamp, 5 in arc, radial lead, 7825-34), a power supply 12 for photochemical lamp 11 (Ace Glass, 7830), a second ETFE T-mixer 6b IDEX Health and Science, P-632), a first PTFE reactor 15 (11 mL, Omnifit, outside diameter (OD) 1/16 in and inside diameter (ID) 0.8 mm), a second PTFE reactor at room temperature 16 (5 mL, Vapourtec), a third heated (60° C.) PTFE reactor 17 (10 mL, Vapourtec, R4 unit) and a collection flask 18 for collecting the synthesized artemisinic acid. A feed F2 for the TFA solution is regulated via an automated two inlet switch valve 13b for regulating the composition of the feed for the TFA solution, allowing for rapid switching from pure solvent to the TFA solution. A second HPLC pump 1b (Vapourtec, R2C+ unit) pumps TFA with a throughput of 0.5 mL/min to into the second mixer 6b disposed at the outlet of the tubing 7 of the photochemical reactor. There the TFA is reacted with the products of the photochemical reactor process. A back-pressure regulator 14 of 2.2 bar (Vapourtec) was installed in order to increase the internal pressure of the system. FEP tubing was selected for its high transmittance and stability in the UV-vis light range, its flexibility and its high chemical resistance. The 2 mm thick Pyrex filter was essential to absorb wavelengths below 300 nm, to prevent degradation of the tubing, and to avoid any undesired side reactions involving short wavelength light. The temperature in the tube during the reaction is estimated to range from 25 to 30° C., based on temperature measurements taken between the cooling jacket and the tube. For safety reasons, the lamp was placed inside an aluminum box for blocking UV irradiation. Two fans were installed for additional cooling.

Example 6

Synthesis of Hydroperoxide (3) in Continuous Flow Using the Box Assembly

Figure 5:
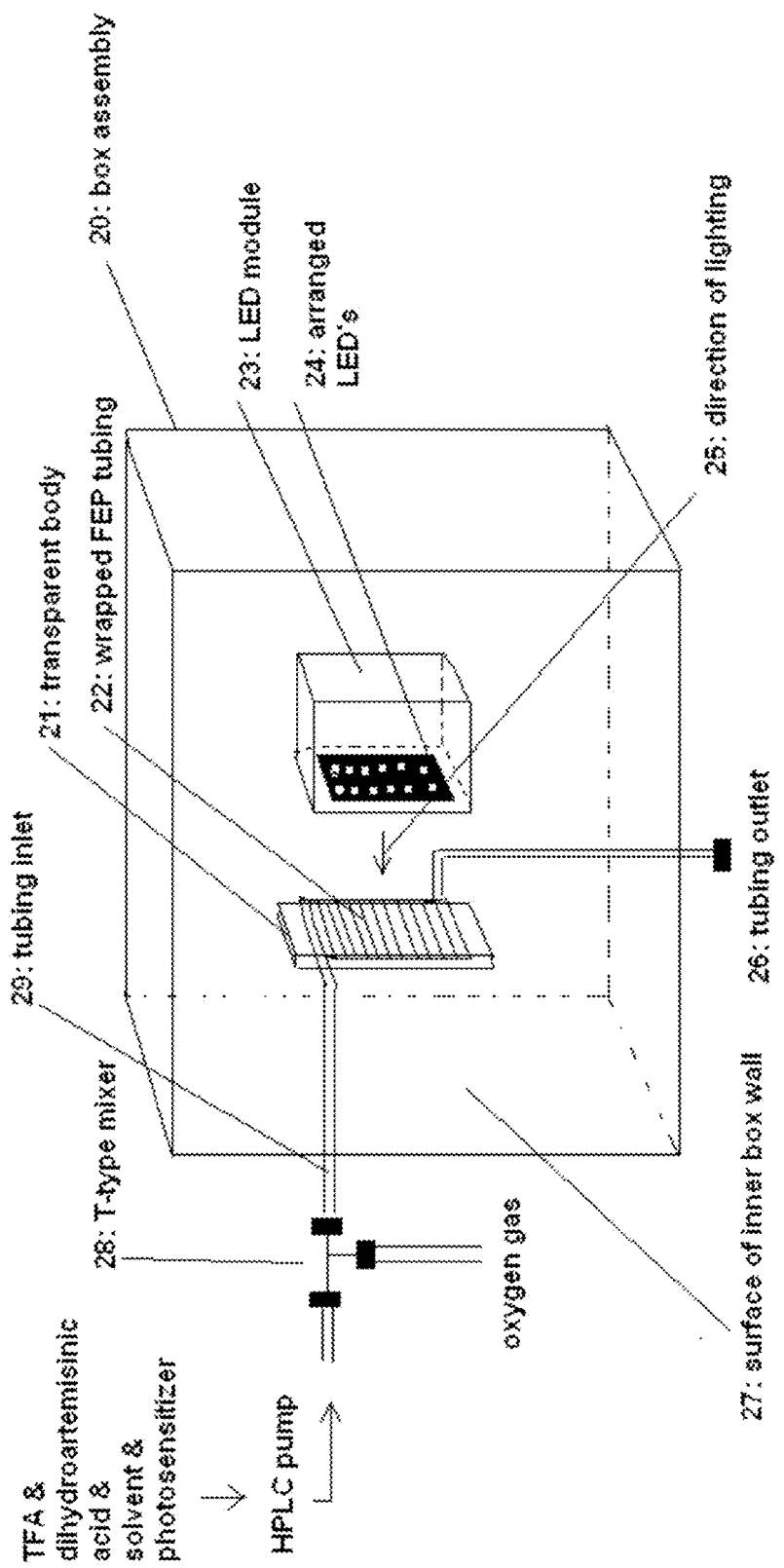
FIG. 5: Schematic drawing of "box assembly" setup of the continuous flow reactor.
Figure 6:
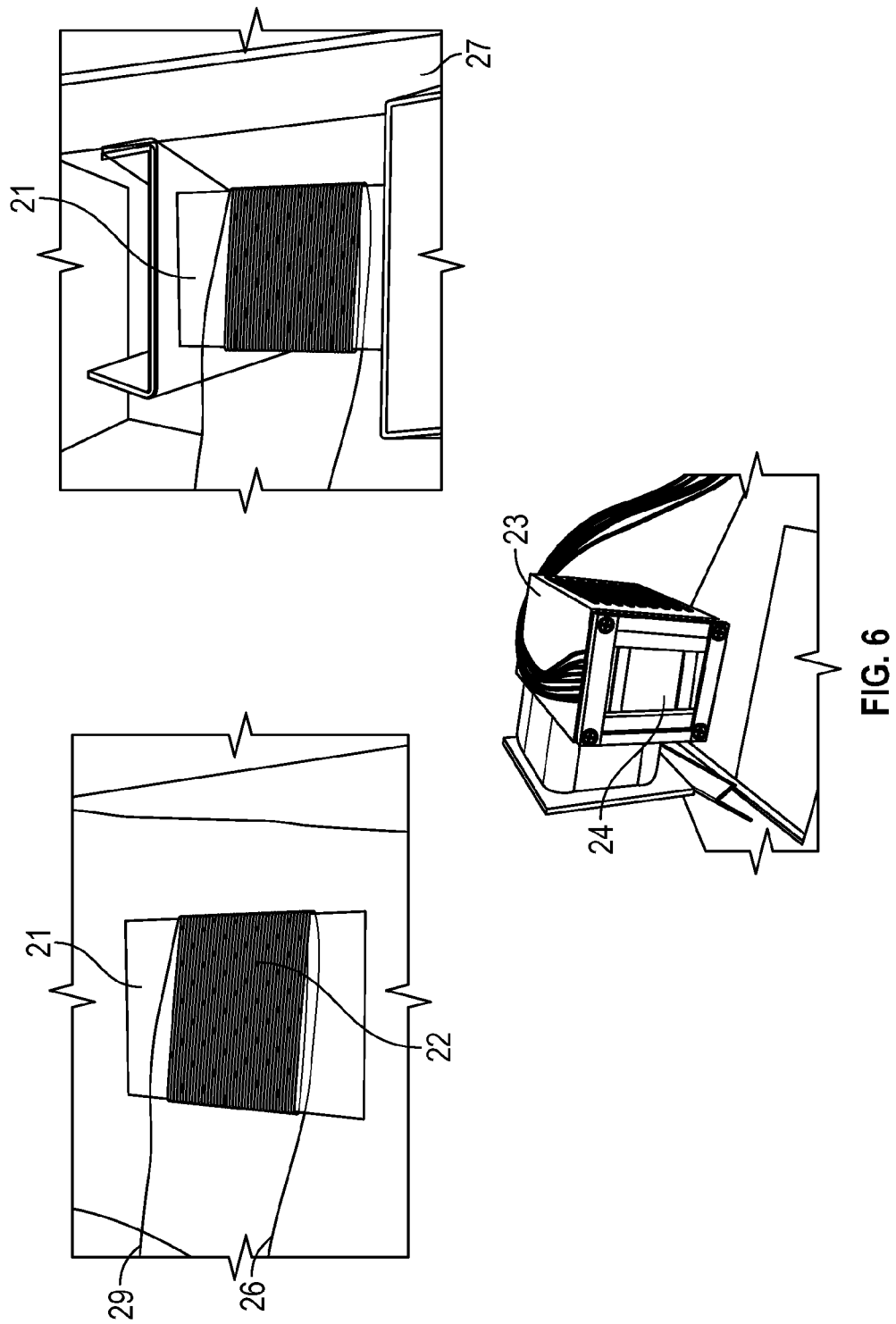
FIG. 6: Parts of the "box assembly" setup of the continuous flow reactor.
Figure 7:
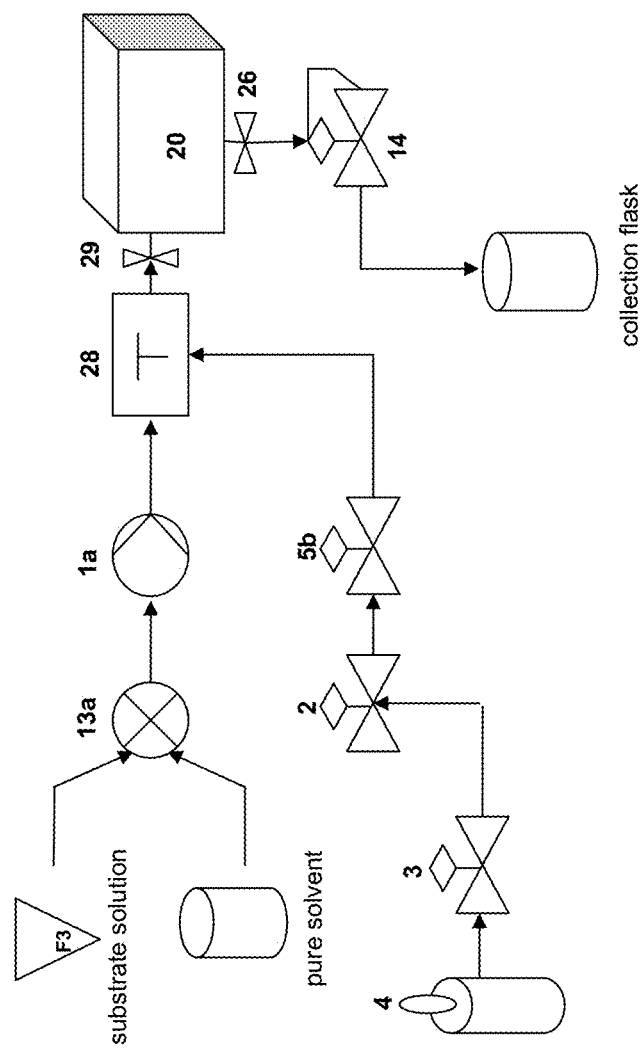
FIG. 7: System diagram of the continuous flow reactor for the synthesis of artemisinin according to the "box-assembly".
Figure 8:
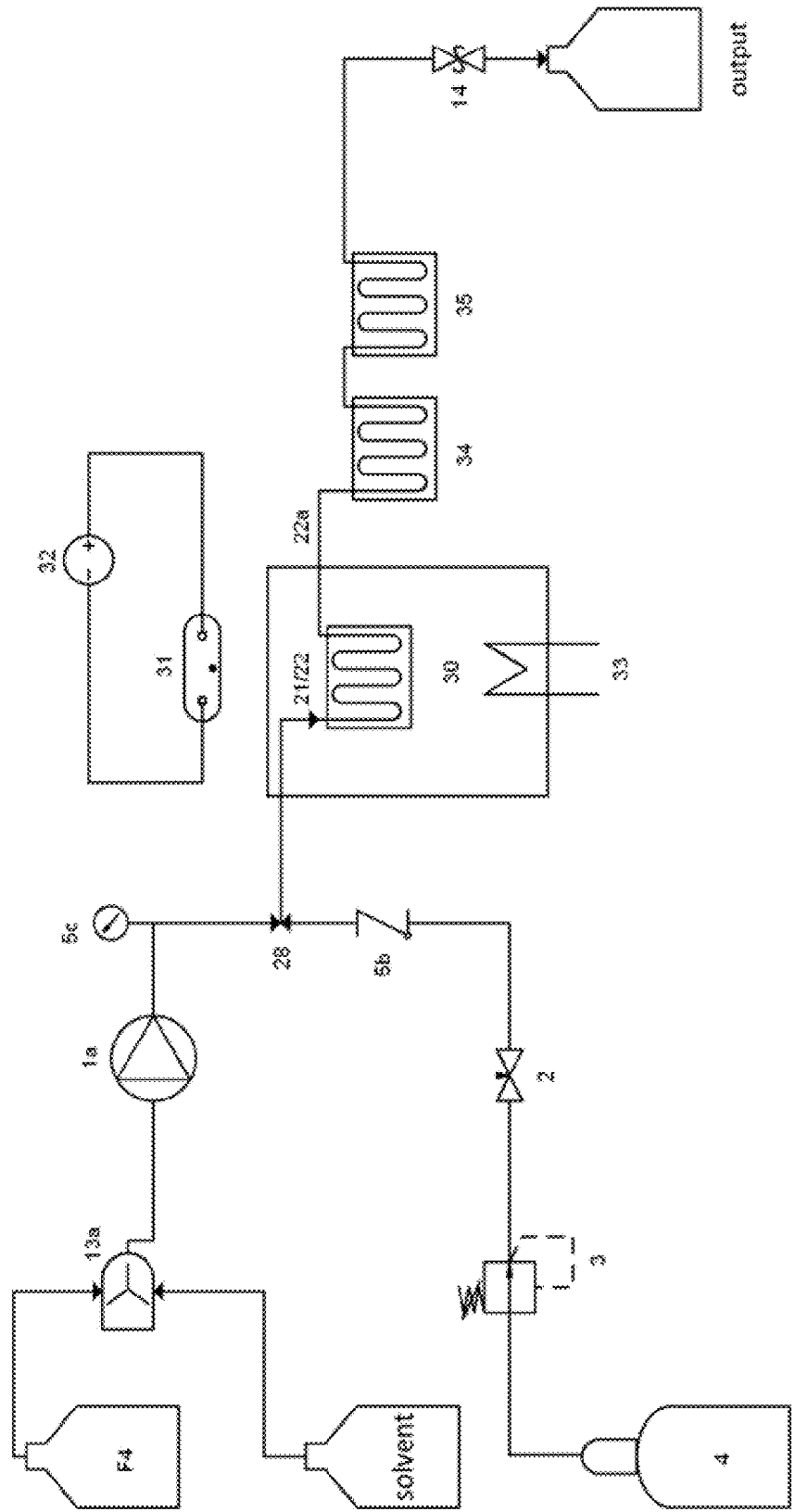
FIG. 8 System diagram of the continuous flow reactor for the synthesis of artemisinin according to the "cooled box assembly".
Figure 9A:
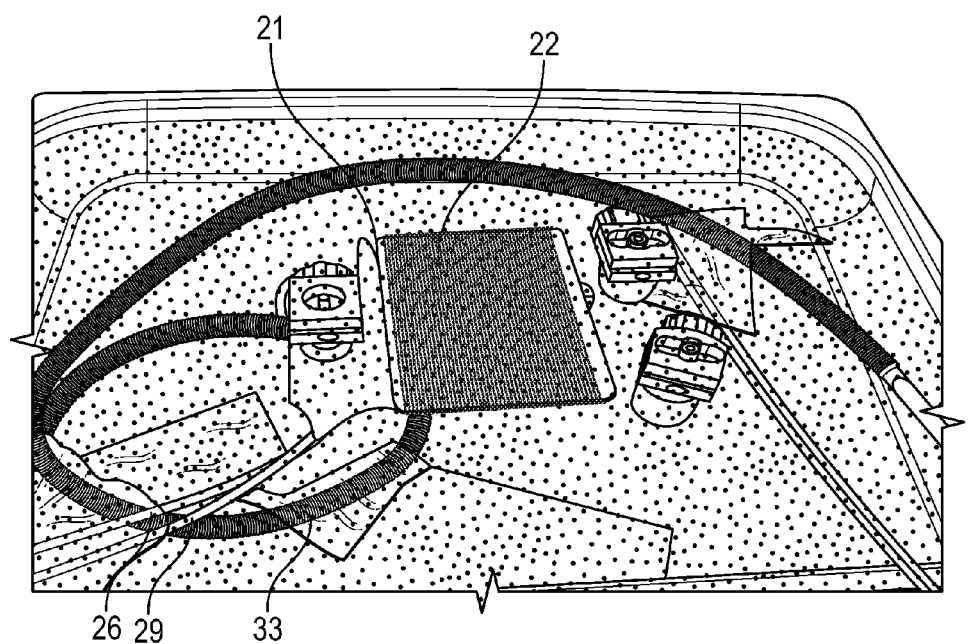
FIG. 9: Parts of the "cooled box assembly" setup of the continuous flow reactor.
Figure 9B:
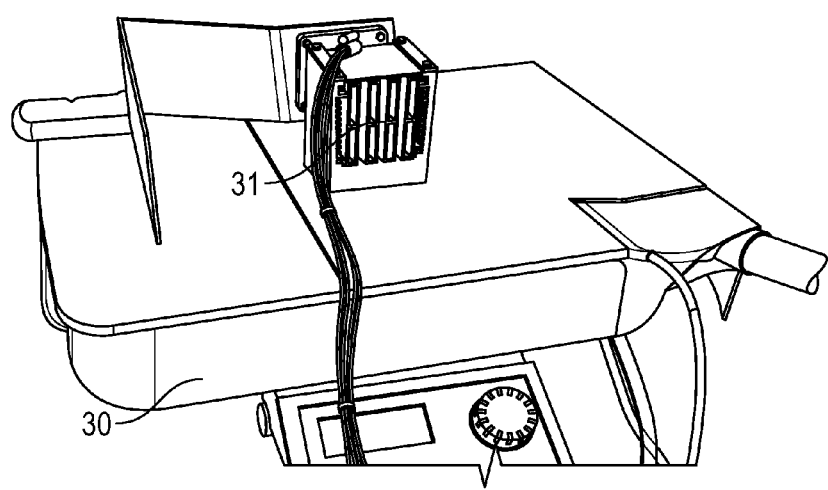

The flow reactor setup (FIGS. 5 and 7) for the synthesis of hydroperoxide (3) consists of a feed F3 for a solution of dihydroartemisinic acid (2), a pumping unit analogously to example 5 (consisting of an automated two inlet switch valve 13a for regulating the composition of the feed for the solution of dihydroartemisinic acid (2), allowing for rapid switching from pure solvent to the solution containing the dissolved dihydroartemisinic acid, a HPLC pump 1a (Vapourtec, R2C+ unit) downstream to switch valve 13a), pumping the dihydroartemisinic acid (2) solution with a throughput of 1.25 mL/min to a ETFE T-mixer 28 (IDEX Health and Science, P-632) for mixing the dihydroartemisinic acid (2) solution and the oxygen, a mass flow controller 2 (Influx, SV1B5-Al05, allowing control of the oxygen flow rate from 5-90 cm$^3$/min) connected to a manometer 3 fixed on an oxygen tank 4 (Air Liquide, $O_2$ 99.995% pure), thus generating a steady oxygen flow of 5 mL/min, a check valve 5b (IDEX Health and Science, inline check-valve CV-3010) between the mass flow controller 2 and the mixer 28, a photochemical reactor comprising the mixer and a tubing inlet 29, consisting of multiple loops of FEP tubing 22 (3.8 mL, IDEX Health & Science, fluorinated ethylene polymer 1520, natural color, outside diameter (OD) 1/16 in and inside diameter (ID) 0.030 in) wrapped tightly around a transparent body 21 (polycarbonate plate, size 9.0×14.0 cm$^2$) which is irradiated by an arrangement of 60 High Power LEDs 24 combined in an LED module 23 emitting at 420 nm (OSA Opto Lights, 72 W electrical power, cooled by a fan, emission area 2.5×2.5 cm$^2$) or at 660 nm (OSA Opto Lights, 46 W electrical power, cooled by a fan, emission area 2.5×2.5 cm$^2$), electronics for supplying a constant current to the LED module (OSA Opto Lights), a power supply (Manson HCS-3202) and a back-pressure regulator of 6.9 bar (IDEX Health and Science) installed after the tubing outlet 26 in order to increase the internal pressure of the system. Because the LED module does not emit UV-radiation which would lead to undesired side reactions, additional filters are not necessary. The wrapped FEP tubing 22 was irradiated directly by the LED module 23, which was installed in a distance of 3 cm in front of the transparent body 21. For maximum efficiency, the tubing was irradiated in a box covered with reflective material 27 (aluminium foil). No additional cooling system for the photochemical reactor was installed. When using the LED module emitting at 420 nm, the feed F3 was a solution of dihydroartemisinic acid at a concentration of 0.5 mol/L and the photosensitizer tetraphenylporphyrin at a concentration of 1 mmol/L in dichloromethane (2.95 g dihydroartemisinic acid and 15 mg tetraphenylporphyrin, total volume 25 mL, volumetric flask), whereas the photosensitizer was methylene blue instead of tetraphenylporphyrin at a concentration of 1 mmol/L when using the LED module emitting at 660 nm (2.95 g dihydroartemisinic acid and 8 mg methylene blue, total volume 25 mL, volumetric flask). The feed was introduced at a flow rate of 1.25 mL/min and the oxygen flow adjusted to 5 mL/min, resulting in a nearly complete conversion of 99% yielding 72% of the desired hydroperoxide (3) with a selectivity of 73% (LED module emitting at 420 nm). When increasing the flow rate, a higher productivity is achieved, however at the expense of the high conversion, as shown in Table 3:

TABLE 3

| flow rate feed F3 | | flow rate$^{-1}$ | conversion | yield | | |
|---|---|---|---|---|---|---|
| mL/min | mmol/min | min mmol$^{-1}$ | | mmol/min | hydro-peroxide 3 | selec-tivity |
| 5 | 2.5 | 0.4 | 51.4% | 1.29 | 36.7% | 71.3% |
| 2.5 | 1.25 | 0.8 | 82.9% | 1.04 | 59.2% | 71.4% |
| 1.75 | 0.875 | 1.143 | 90.3% | 0.79 | 66.7% | 73.9% |
| 1.25 | 0.625 | 1.6 | 99.3% | 0.62 | 72.7% | 73.2% |

For obtaining artemisinin, the product stream leaving the photochemical reactor at the tubing outlet 26 can be mixed with a solution of trifluoroacetic acid at a concentration of 1.875 mol/L in dichloromethane (1.9 mL trifluoroacetic acid in 18.1 mL dichloromethane) and reacted in a thermal reactor, analogously as described in example 5, injecting the trifluoroacetic acid solution at a flow rate of 0.25 mL/min. Alternatively trifluoroacetic acid can already be added to the feed solution F3 at a concentration of 0.375 mol/L.

Example 7

Temperature Dependence on Photooxidation in Continuous Flow Using the Cooled Box Assembly For screening the temperature dependence, a solution of dihydroartemisinic acid (0.5 M, DHAA) and tetraphenylporphyrin (1 mM, TPP) in DCM was prepared, using benzoic acid as internal standard. 5 mL of this solution (1.25 mL/min) and oxygen (5 mL/min) were injected with the vapourtec system into a photochemical reactor (3.8 mL, inner diameter 0.03 inch, 12 W (light output) LED lamp emitting at 420 nm). To cool the photochemical reactor, it was immersed in a cooled bath. The temperature remained constant during the experiment. Additionally, a short reaction time without cooling was investigated, whereby the temperature increased only slightly to 30-40° C. After an extended irradiation time without cooling, the photochemical reactor became very hot (60-80° C.). A back pressure regulator (5 bar) was used at the end of the system. Concentration of the residual starting material and the peroxides was determined by NMR and conversion and selectivities calculated.

The conversion of the starting material DHAA was nearly complete in all cases, with conversion dropping slightly with decreasing temperature, as shown in Table 4 below. For a long reaction time without cooling, the decreased conversion is probably indeed related to the enhanced temperature. The desired peroxide is always the major product. However, lower temperature helps in shifting the ratio of the different peroxides towards the preferred hydroperoxide (3).

Besides the 3 photooxidation products it is also worth considering the amount of other side products. In this respect, temperature has a pronounced effect and a low temperature of −18° C. can decrease the amount of side products to 5% (Table 4). At this temperature, a maximum selectivity of 82% for the desired peroxide is obtained. It is therefore worth to cool the reactor for the photooxidation step in order to obtain a higher yield of artemisinin and less side products, simplifying purification as well.

TABLE 4

| | | selectivities | | | |
|---|---|---|---|---|---|
| temperature | conver-sion | desired peroxide (3) | cyclizing peroxide (4) | non-cyclizing peroxide (5) | other byproducts |
| 60-80° C. | 86% | 62% | 10% | 5% | 24% |
| 30-40° C. | 99% | 73% | 12% | 5% | 10% |
| 20° C. | 92% | 77% | 11% | 5% | 7% |
| 0° C. | 93% | 79% | 11% | 3% | 7% |
| −18° C. | 86% | 82% | 10% | 3% | 5% |

Example 8

Solvent Effects on the Acid Mediated Cleavage

The effect of different solvents was screened using a stock solution of the photooxidation products with TFA as acid. As stock solution, a 20 w % solution of the photooxidation products in DCM was prepared. 4.5 mL of various solvents were filled in vials and after addition of 0.5 eq TFA oxygen was bubbled through (7.5 mL/min) under stirring. After 2 min, 0.5 mL of the stock solution was added and $O_2$ bubbling continued for 20 minutes. The yield of artemisinin (referring to the initial amount of desired peroxide) and the concentration of the major byproducts were evaluated by NMR. In all cases full conversion of the hydroperoxide was observed. In polar aprotic solvents only a low yield of artemisinin was obtained. Here a lot of byproducts, mainly the 5-member lactone (7) but also the aldehyde (9), were formed. Decreasing the polarity is beneficial, as the amount of byproducts is drastically reduced.

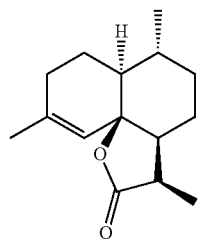

5-member lactone (7)

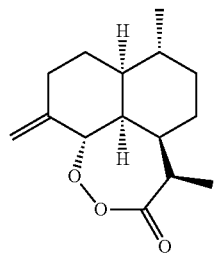

cyclized peroxide (8)

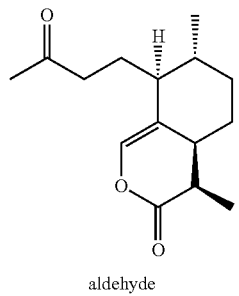

aldehyde (9)

TABLE 5

| solvent | artemisinin (6) | 5-member lactone (7) | cyclized peroxide (9, in % of initial desired peroxide) |
|---|---|---|---|
| acetonitrile | 39% | 36% | 7% |
| DCM | 69% | 17% | 10% |
| toluene | 81% | 7% | 8% |
| cyclohexane | 76% | 6% | 8% |
| benzotrifluoride | 78% | 11% | 9% |
| 1,3-bis(trifluoromethyl)benzene | 82% | 8% | 9% |
| hexafluorobenzene | 81% | 6% | 9% |
| perfluorooctane*) | 40% | 0% | 10% |

*)phase separation occurred

Fluorinated solvents were evaluated as well, as they are characterized by high oxygen solubility and long lifetime of singlet oxygen, which is beneficial for the first photooxidation step. For the acid catalyzed reaction fluorinated aromatic compounds perform well concerning artemisinin yield and prevention of byproducts. Starting material and products were soluble in these solvents. Perfluorooctane however is not suitable, as even upon heating no homogeneous mixture was achieved. The danger arising from the combination of a flammable solvent and oxygen is less dramatic when working in flow, as only small amounts of oxygen are present in the microreactor when efficient ventilation is installed.

Example 9

Temperature Effects on the Acid Mediated Cleavage

Figure 10:
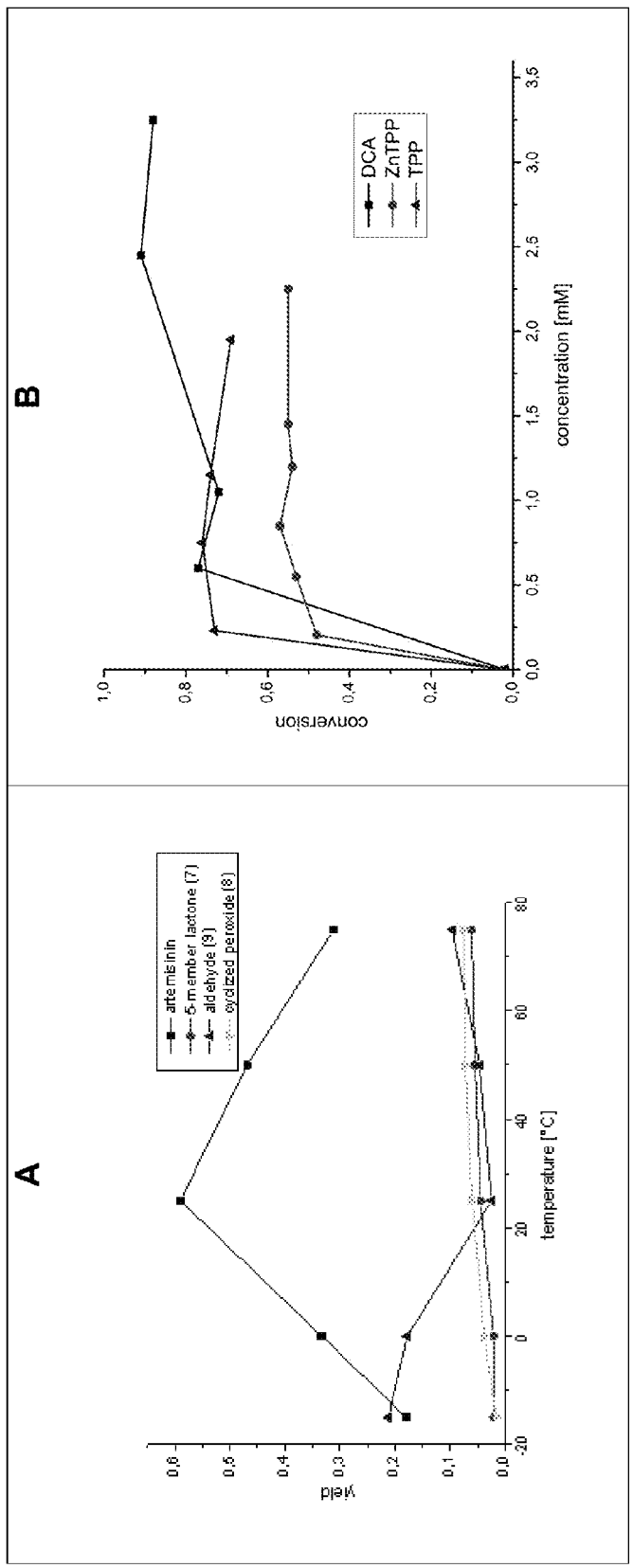
FIG. 10 (A) Diagram on the temperature dependence of the acid mediated cleavage, and (B) diagram on conversion dependency on the photosensitizer concentration.
Figure 11:
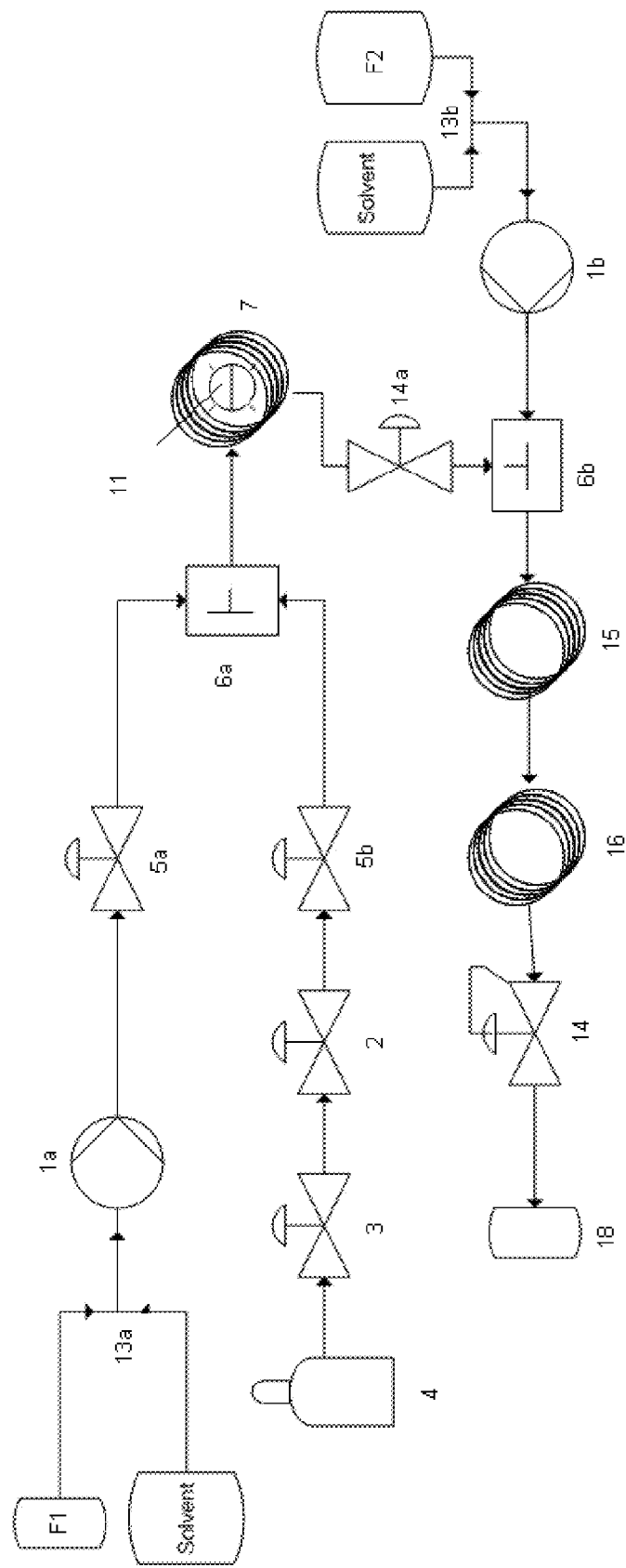
Figure 12:
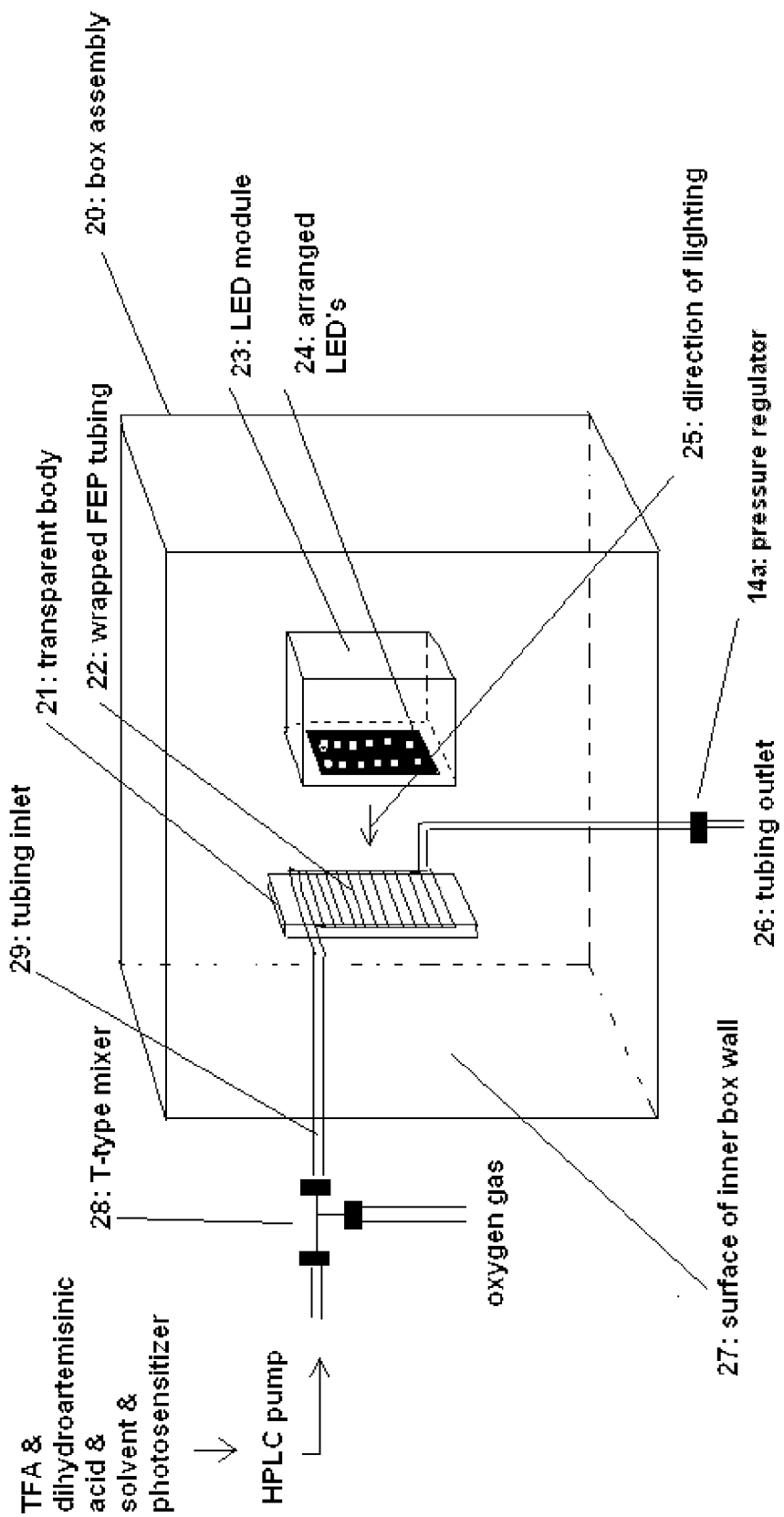
Figure 13:
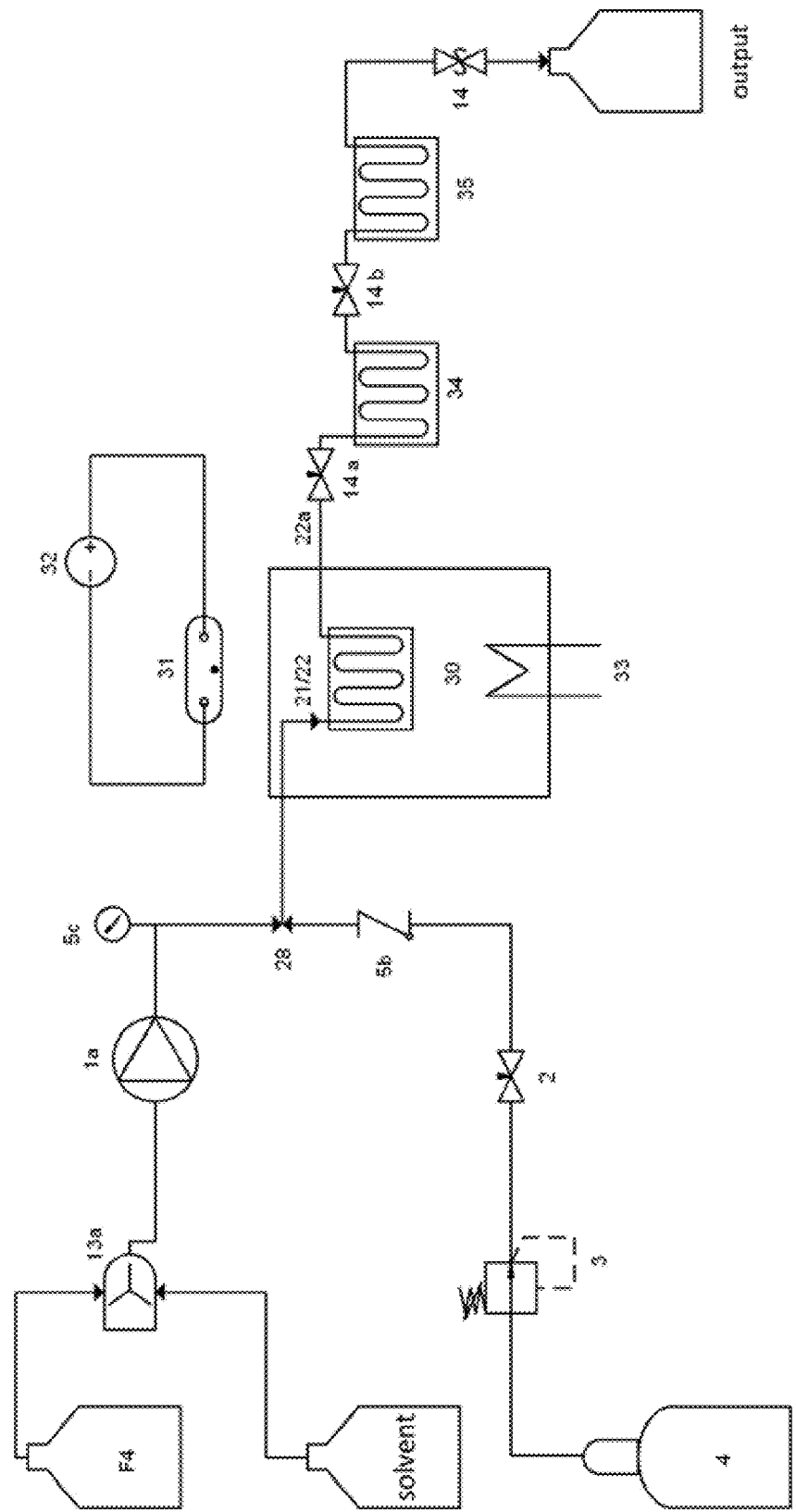
FIG. 13 System diagram of the continuous flow reactor of FIG. 8 further comprising an additional pressure regulators 14a and 14b.

To test the temperature dependence of the acid-catalyzed reaction cascade 4 mL of toluene were filled in a vial together with TFA and stirred while $O_2$ is bubbled through (7.5 mL/min). After 2 min 1 mL of the photooxidation stock solution containing hydroperoxides (3, 4, 5) was added, stirred and $O_2$ bubbling continued for 20 minutes or a longer time as indicated. The concentration of artemisinin and byproducts was evaluated by NMR without quenching by base. After stopping the reaction, unreacted peroxide is therefore mainly transformed into the aldehyde byproduct in the absence of oxygen. The overall yield for the complete reaction starting from DHAA is shown in FIG. 10A.

The highest yield of artemisinin is obtained for a reaction temperature of 25° C. Increasing the temperature results in a more pronounced formation of byproducts while the artemisinin yield decreases. At low temperature a decrease in yield is observed as well. Extending the reaction time could improve the artemisinin yield and decrease aldehyde formation (Table 6).

TABLE 6

| reaction time/min | temp/° C. | artemisinin (6) | 5-member lactone (7) | aldehyde (9) | cyclized peroxide (8) |
|---|---|---|---|---|---|
| 20 | −15 | 18.0% | 2.1% | 21.3% | 1.6% |
| 20 | 0 | 33.4% | 2.1% | 17.8% | 3.7% |
| 20 | 25 | 59.1% | 4.4% | 2.5% | 6.1% |
| 20 | 50 | 47.0% | 5.5% | 4.7% | 7.2% |
| 20 | 75 | 31.2% | 6.1% | 9.6% | 7.5% |
| 60 | 0 | 55.6% | 2.3% | 6.8% | 3.0% |
| 120 | −15 | 54.4% | 1.8% | 5.5% | 3.0% |

Example 10

Effect of Photosensitizers on Photooxidation in Continuous Flow Using the Cooled Box Assembly To evaluate the optimum photosensitizer concentration, a 0.5 M solution of dihydroartemisinic acid in dry toluene was prepared and benzoic acid added as internal standard. This solution (2 mL/min) and oxygen (5 mL/min at 10 bar, 2 eq) was injected with the Vapourtec system into a photoreactor (7 mL tubing in 4 layers around a polycarbonate plate, inner diameter 0.03 inch, 12 W LED lamp 420 nm). The photoreactor was immersed in an ethanol-water bath, which was cooled to −20° C. with an immersion cooler (Huber, TC100E-F-NR). The photoreactor was installed in front of the LED module at a distance of 3 cm. The use of dry toluene is advisable, as toluene of technical purity contained too much water, which crystallized inside the tubing resulting in partial clogging and strong pressure fluctuations. This could either be prevented by employing dry toluene or adding acetonitrile (around 0.5% v/v) to toluene of technical purity. A back pressure regulator (8 bar) was applied at the end of the system, resulting in a slightly fluctuating system pressure of 10-11 bar.

The system was flushed with pure solvent and then 5 mL of the stock solution with various amounts of photosensitizer was injected. The solution exiting the photochemical reactor was collected and analyzed by NMR. The three sensitizers tetraphenylporphyrin (TPP, singlet oxygen quantum yield $\Phi_A=0.63$ in benzene), zinc tetraphenylporphyrin (ZnTPP, $\Phi_A=0.83$ in benzene) and 9,10-dicyanoanthracene (DCA, $\Phi_A=1.56$ in benzene) were evaluated at different concentrations. All these dyes absorb blue light at 420 nm. The quantum yield of dicyanoanthracene is >1, because the excited dye can transfer its energy from the excited singlet and the triplet state to oxygen.

Conversion of dihydroartemisinic acid against sensitizer concentration is shown in FIG. 10B and the specific values in Table 7. Even with relatively low concentrations of TPP (0.05 mol %) a high conversion of dihydroartemisinic acid is achieved. Further increase in the concentration slightly improves the yield. Due to the low temperature, selectivity for the desired hydroperoxide was 85%.

In case of ZnTPP a higher efficiency would be expected, as the quantum yield of this complex is significantly larger. However, this sensitizer performs worse. A probable explanation was the strong photobleaching, as indicated by the colour change after passing the photochemical reactor. In addition to the decreased performance, also the selectivity for the desired hydroperoxide dropped to 82% on average.

For low concentrations of DCA, this sensitizer compares to TPP regarding conversion.

TABLE 7

| TPP | | ZnTPP | | DCA | |
| --- | --- | --- | --- | --- | --- |
| conc. [mM] | conversion | conc. [mM] | conversion | conc. [mM] | conversion |
| 0.23 | 73% | 0.205 | 48% | 0.6 | 77% |
| 0.75 | 76% | 0.55 | 53% | 1.05 | 72% |
| 1.15 | 74% | 0.85 | 57% | 2.45 | 91% |
| 1.95 | 69% | 1.2 | 54% | 3.25 | 88% |
| | | 1.45 | 55% | | |
| | | 2.25 | 55% | | |

Example 11

Synthesis of Artemisinin (6) in Continuous Flow Using the Cooled Box Assembly

The flow reactor setup for the synthesis of artemisinin consists of a feed for a solution of dihydroartemisinic acid, a pumping unit analogously to example 6 (consisting of an automated two inlet switch valve for regulating the composition of the feed for the solution of dihydroartemisinic acid, allowing for rapid switching from pure solvent to the solution containing the dissolved dihydroartemisinic acid, a HPLC pump (Vapourtec, R2C+ unit) downstream to switch valve), pumping the dihydroartemisinic acid solution with a throughput of 1.25 mL/min to a ETFE T-mixer (IDEX Health and Science, P-632) for mixing the dihydroartemisinic acid solution and the oxygen, a mass flow controller (Influx, SV1B5-Al05, allowing control of the oxygen flow rate from 5-90 cm$^3$/min) connected to a manometer fixed on an oxygen tank (Air Liquide, O$_2$ 99.995% pure), thus generating a steady oxygen flow of 5 mL/min, a check valve (IDEX Health and Science, inline check-valve CV-3010) between the mass flow controller and the mixer, a photochemical reactor comprising the mixer and a tubing inlet, consisting of multiple loops of FEP tubing (7 mL, IDEX Health & Science, fluorinated ethylene polymer 1520, natural color, outside diameter (OD) $\frac{1}{16}$ in and inside diameter (ID) 0.030 in) wrapped tightly around a transparent body (polycarbonate plate, size 9.0×14.0 cm$^2$) which is irradiated by an arrangement of 60 High Power LEDs combined in an LED module emitting at 420 nm (OSA Opto Lights, 72 W electrical power, cooled by a fan, emission area 2.5×2.5 cm$^2$), electronics for supplying a constant current to the LED module (OSA Opto Lights) and a power supply (Manson HCS-3202). The wrapped FEP tubing was irradiated directly by the LED module, which was installed in a distance of 3 cm in front of the transparent body. For maximum efficiency, the tubing was irradiated in a tray made of stainless steel to reflect throughpassing light onto the photochemical reactor, which was immersed in this tray, filled with an ethanol-water bath cooled to −20° C. with the help of an immersion cooler (Huber, TC100E-F-NR). After leaving the photochemical reactor a solution of trifluoroacetic acid was introduced with a second T-mixer and the help of a HPLC pump (Vapourtec, R2C+ unit) at a flow rate of 0.25 mL/min. The subsequent reactor was 15 ml (inner diameter 0.03 inch, FEP tubing), kept at 15° C. and then 30 mL (inner diameter 0.06 inch, FEP tubing), kept at room temperature. A back-pressure regulator of 8 bar (Vapourtec) was installed after the tubing outlet in order to increase the internal pressure of the system.

The feed was a solution of dihydroartemisinic acid at a concentration of 0.5 mol/L and the photosensitizer tetraphenylporphyrin at a concentration of 1 mmol/L in toluene (2.95 g dihydroartemisinic acid and 15 mg tetraphenylporphyrin, total volume 25 mL, volumetric flask). The feed was introduced at a flow rate of 1.25 mL/min and the oxygen flow adjusted to 5 mL/min. The solution of trifluoroacetic acid injected into the output stream of the photochemical reactor contains 1.93 mL trifluoroacetic acid filled up to 20 ml with toluene (1.25 M, volumetric flask). The output stream showed a conversion of 89% yielding 62% of the desired artemisinin with a selectivity of 70% (NMR of crude).

The solution was collected and extracted twice with sat. NaHCO$_3$ to quench the acid and then washed with water. The organic phase was dried over anhydrous Na$_2$SO$_4$ and concentrated under reduced pressure. Then hexane was added and evaporated to remove most of the remaining toluene. Another portion of hexane was added, the solution heated shortly and cooled down. The slurry was filtrated, washed with hexane and dried under vacuum to afford artemisinin as an off-white solid (1.713 g, 50% isolated yield).

Example 12

Synthesis of Artemisinin (6) in Continuous Flow Using the Cooled Box Assembly

The flow reactor setup for the synthesis of artemisinin consists of a feed for a mixture of dihydroartemisinic acid, trifluoroacetic acid and the photosensitizer dicyanoanthracene, a pumping unit analogously to example 6 (consisting of an automated two inlet switch valve for regulating the composition of the feed for the solution of dihydroartemisinic acid, allowing for rapid switching from pure solvent to the feed solution containing the dissolved dihydroartemisinic acid, an HPLC pump (Vapourtec, R2C+ unit) downstream to switch valve), pumping the dihydroartemisinic acid solution with a throughput of 1.25 mL/min to an ETFE T-mixer (IDEX Health and Science, P-632) for mixing the feed solution and oxygen, a mass flow controller (Influx, SV1B5-Al05, allowing control of the oxygen flow rate from 5-90 cm$^3$/min) connected to a manometer fixed on an oxygen tank (Air Liquide, $O_2$ 99.995% pure), thus generating a steady oxygen flow of 5 mL/min, a check valve (IDEX Health and Science, inline check-valve CV-3010) between the mass flow controller and the mixer, a photochemical reactor comprising the mixer and a tubing inlet, consisting of multiple loops of FEP tubing (7 mL, IDEX Health & Science, fluorinated ethylene polymer 1520, natural color, outside diameter (OD) ¹⁄₁₆ in and inside diameter (ID) 0.030 in) wrapped tightly around a transparent body (glass plate, size 9.0×14.0 cm$^2$) which is irradiated by an arrangement of 60 High Power LEDs combined in an LED module emitting at 420 nm (OSA Opto Lights, 72 W electrical power, cooled by a fan, emission area 2.5×2.5 cm$^2$), electronics for supplying a constant current to the LED module (OSA Opto Lights) and a power supply (Manson HCS-3202). The wrapped FEP tubing was irradiated directly by the LED module, which was installed in a distance of 3 cm in front of the transparent body. For maximum efficiency, the tubing was irradiated in a tray made of stainless steel to reflect through-passing light onto the photochemical reactor, which was immersed in this tray, filled with an ethylene glycol:water bath (3:2 v/v) cooled to −20° C. with the help of an immersion cooler (Huber, TC100E-F-NR). After leaving the photochemical reactor the solution was passed through a reactor with 10 ml volume (inner diameter 0.03 inch, FEP tubing), kept at 10° C. by immersion in a water bath and then 30 mL (inner diameter 0.06 inch, FEP tubing), kept at room temperature. A back-pressure regulator of 8 bar (Vapourtec) was installed after the tubing outlet in order to increase the internal pressure of the system.

The feed was a solution of dihydroartemisinic acid at a concentration of 0.5 mol/L, trifluoroacetic acid at a concentration of 0.25 mol/L and the photosensitizer dicyanoanthracene at a concentration of 2.5 mmol/L in toluene (29.5 g dihydroartemisinic acid, 7.13 g trifluoroacetic acid and 143 mg dicyanoanthracene, total volume 250 mL, volumetric flask). The feed was introduced at a flow rate of 1.25 mL/min and the oxygen flow adjusted to 5 mL/min.

The solution exiting the reactor was collected and extracted twice with sat. $NaHCO_3$ to quench the acid and then washed with water and brine. The organic phase was dried over anhydrous $Na_2SO_4$ and concentrated under reduced pressure, then acetonitrile was added and evaporated to remove most toluene and dried under high vacuum overnight, yielding 30.509 g crude containing 22.945 g artemisinin according to NMR analysis. Thus a yield of 65% was achieved at a conversion of 97%.

The crude was solubilized in 60 mL acetonitrile, activated carbon added and the solution refluxed shortly. After cooling down, the carbon was filtrated off with a PTFE syringe filter (0.45 μm) and the solvent was removed, yielding 29.735 g of a nearly white solid, as most dicyanoanthracene is removed by this procedure.

The solid was recrystallized from 150 mL cyclohexane:ethanol (9:1 v/v), which yielded off-white needles. These were filtrated, washed three times with 100 mL cyclohexane each and dried under high vacuum (16.515 g, pure artemisinin according to NMR analysis, 47% isolated yield, recovery of recrystallization 72%).

The dried mother liquor (13.288 g) was recrystallized from 50 mL cyclohexane. This yielded slightly yellow crystals, which were washed with cyclohexane and dried under high vacuum (3.597 g, consisting of artemisinin with 96% purity (3.446 g), isolated yield 10%, total combined isolated yield including first recrystallization 57% (87% recovery)).

Both artemisinin batches were combined and recrystallized from 150 mL cyclohexane:ethanol (9:1 v/v), yielding purely white needles, which were filtrated off and washed twice with cyclohexane (16.079 g of pure artemisinin, 46% isolated yield based on initial dihydroartemisinic acid).

Example 13

Synthesis of Artemisinin (6) in Continuous Flow Using the Cooled Box Assembly from Plant Extract of *Artemisia annua*

Extraction protocols to remove artemisinic acid and dihydroartemisinic acid from *artemisia annua* have been published (Wallaart, T. E. et al., *J. Nat. Prod.* 1999, 62, 430-433), making use of the extraction of acidic compounds by aqueous base and the reextraction into an organic phase after acidification. An adapted procedure was applied to mother liquor remaining after removal of artemisinin from *artemisia annua* extracts. 20 g of mother liquor (containing 8.2% dihydroartemisinic acid according to HPLC analysis) was mixed with 100 mL diethyl ether and extracted twice with 50 mL 5% aqueous $K_2CO_3$. The basic extract was acidified with conc. HCl to pH 1 and extracted twice with 50 mL diethyl ether. The diethyl ether extract was washed once with water, dried over anhydrous $Na_2SO_4$, the solvent removed and the crude dried under high vacuum. A yellow oil remained which slowly crystallized (3.653 g). NMR of this basic extract with mesitylene as internal standard showed dihydroartemisinic acid (41.8%) and artemisinic acid (7.4%). From the 20 g of raw extract, 1.53 g dihydroartemisinic acid could be recovered (7.7% based on initial mother liquor, 94% recovery). This enriched extract was used as such without further purification. Dicyanoanthracene (14 mg, 0.063 mmol) and trifluoroacetic acid (710 mg, 6.23 mmol) was added to the extract and the solution filled to 25 mL with toluene (volumetric flask). This mixture was used as feed solution and introduced into the fully continuous process as described in example 8.

The product solution was collected and extracted once with sat. $NaHCO_3$ to quench the acid, once with 5% $K_2CO_3$ to extract acidic impurities and then washed with water and brine. The organic phase was dried over anhydrous $Na_2SO_4$ and concentrated under reduced pressure, yielding a yellow solid that was dried under high vacuum overnight (2.164 g) and contained 1.042 g artemisinin (based on the initial 1.53 g dihydroartemisinic acid the crude yield is 57%). The solid was recrystallized from cyclohexane:ethanol (9:1 v/v). Off-white crystals were obtained, filtered off and washed with cyclohexane. The solid was dried under high vacuum (761 mg, 42% isolated yield, pure artemisinin by NMR, 73% recovery by recrystallization).

The invention claimed is:
1. A photochemical reactor for the production of artemisinin from dihydroartemisinic acid comprising:
   a light source,
   an oxygen source,
   mixing device for mixing oxygen with a solution of dihydroartemisinic acid,
   reactor compartment exposed to the light source for irradiating the mixture of the solution of dihydroartemisinic acid and oxygen when the mixture passes the reactor compartment, and
   a back pressure regulator.

2. The photochemical reactor according to claim 1, wherein the reactor compartment is a tubing.

3. The photochemical reactor according to claim 1, wherein the mixing device is a T-mixer valve.

4. The photochemical reactor according to claim 1 further comprising
- a box which is impervious to light with light reflecting inner walls and one opening through which the tubing enters the box and another opening through which the tubing leaves the box and
- multiple loops of the tubing arranged in the inside of the box, wherein the tubing has an inlet for a mixture of dihydroartemisinic acid and oxygen on its one end before entering the box and an outlet for the reacted products on the opposite end after leaving the box.

5. The photochemical reactor according to claim 1 further comprising
- a cooling liquid and a chiller.

6. The photochemical reactor according to claim 4 further comprising
- a cooling liquid and a chiller.

7. A continuous flow reactor for the production of artemisinin from dihydroartemisinic acid comprising:
- a light source,
- an oxygen source,
- mixing device for mixing oxygen with a solution of dihydroartemisinic acid,
- reactor compartment exposed to the light source for irradiating the mixture of dihydroartemisinic acid and oxygen when the mixture passes the reactor compartment,
- a back pressure regulator, and
- a feed for an acidic solution.

8. The continuous flow reactor according to claim 7, further comprising
- at least one reactor for producing artemisinin or completing the synthesis of artemisinin, and
- a collection flask for collecting the artemisinin containing solution from the at least one reactor.

9. The continuous flow reactor according to claim 7, further comprising
- a second reactor downstream to the first reactor or
- a second reactor downstream to the first reactor and a third reactor downstream to the second reactor.

10. The continuous flow reactor according to claim 8, further comprising
- a second reactor downstream to the first reactor or
- a second reactor downstream to the first reactor and a third reactor downstream to the second reactor.

* * * * *